(12) United States Patent
Hayashi et al.

(10) Patent No.: US 8,206,896 B2
(45) Date of Patent: Jun. 26, 2012

(54) DETECTION OF UTERINE LEIOMYOSARCOMA USING LMP2

(75) Inventors: Takuma Hayashi, Nagano (JP); Yukihiro Kobayashi, Nagano (JP); Kenji Sano, Nagano (JP); Akiko Horiuchi, Nagano (JP); Ikuo Konishi, Nagano (JP)

(73) Assignee: Shinshu University, Matsumoto-shi (JP)

( * ) Notice: Subject to any disclaimer, the term of this patent is extended or adjusted under 35 U.S.C. 154(b) by 831 days.

(21) Appl. No.: 12/095,585

(22) PCT Filed: Nov. 30, 2006

(86) PCT No.: PCT/JP2006/324403
§ 371 (c)(1),
(2), (4) Date: May 30, 2008

(87) PCT Pub. No.: WO2007/064038
PCT Pub. Date: Jun. 7, 2007

(65) Prior Publication Data
US 2011/0020792 A1   Jan. 27, 2011

(30) Foreign Application Priority Data
Nov. 30, 2005   (JP) ................................. 2005-347227

(51) Int. Cl.
*C12Q 1/00* (2006.01)
*G01N 33/53* (2006.01)
*G01N 33/574* (2006.01)

(52) U.S. Cl. .............................. 435/4; 435/7.1; 435/7.23

(58) Field of Classification Search .................. 530/326, 530/327, 388, 389; 424/192, 195; 435/334, 435/6
See application file for complete search history.

(56) References Cited

OTHER PUBLICATIONS

Zhai et al. (Int. J. Cancer (Pred. Oncol.): 84, 244-250, 1999.*
Hayashi et al. (Cancer Research 62, 24-27, Jan. 1, 2002.*
Krishnakumar et al. (Cancer, Mar. 1, 2004;100(5):1059-69).*
Del Pizzo et al. (Am J Pathol 1999, 155:1129-1136).*
Boyd (The Basic Science of Oncology, 1992, McGraw-Hill, Inc., p. 379).*
Paul Brooks, et al., "Association of Immunoproteasomes with the Endoplasmic Reticulum", The Biochemical Journal, vol. 352 Pt 3, XP002507505, Dec. 15, 2000, pp. 611-615.
Katerina Politi, et al., "A Mouse Model of Uterine Leiomyosarcoma", American Journal of Pathology, vol. 164, No. 1, Jan. 1, 2004, 12 pages.
K. Delp, et al., "Functional deficiencies of components of th MHC class I antigen pathway in human tumors of epithelial origin", Bone Marrow Transplantation, 25, suppl. 2, XP-001128767, May 2000, pp. S88-S95.

Barbara Seliger, et al., "Characterization of the Major Histocompatibility Complex Class I Deficiencies in B16 Melanoma Cells[1]", Cancer Research, 61, Feb. 1, 2001, pp. 1095-1099.
Hitomi Tsukada, et al. "F. Fluorodeoxyglucose uptake in uterine leiomyomas in healthy women" Clinical Imaging 33 (2009) 462-467.
Nikkei Medical Online, Cancer Experts News, Jul. 27, 2009 (English Translation Exhibit D).
Takuma Hayashi, "Linking of 26S Proteasome Inactivation and Cancer Development", Experimental Medicine, vol. 21. No. 7, May 2003.
T. Hayashi, et al., "The Mutation in the ATP-Binding Region of JAK1, Identified in Human Uterine Leiomyosarcomas, Results in Defective Interferonγ Inducibility of TAP1 and LMP2", Oncogene (2006) 25, 4016-4026.
Ya-Li Zhai, et al., "Expression of Cyclins and Cyclin-Dependent Kinases in Smooth Muscle Tumors of the Uterus", Int. J. Cancer (Pred.Oncol.): 84, (1999), 244-250.
Maria-Teresa Valenti, et al., Differentiation, Proliferation and Apoptosis Levels in Human Leiomyoma and Leiomyosarcoma, J. Cancer Res. Clin. Oncol (1998) 124: 93-105.
Kalevi J. A. Kairemo, et al., "Radioimmunodetection of Uterine Leiomyosarcoma with [111] In-Labeled Monoclonal Antimyosin Antibody Fab Fragments", Gynecologic Oncology 36, (1999), 417-422.
Susan E. Dovhey, et al., "Loss of Interferon-γ Inducibility of TAP1 and LMP2 in a Renal Cell Carcinoma Cell Line [1]", Cancer Research 60. Oct. 15, 2000, 5789-5796.
Michael R. Rossi, et al., "Identification of inactivating mutations in the JAK1, SYNJ2, and CLPTM1 genes in prostate cancer cells using inhibition of nonsense-mediated decay and microarray analysis", Cancer Genetics and Cytogenetics 161 (2005) 97-103.
Takuma Hayashi, et al., "Development of Spontaneous Uterine Tumors in Low Molecular Mass Polypeptide-2 Knockout Mice[1]", Cancer Research 62, Jan. 1, 2002, 24-27.
Kenneth L. Wright, et al., "Coordinate Regulation of the Human TAP1 and LMP2 Genes from a Shared Bidirectional Promoter" J. Exp. Med. The Rockefeller University Press, vol. 181, Apr. 1995, 1459-1471.
S. Niesporek, et al., "Polymorphismis of transporter associated with antigen processing type 1 (TAP1), proteasome subunit beta type 9 (PSMB9) and their common promoter in African children with different manifestations of malaria", International Journal of Immunogenetics 32, 7-11, Feb. 2005.
The Faseb Journal, A Multidisplinary Resource for the Life Sciences, Experimental Biology 2001, Orlando Florida, vol. 15, No. 5, Mar. 8, 2001.
Eiji Satoh et al., "Reduced Expression of the Transporter Associated with Antigen Processing 1 Molecule in Malignant Glioma Cells, and its Restoration by Interferon-γ and -β", J Neurosurg. Feb. 2006;104(2):264-71.

*Primary Examiner* — Peter J Reddig
*Assistant Examiner* — Yan Xiao
(74) *Attorney, Agent, or Firm* — Oblon, Spivak, McClelland, Maier & Neustadt, L.L.P.

(57) ABSTRACT

This invention provides a method for detecting the presence of uterine leiomyosarcoma using the transcription or expression level of LMP2 and/or cyclin E in uterine smooth muscle tissue as an indicator and a method for detecting uterine leiomyosarcoma using LMP2 and/or cyclin E as a marker.

3 Claims, 32 Drawing Sheets

Fig. 12

Biological and proliferative characteristics in LMP2 gene expressing cell

| | Cell line | Morphology | Doubling time (hours) | Fibronectin expression |
|---|---|---|---|---|
| | Original SKN | Genetic transformation | 15.2 | (-/+) |
| LMP2 | SKIN-LMP2 (-/+) | Genetic transformation | 15.4 | (+) |
| | SKIN-LMP2 (+++) | Flat revertant-like morphology | 17.3 | (+++) |
| | UtSMC (Normal human uterine smooth muscle cell) | Flat revertant-like morphology | 19.4 | (+++++) |

Fig. 14

| Patient | | Diagnosis | LMP2 |
|---|---|---|---|
| Uterus | 086823 | Uterine myosarcoma | - |
| | 02010255 | Uterine myosarcoma | - |
| | 04001622 | Uterine myosarcoma | -/+ |
| | 05001052 | Uterine myosarcoma | - |
| | 900092 | Low-malignancy uterine leiomyosarcoma | - |
| | 92003523 | Low-malignancy uterine leiomyosarcoma | - |
| | 93006520 | Low-malignancy uterine leiomyosarcoma | -/+ |
| | 97001517 | Low-malignancy uterine leiomyosarcoma | - |
| | 03011251 | Leiomyosarcoma in the uterine epithelium | + |
| | 04004486 | Endometrial stromal sarcoma | - |
| | 0503533 | Leiomyoma | ++ |
| | 01009296 | Normal smooth muscle cell | ++ |
| Other tumors | 95002965 | Primary retroperitoneal leiomyosarcoma | - |
| | 99007593 | Primary omental leiomyosarcoma | ++ |
| | 01011511 | Primary leiomyosarcoma of the small intestine (GIST) | + |
| | 04009854 | Primary mesenteric leiomyosarcoma | - |

Fig. 16

| Patient | JAK1 kinase | LMP2 promoter region | STAT1(701Y,727S)[4] | JAK2 kinase | LMP2 |
|---|---|---|---|---|---|
| SKN cells | G781E(ATP)[1] | wt | (I702L)[5] | wt | Neg. |
| #1 | wt | wt | | wt | Neg. |
| #2 | wt | A210G, C214T(IRF-E)[3] | wt | wt | Neg. |
| #3 | Q986P(Activity) R995S(Activity)[2] | C214T, G219A(IRF-E) | wt | wt | Neg. |
| #4 | G876R(ATP) | wt | (S710A)[5] | wt | P.Posi. |
| #5 | C881F(ATP) | wt | wt | wt | Neg. |
| #6 | wt | wt | wt | wt | Neg. |
| #7 | wt | A216G(IRF-E) | (L693R)[5] | wt | Neg. |
| #8 | wt | wt | wt | wt | P.Posi. |
| #9 | Y987S(Activity) | wt | wt | wt | Neg. |
| #10 | wt | A217G(IRF-E) | (R716S)[5] | wt | Neg. |
| #11 | wt | wt | (I702L)[5] | wt | P.Posi. |
| #12 | wt | wt | wt | wt | Neg. |
| #13 | Y987S(Activity) | A216G(IRF-E) | wt | wt | Neg. |

[1] ATP-binding region of JAK1
[2] Kinase activation site of JAK1
[3] Interferon γ control element enhanced site
[4] Phosphorylation of Tyr701 or Ser727 in STAT1
[5] No mutation is observed in STAT1 functional site
Neg. = negative
P. Posi. = Partially positive

Fig. 17

| Mutation in interferon γ signal transduction pathway in uterine leiomyosarcoma |||||||
| Region in a gene | Locus | GenBank Accession No. | Counting | Tumor | Nucleotide | Amino acid | Domain |
| --- | --- | --- | --- | --- | --- | --- | --- |
| JAK1 | HUMPTKJAK1 | M64174 | NT_086582 | ULMS | G2612A<br>G2626A<br>G2642T<br>A2967C<br>A2960C<br>A2985T | G781E<br>G876R<br>C881F<br>G986P<br>Y987S<br>R995S | ATP-binding<br>ATP-binding<br>ATP-binding<br>Active site<br>Active site<br>Active site |
| JAK2 | AF005216 | AF005216 | NT_008413.17 | ULMS | ND² | ND | ND |
| STAT1 | NM_007315 | NM_007315 | NT_005403.16 | ULMS | A2104C<br>T2128G<br>T2078G<br>A2148C | I702L<br>S710A<br>L693R<br>R716S | NA³<br>NA<br>NA<br>NA |
| LMP2¹ | | | NT_086690 | ULMS | A210G<br>C214T<br>A216G<br>A217G<br>G219A | | IRF-E site<br>IRF-E site<br>IRF-E site<br>IRF-E site<br>IRF-E site |

¹ LMP2 promoter region
² Not detected
³ Non-kinase activation site

Fig. 18

|  | N | LMP2 |
|---|---|---|
| Normal | 21 | ++++ |
| Leiomyoma | 24 | ++++ |
| Endometrial stromal sarcoma | 6 | +/- |
| Leiomyosarcoma | 29 | - |

Fig. 19

| | Colony count [a] | | |
|---|---|---|---|
| Vector DNA | pCEM9 | pCEM9-LMP2 | |
| G418[R] (total) | 59.2 | 54.3 | (A) |
| Partially flat revertant-like morphology [b] | 0 | 26.3 (48.4%) | (B) |
| Flat revertant-like morphology [c] | 0 | 16.0 (29.5%) | (C) |

[a] Total colony counts observed
(Numerical values in between parentheses indicate total counts of G418-resistant colonies)
[b] Observed 1 week after G418 selection
[c] Observed 3 weeks after G418 selection

Fig. 21

| | Cell line | Biological/growth characteristics of transfectant | | |
|---|---|---|---|---|
| | | Morphology | Doubling time (hours) | Fibronectin expression |
| | Original SKN | Transformation | 15.2 | (-/+) |
| | pCEM9 SKN | Transformation | 15.3 | (-/+) |
| LMP2 | SKN-LMP2(-/+) | Transformation | 15.4 | (+) |
| | SKN-LMP2(+++) | Flat revertant-like morphology | 17.3 | (++) |
| | Cryo UtSMC (Normal human uterine smooth muscle cell) | Flat revertant-like morphology | 19.4 | (+++) |

Fig. 23C

Fig. 24

|  | SKN | #121 | Multiple number |
|---|---|---|---|
| LMP2 | P 63.0 | P 348.2 | 5.53 |
| Cyclin E | P 368.0 | A 10.8 | 0.03 |
| ERa | A 6.4 | P 500.7 | 78.23 |
| ERb | A 20.1 | P 52.2 | 2.60 |
| Myosin VB | A 26.2 | P 393.9 | 15.03 |

SEQUENCE LISTING

```
<160> NUMBER OF SEQ ID NOS: 8

<210> SEQ ID NO 1
<211> LENGTH: 645
<212> TYPE: DNA
<213> ORGANISM: Homo sapiens
<220> FEATURE:
<221> NAME/KEY: CDS
<222> LOCATION: (10)..(639)

<400> SEQUENCE: 1 cttgcaggg atg ctg cgc gcg gga gaa gtc cac acc ggg acc acc atc atg      51
          Met Leu Arg Ala Gly Glu Val His Thr Gly Thr Thr Ile Met
           1               5                  10 gca gtg gag ttt gac ggg ggc gtt gtg atg ggt tct gat tcc cga gtg       99
Ala Val Glu Phe Asp Gly Gly Val Val Met Gly Ser Asp Ser Arg Val
 15                  20                  25                  30 tct gca ggc gag gcg gtg gtg aac cga gtg ttt gac aag ctg tcc ccg      147
Ser Ala Gly Glu Ala Val Val Asn Arg Val Phe Asp Lys Leu Ser Pro
                 35                  40                  45 ctg cac gag cgc atc tac tgt gca ctc tct ggt tca gct gct gat gcc      195
Leu His Glu Arg Ile Tyr Cys Ala Leu Ser Gly Ser Ala Ala Asp Ala
             50                  55                  60 caa gcc gtg gcc gac atg gcc gcc tac cag ctg gag ctc cat ggg ata      243
Gln Ala Val Ala Asp Met Ala Ala Tyr Gln Leu Glu Leu His Gly Ile
         65                  70                  75 gaa ctg gag gaa cct cca ctt gtt ttg gct gct gca aat gtg gtg aga      291
Glu Leu Glu Glu Pro Pro Leu Val Leu Ala Ala Ala Asn Val Val Arg
     80                  85                  90 aat atc agc tat aaa tat cga gag gac ttg tct gca cat ctc atg gta      339
Asn Ile Ser Tyr Lys Tyr Arg Glu Asp Leu Ser Ala His Leu Met Val
 95                 100                 105                 110 gct ggc tgg gac caa cgt gaa gga ggt cag gta tat gga acc ctg gga      387
Ala Gly Trp Asp Gln Arg Glu Gly Gly Gln Val Tyr Gly Thr Leu Gly
                115                 120                 125 gga atg ctg act cga cag cct ttt gcc att ggt ggc tcc ggc agc acc      435
```

```
Gly Met Leu Thr Arg Gln Pro Phe Ala Ile Gly Gly Ser Gly Ser Thr
            130                 135                 140 ttt atc tat ggt tat gtg gat gca gca tat aag cca ggc atg tct ccc      483
Phe Ile Tyr Gly Tyr Val Asp Ala Ala Tyr Lys Pro Gly Met Ser Pro
145                 150                 155 gag gag tgc agg cgc ttc acc aca gac gct att gct ctg gcc atg agc      531
Glu Glu Cys Arg Arg Phe Thr Thr Asp Ala Ile Ala Leu Ala Met Ser
        160                 165                 170 cgg gat ggc tca agc ggg ggt gtc atc tac ctg gtc act att aca gct      579
Arg Asp Gly Ser Ser Gly Gly Val Ile Tyr Leu Val Thr Ile Thr Ala
175                 180                 185                 190 gcc ggt gtg gac cat cga gtc atc ttg ggc aat gaa ctg cca aaa ttc      627
Ala Gly Val Asp His Arg Val Ile Leu Gly Asn Glu Leu Pro Lys Phe
                195                 200                 205 tat gat gag tga accttc                                                645
Tyr Asp Glu
```

<210> SEQ ID NO 2
<211> LENGTH: 209
<212> TYPE: PRT
<213> ORGANISM: Homo sapiens

<400> SEQUENCE: 2

```
Met Leu Arg Ala Gly Glu Val His Thr Gly Thr Thr Ile Met Ala Val
1               5                   10                  15

Glu Phe Asp Gly Gly Val Val Met Gly Ser Asp Ser Arg Val Ser Ala
                20                  25                  30

Gly Glu Ala Val Val Asn Arg Val Phe Asp Lys Leu Ser Pro Leu His
            35                  40                  45

Glu Arg Ile Tyr Cys Ala Leu Ser Gly Ser Ala Ala Asp Ala Gln Ala
        50                  55                  60

Val Ala Asp Met Ala Ala Tyr Gln Leu Glu Leu His Gly Ile Glu Leu
65                  70                  75                  80

Glu Glu Pro Pro Leu Val Leu Ala Ala Ala Asn Val Val Arg Asn Ile
                85                  90                  95

Ser Tyr Lys Tyr Arg Glu Asp Leu Ser Ala His Leu Met Val Ala Gly
            100                 105                 110

Trp Asp Gln Arg Glu Gly Gly Gln Val Tyr Gly Thr Leu Gly Gly Met
        115                 120                 125

Leu Thr Arg Gln Pro Phe Ala Ile Gly Gly Ser Gly Ser Thr Phe Ile
130                 135                 140

Tyr Gly Tyr Val Asp Ala Ala Tyr Lys Pro Gly Met Ser Pro Glu Glu
145                 150                 155                 160

Cys Arg Arg Phe Thr Thr Asp Ala Ile Ala Leu Ala Met Ser Arg Asp
                165                 170                 175

Gly Ser Ser Gly Gly Val Ile Tyr Leu Val Thr Ile Thr Ala Ala Gly
            180                 185                 190

Val Asp His Arg Val Ile Leu Gly Asn Glu Leu Pro Lys Phe Tyr Asp
        195                 200                 205

Glu
```

<210> SEQ ID NO 3
<211> LENGTH: 3541
<212> TYPE: DNA
<213> ORGANISM: Homo sapiens
<220> FEATURE:
<221> NAME/KEY: CDS
<222> LOCATION: (76)..(3504)

```
<400> SEQUENCE: 3
tccagtttgc ttcttggaga acactggaca gctgaataaa tgcagtatct aaatataaaa      60
gaggactgca atgcc atg gct ttc tgt gct aaa atg agg agc tcc aag aag     111
              Met Ala Phe Cys Ala Lys Met Arg Ser Ser Lys Lys
                1               5                  10 act gag gtg aac ctg gag gcc cct gag cca ggg gtg gaa gtg atc ttc     159
Thr Glu Val Asn Leu Glu Ala Pro Glu Pro Gly Val Glu Val Ile Phe
         15                  20                  25 tat ctg tcg gac agg gag ccc ctc cgg ctg ggc agt gga gag tac aca     207
Tyr Leu Ser Asp Arg Glu Pro Leu Arg Leu Gly Ser Gly Glu Tyr Thr
     30                  35                  40 gca gag gaa ctg tgc atc agg gct gca cag gca tgc cgt atc tct cct     255
Ala Glu Glu Leu Cys Ile Arg Ala Ala Gln Ala Cys Arg Ile Ser Pro
 45                  50                  55                  60 ctt tgt cac aac ctc ttt gcc ctg tat gac gag aac acc aag ctc tgg     303
Leu Cys His Asn Leu Phe Ala Leu Tyr Asp Glu Asn Thr Lys Leu Trp
                 65                  70                  75 tat gct cca aat cgc acc atc acc gtt gat gac aag atg tcc ctc cgg     351
Tyr Ala Pro Asn Arg Thr Ile Thr Val Asp Asp Lys Met Ser Leu Arg
             80                  85                  90 ctc cac tac cgg atg agg ttc tat ttc acc aat tgg cat gga acc aac     399
Leu His Tyr Arg Met Arg Phe Tyr Phe Thr Asn Trp His Gly Thr Asn
         95                 100                 105 gac aat gag cag tca gtg tgg cgt cat tct cca aag aag cag aaa aat     447
Asp Asn Glu Gln Ser Val Trp Arg His Ser Pro Lys Lys Gln Lys Asn
     110                 115                 120 ggc tac gag aaa aaa aag att cca gat gca acc cct ctc ctt gat gcc     495
Gly Tyr Glu Lys Lys Lys Ile Pro Asp Ala Thr Pro Leu Leu Asp Ala
125                 130                 135                 140 agc tca ctg gag tat ctg ttt gct cag gga cag tat gat ttg gtg aaa     543
Ser Ser Leu Glu Tyr Leu Phe Ala Gln Gly Gln Tyr Asp Leu Val Lys
                145                 150                 155 tgc ctg gct cct att cga gac ccc aag acc gag cag gat gga cat gat     591
Cys Leu Ala Pro Ile Arg Asp Pro Lys Thr Glu Gln Asp Gly His Asp
            160                 165                 170 att gag aac gag tgt cta ggg atg gct gtc ctg gcc atc tca cac tat     639
Ile Glu Asn Glu Cys Leu Gly Met Ala Val Leu Ala Ile Ser His Tyr
        175                 180                 185 gcc atg atg aag aag atg cag ttg cca gaa ctg ccc aag gac atc agc     687
Ala Met Met Lys Lys Met Gln Leu Pro Glu Leu Pro Lys Asp Ile Ser
    190                 195                 200 tac aag cga tat att cca gaa aca ttg aat aag tcc atc aga cag agg     735
Tyr Lys Arg Tyr Ile Pro Glu Thr Leu Asn Lys Ser Ile Arg Gln Arg
205                 210                 215                 220 aac ctt ctc acc agg atg cgg ata aat aat gtt ttc aag gat ttc cta     783
Asn Leu Leu Thr Arg Met Arg Ile Asn Asn Val Phe Lys Asp Phe Leu
                225                 230                 235 aag gaa ttt aac aac aag acc att tgt gac agc agc gtg tcc acg cat     831
Lys Glu Phe Asn Asn Lys Thr Ile Cys Asp Ser Ser Val Ser Thr His
            240                 245                 250 gac ctg aag gtg aaa tac ttg gct acc ttg gaa act ttg aca aaa cat     879
Asp Leu Lys Val Lys Tyr Leu Ala Thr Leu Glu Thr Leu Thr Lys His
        255                 260                 265 tac ggt gct gaa ata ttt gag act tcc atg tta ctg att tca tca gaa     927
Tyr Gly Ala Glu Ile Phe Glu Thr Ser Met Leu Leu Ile Ser Ser Glu
    270                 275                 280 aat gag atg aat tgg ttt cat tcg aat gac ggt gga aac gtt ctc tac     975
Asn Glu Met Asn Trp Phe His Ser Asn Asp Gly Gly Asn Val Leu Tyr
285                 290                 295                 300
```

```
tac gaa gtg atg gtg act ggg aat ctt gga atc cag tgg agg cat aaa    1023
Tyr Glu Val Met Val Thr Gly Asn Leu Gly Ile Gln Trp Arg His Lys
            305                 310                 315 cca aat gtt gtt tct gtt gaa aag gaa aaa aat aaa ctg aag cgg aaa    1071
Pro Asn Val Val Ser Val Glu Lys Glu Lys Asn Lys Leu Lys Arg Lys
        320                 325                 330 aaa ctg gaa aat aaa gac aag aag gat gag gag aaa aac aag atc cgg    1119
Lys Leu Glu Asn Lys Asp Lys Lys Asp Glu Glu Lys Asn Lys Ile Arg
            335                 340                 345 gaa gag tgg aac aat ttt tca ttc ttc cct gaa atc act cac att gta    1167
Glu Glu Trp Asn Asn Phe Ser Phe Phe Pro Glu Ile Thr His Ile Val
        350                 355                 360 ata aag gag tct gtg gtc agc att aac aag cag gac aac aag aaa atg    1215
Ile Lys Glu Ser Val Val Ser Ile Asn Lys Gln Asp Asn Lys Lys Met
365                 370                 375                 380 gaa ctg aag ctc tct tcc cac gag gag gcc ttg tcc ttt gtg tcc ctg    1263
Glu Leu Lys Leu Ser Ser His Glu Glu Ala Leu Ser Phe Val Ser Leu
            385                 390                 395 gta gat ggc tac ttc cgg ctc aca gca gat gcc cat cat tac ctc tgc    1311
Val Asp Gly Tyr Phe Arg Leu Thr Ala Asp Ala His His Tyr Leu Cys
        400                 405                 410 acc gac gtg gcc ccc ccg ttg atc gtc cac aac ata cag aat ggc tgt    1359
Thr Asp Val Ala Pro Pro Leu Ile Val His Asn Ile Gln Asn Gly Cys
            415                 420                 425 cat ggt cca atc tgt aca gaa tac gcc atc aat aaa ttg cgg caa gaa    1407
His Gly Pro Ile Cys Thr Glu Tyr Ala Ile Asn Lys Leu Arg Gln Glu
        430                 435                 440 gga agc gag gag ggg atg tac gtg ctg agg tgg agc tgc acc gac ttt    1455
Gly Ser Glu Glu Gly Met Tyr Val Leu Arg Trp Ser Cys Thr Asp Phe
445                 450                 455                 460 gac aac atc ctc atg acc gtc acc tgc ttt gag aag tct gag cag gtg    1503
Asp Asn Ile Leu Met Thr Val Thr Cys Phe Glu Lys Ser Glu Gln Val
            465                 470                 475 cag ggt gcc cag aag cag ttc aag aac ttt cag atc gag gtg cag aag    1551
Gln Gly Ala Gln Lys Gln Phe Lys Asn Phe Gln Ile Glu Val Gln Lys
        480                 485                 490 ggc cgc tac agt ctg cac ggt tcg gac cgc agc ttc ccc agc ttg gga    1599
Gly Arg Tyr Ser Leu His Gly Ser Asp Arg Ser Phe Pro Ser Leu Gly
            495                 500                 505 gac ctc atg agc cac ctc aag aag cag atc ctg cgc acg gat aac atc    1647
Asp Leu Met Ser His Leu Lys Lys Gln Ile Leu Arg Thr Asp Asn Ile
510                 515                 520 agc ttc atg cta aaa cgc tgc tgc cag ccc aag ccc cga gaa atc tcc    1695
Ser Phe Met Leu Lys Arg Cys Cys Gln Pro Lys Pro Arg Glu Ile Ser
525                 530                 535                 540 aac ctg ctg gtg gct act aag aaa gcc cag gag tgg cag ccc gtc tac    1743
Asn Leu Leu Val Ala Thr Lys Lys Ala Gln Glu Trp Gln Pro Val Tyr
            545                 550                 555 ccc atg agc cag ctg agt ttc gat cgg atc ctc aag aag gat ctg gtg    1791
Pro Met Ser Gln Leu Ser Phe Asp Arg Ile Leu Lys Lys Asp Leu Val
        560                 565                 570 cag ggc gag cac ctt ggg aga ggc acg aga aca cac atc tat tct ggg    1839
Gln Gly Glu His Leu Gly Arg Gly Thr Arg Thr His Ile Tyr Ser Gly
        575                 580                 585 acc ctg atg gat tac aag gat gac gaa gga act tct gaa gag aag aag    1887
Thr Leu Met Asp Tyr Lys Asp Asp Glu Gly Thr Ser Glu Glu Lys Lys
        590                 595                 600 ata aaa gtg atc ctc aaa gtc tta gac ccc agc cac agg gat att tcc    1935
Ile Lys Val Ile Leu Lys Val Leu Asp Pro Ser His Arg Asp Ile Ser
605                 610                 615                 620
```

```
ctg gcc ttc ttc gag gca gcc agc atg atg aga cag gtc tcc cac aaa    1983
Leu Ala Phe Phe Glu Ala Ala Ser Met Met Arg Gln Val Ser His Lys
                625                 630                 635 cac atc gtg tac ctc tat ggc gtc tgt gtc cgc gac gtg gag aat atc    2031
His Ile Val Tyr Leu Tyr Gly Val Cys Val Arg Asp Val Glu Asn Ile
            640                 645                 650 atg gtg gaa gag ttt gtg gaa ggg ggt cct ctg gat ctc ttc atg cac    2079
Met Val Glu Glu Phe Val Glu Gly Gly Pro Leu Asp Leu Phe Met His
        655                 660                 665 cgg aaa agt gat gtc ctt acc aca cca tgg aaa ttc aaa gtt gcc aaa    2127
Arg Lys Ser Asp Val Leu Thr Thr Pro Trp Lys Phe Lys Val Ala Lys
    670                 675                 680 cag ctg gcc agt gcc ctg agc tac ttg gag gat aaa gac ctg gtc cat    2175
Gln Leu Ala Ser Ala Leu Ser Tyr Leu Glu Asp Lys Asp Leu Val His
685                 690                 695                 700 gga aat gtg tgt act aaa aac ctc ctc ctg gcc cgt gag gga atc gac    2223
Gly Asn Val Cys Thr Lys Asn Leu Leu Leu Ala Arg Glu Gly Ile Asp
                705                 710                 715 agt gag tgt ggc cca ttc atc aag ctc agt gac ccc ggc atc ccc att    2271
Ser Glu Cys Gly Pro Phe Ile Lys Leu Ser Asp Pro Gly Ile Pro Ile
            720                 725                 730 acg gtg ctg tct agg caa gaa tgc att gaa cga atc cca tgg att gct    2319
Thr Val Leu Ser Arg Gln Glu Cys Ile Glu Arg Ile Pro Trp Ile Ala
        735                 740                 745 cct gag tgt gtt gag gac tcc aag aac ctg agt gtg gct gct gac aag    2367
Pro Glu Cys Val Glu Asp Ser Lys Asn Leu Ser Val Ala Ala Asp Lys
    750                 755                 760 tgg agc ttt gga acc acg ctc tgg gaa atc tgc tac aat ggc gag atc    2415
Trp Ser Phe Gly Thr Thr Leu Trp Glu Ile Cys Tyr Asn Gly Glu Ile
765                 770                 775                 780 ccc ttg aaa gac aag acg ctg att gag aaa gag aga ttc tat gaa agc    2463
Pro Leu Lys Asp Lys Thr Leu Ile Glu Lys Glu Arg Phe Tyr Glu Ser
                785                 790                 795 cgg tgc agg cca gtg aca cca tca tgt aag gag ctg gct gac ctc atg    2511
Arg Cys Arg Pro Val Thr Pro Ser Cys Lys Glu Leu Ala Asp Leu Met
            800                 805                 810 acc cgc tgc atg aac tat gac ccc aat cag agg cct ttc ttc cga gcc    2559
Thr Arg Cys Met Asn Tyr Asp Pro Asn Gln Arg Pro Phe Phe Arg Ala
        815                 820                 825 atc atg aga gac att aat aag ctt gaa gag cag aat cca gat att gtt    2607
Ile Met Arg Asp Ile Asn Lys Leu Glu Glu Gln Asn Pro Asp Ile Val
    830                 835                 840 tcc aga aaa aaa aac cag cca act gaa gtg gac ccc aca cat ttt gag    2655
Ser Arg Lys Lys Asn Gln Pro Thr Glu Val Asp Pro Thr His Phe Glu
845                 850                 855                 860 aag cgc ttc cta aag agg atc cgt gac ttg gga gag ggc cac ttt ggg    2703
Lys Arg Phe Leu Lys Arg Ile Arg Asp Leu Gly Glu Gly His Phe Gly
                865                 870                 875 aag gtt gag ctc tgc agg tat gac ccc gaa gac aat aca ggg gag cag    2751
Lys Val Glu Leu Cys Arg Tyr Asp Pro Glu Asp Asn Thr Gly Glu Gln
            880                 885                 890 gtg gct gtt aaa tct ctg aag cct gag agt gga ggt aac cac ata gct    2799
Val Ala Val Lys Ser Leu Lys Pro Glu Ser Gly Gly Asn His Ile Ala
        895                 900                 905 gat ctg aaa aag gaa atc gag atc tta agg aac ctc tat cat gag aac    2847
Asp Leu Lys Lys Glu Ile Glu Ile Leu Arg Asn Leu Tyr His Glu Asn
    910                 915                 920 att gtg aag tac aaa gga atc tgc aca gaa gac gga gga aat ggt att    2895
Ile Val Lys Tyr Lys Gly Ile Cys Thr Glu Asp Gly Gly Asn Gly Ile
925                 930                 935                 940
```

-continued

```
aag ctc atc atg gaa ttt ctg cct tcg gga agc ctt aag gaa tat ctt    2943
Lys Leu Ile Met Glu Phe Leu Pro Ser Gly Ser Leu Lys Glu Tyr Leu
            945                 950                 955 cca aag aat aag aac aaa ata aac ctc aaa cag cag cta aaa tat gcc    2991
Pro Lys Asn Lys Asn Lys Ile Asn Leu Lys Gln Gln Leu Lys Tyr Ala
        960                 965                 970 gtt cag att tgt aag ggg atg gac tat ttg ggt tct cgg caa tac gtt    3039
Val Gln Ile Cys Lys Gly Met Asp Tyr Leu Gly Ser Arg Gln Tyr Val
    975                 980                 985 cac cgg gac ttg gca gca aga aat gtc ctt gtt gag agt gaa cac caa    3087
His Arg Asp Leu Ala Ala Arg Asn Val Leu Val Glu Ser Glu His Gln
990                 995                 1000 gtg aaa att gga gac ttc ggt tta acc aaa gca att gaa acc gat        3132
Val Lys Ile Gly Asp Phe Gly Leu Thr Lys Ala Ile Glu Thr Asp
1005                1010                1015 aag gag tat tac acc gtc aag gat gac cgg gac agc cct gtg ttt        3177
Lys Glu Tyr Tyr Thr Val Lys Asp Asp Arg Asp Ser Pro Val Phe
1020                1025                1030 tgg tat gct cca gaa tgt tta atg caa tct aaa ttt tat att gcc        3222
Trp Tyr Ala Pro Glu Cys Leu Met Gln Ser Lys Phe Tyr Ile Ala
1035                1040                1045 tct gac gtc tgg tct ttt gga gtc act ctg cat gag ctg ctg act        3267
Ser Asp Val Trp Ser Phe Gly Val Thr Leu His Glu Leu Leu Thr
1050                1055                1060 tac tgt gat tca gat tct agt ccc atg gct ttg ttc ctg aaa atg        3312
Tyr Cys Asp Ser Asp Ser Ser Pro Met Ala Leu Phe Leu Lys Met
1065                1070                1075 ata ggc cca acc cat ggc cag atg aca gtc aca aga ctt gtg aat        3357
Ile Gly Pro Thr His Gly Gln Met Thr Val Thr Arg Leu Val Asn
1080                1085                1090 acg tta aaa gaa gga aaa cgc ctg ccg tgc cca cct aac tgt cca        3402
Thr Leu Lys Glu Gly Lys Arg Leu Pro Cys Pro Pro Asn Cys Pro
1095                1100                1105 gat gag gtt tat cag ctt atg aga aaa tgc tgg gaa ttc caa cca        3447
Asp Glu Val Tyr Gln Leu Met Arg Lys Cys Trp Glu Phe Gln Pro
1110                1115                1120 tcc aat cgg aca agc ttt cag aac ctt att gaa gga ttt gaa gca        3492
Ser Asn Arg Thr Ser Phe Gln Asn Leu Ile Glu Gly Phe Glu Ala
1125                1130                1135 ctt tta aaa taa gaagcatgaa taacatttaa attccacaga ttatcaa           3541
Leu Leu Lys
1140

<210> SEQ ID NO 4
<211> LENGTH: 1142
<212> TYPE: PRT
<213> ORGANISM: Homo sapiens

<400> SEQUENCE: 4

Met Ala Phe Cys Ala Lys Met Arg Ser Ser Lys Lys Thr Glu Val Asn
  1               5                  10                  15

Leu Glu Ala Pro Glu Pro Gly Val Glu Val Ile Phe Tyr Leu Ser Asp
                 20                  25                  30

Arg Glu Pro Leu Arg Leu Gly Ser Gly Glu Tyr Thr Ala Glu Glu Leu
             35                  40                  45

Cys Ile Arg Ala Ala Gln Ala Cys Arg Ile Ser Pro Leu Cys His Asn
         50                  55                  60

Leu Phe Ala Leu Tyr Asp Glu Asn Thr Lys Leu Trp Tyr Ala Pro Asn
 65                  70                  75                  80

Arg Thr Ile Thr Val Asp Asp Lys Met Ser Leu Arg Leu His Tyr Arg
```

-continued

```
                    85                  90                  95
Met Arg Phe Tyr Phe Thr Asn Trp His Gly Thr Asn Asp Asn Glu Gln
                100                 105                 110

Ser Val Trp Arg His Ser Pro Lys Lys Gln Lys Asn Gly Tyr Glu Lys
                115                 120                 125

Lys Lys Ile Pro Asp Ala Thr Pro Leu Leu Asp Ala Ser Ser Leu Glu
                130                 135                 140

Tyr Leu Phe Ala Gln Gly Gln Tyr Asp Leu Val Lys Cys Leu Ala Pro
145                 150                 155                 160

Ile Arg Asp Pro Lys Thr Glu Gln Asp Gly His Asp Ile Glu Asn Glu
                165                 170                 175

Cys Leu Gly Met Ala Val Leu Ala Ile Ser His Tyr Ala Met Met Lys
                180                 185                 190

Lys Met Gln Leu Pro Glu Leu Pro Lys Asp Ile Ser Tyr Lys Arg Tyr
                195                 200                 205

Ile Pro Glu Thr Leu Asn Lys Ser Ile Arg Gln Arg Asn Leu Leu Thr
                210                 215                 220

Arg Met Arg Ile Asn Asn Val Phe Lys Asp Phe Leu Lys Glu Phe Asn
225                 230                 235                 240

Asn Lys Thr Ile Cys Asp Ser Ser Val Ser Thr His Asp Leu Lys Val
                245                 250                 255

Lys Tyr Leu Ala Thr Leu Glu Thr Leu Thr Lys His Tyr Gly Ala Glu
                260                 265                 270

Ile Phe Glu Thr Ser Met Leu Leu Ile Ser Ser Glu Asn Glu Met Asn
                275                 280                 285

Trp Phe His Ser Asn Asp Gly Gly Asn Val Leu Tyr Tyr Glu Val Met
                290                 295                 300

Val Thr Gly Asn Leu Gly Ile Gln Trp Arg His Lys Pro Asn Val Val
305                 310                 315                 320

Ser Val Glu Lys Glu Lys Asn Lys Leu Lys Arg Lys Lys Leu Glu Asn
                325                 330                 335

Lys Asp Lys Lys Asp Glu Glu Lys Asn Lys Ile Arg Glu Glu Trp Asn
                340                 345                 350

Asn Phe Ser Phe Phe Pro Glu Ile Thr His Ile Val Ile Lys Glu Ser
                355                 360                 365

Val Val Ser Ile Asn Lys Gln Asp Asn Lys Lys Met Glu Leu Lys Leu
                370                 375                 380

Ser Ser His Glu Glu Ala Leu Ser Phe Val Ser Leu Val Asp Gly Tyr
385                 390                 395                 400

Phe Arg Leu Thr Ala Asp Ala His His Tyr Leu Cys Thr Asp Val Ala
                405                 410                 415

Pro Pro Leu Ile Val His Asn Ile Gln Asn Gly Cys His Gly Pro Ile
                420                 425                 430

Cys Thr Glu Tyr Ala Ile Asn Lys Leu Arg Gln Glu Gly Ser Glu Glu
                435                 440                 445

Gly Met Tyr Val Leu Arg Trp Ser Cys Thr Asp Phe Asp Asn Ile Leu
450                 455                 460

Met Thr Val Thr Cys Phe Glu Lys Ser Glu Gln Val Gln Gly Ala Gln
465                 470                 475                 480

Lys Gln Phe Lys Asn Phe Gln Ile Glu Val Gln Lys Gly Arg Tyr Ser
                485                 490                 495

Leu His Gly Ser Asp Arg Ser Phe Pro Ser Leu Gly Asp Leu Met Ser
                500                 505                 510
```

-continued

His Leu Lys Lys Gln Ile Leu Arg Thr Asp Asn Ile Ser Phe Met Leu
    515                 520                 525

Lys Arg Cys Cys Gln Pro Lys Pro Arg Glu Ile Ser Asn Leu Leu Val
530                 535                 540

Ala Thr Lys Lys Ala Gln Glu Trp Gln Pro Val Tyr Pro Met Ser Gln
545                 550                 555                 560

Leu Ser Phe Asp Arg Ile Leu Lys Lys Asp Leu Val Gln Gly Glu His
                565                 570                 575

Leu Gly Arg Gly Thr Arg Thr His Ile Tyr Ser Gly Thr Leu Met Asp
            580                 585                 590

Tyr Lys Asp Asp Glu Gly Thr Ser Glu Glu Lys Lys Ile Lys Val Ile
        595                 600                 605

Leu Lys Val Leu Asp Pro Ser His Arg Asp Ile Ser Leu Ala Phe Phe
    610                 615                 620

Glu Ala Ala Ser Met Met Arg Gln Val Ser His Lys His Ile Val Tyr
625                 630                 635                 640

Leu Tyr Gly Val Cys Val Arg Asp Val Glu Asn Ile Met Val Glu Glu
                645                 650                 655

Phe Val Glu Gly Gly Pro Leu Asp Leu Phe Met His Arg Lys Ser Asp
            660                 665                 670

Val Leu Thr Thr Pro Trp Lys Phe Lys Val Ala Lys Gln Leu Ala Ser
        675                 680                 685

Ala Leu Ser Tyr Leu Glu Asp Lys Asp Leu Val His Gly Asn Val Cys
    690                 695                 700

Thr Lys Asn Leu Leu Leu Ala Arg Glu Gly Ile Asp Ser Glu Cys Gly
705                 710                 715                 720

Pro Phe Ile Lys Leu Ser Asp Pro Gly Ile Pro Ile Thr Val Leu Ser
                725                 730                 735

Arg Gln Glu Cys Ile Glu Arg Ile Pro Trp Ile Ala Pro Glu Cys Val
            740                 745                 750

Glu Asp Ser Lys Asn Leu Ser Val Ala Ala Asp Lys Trp Ser Phe Gly
        755                 760                 765

Thr Thr Leu Trp Glu Ile Cys Tyr Asn Gly Glu Ile Pro Leu Lys Asp
    770                 775                 780

Lys Thr Leu Ile Glu Lys Glu Arg Phe Tyr Glu Ser Arg Cys Arg Pro
785                 790                 795                 800

Val Thr Pro Ser Cys Lys Glu Leu Ala Asp Leu Met Thr Arg Cys Met
                805                 810                 815

Asn Tyr Asp Pro Asn Gln Arg Pro Phe Phe Arg Ala Ile Met Arg Asp
            820                 825                 830

Ile Asn Lys Leu Glu Glu Gln Asn Pro Asp Ile Val Ser Arg Lys Lys
        835                 840                 845

Asn Gln Pro Thr Glu Val Asp Pro Thr His Phe Glu Lys Arg Phe Leu
    850                 855                 860

Lys Arg Ile Arg Asp Leu Gly Glu Gly His Phe Gly Lys Val Glu Leu
865                 870                 875                 880

Cys Arg Tyr Asp Pro Glu Asp Asn Thr Gly Glu Gln Val Ala Val Lys
                885                 890                 895

Ser Leu Lys Pro Glu Ser Gly Gly Asn His Ile Ala Asp Leu Lys Lys
            900                 905                 910

Glu Ile Glu Ile Leu Arg Asn Leu Tyr His Glu Asn Ile Val Lys Tyr
        915                 920                 925

Lys Gly Ile Cys Thr Glu Asp Gly Gly Asn Gly Ile Lys Leu Ile Met
    930                 935                 940

```
Glu Phe Leu Pro Ser Gly Ser Leu Lys Glu Tyr Leu Pro Lys Asn Lys
945                 950                 955                 960

Asn Lys Ile Asn Leu Lys Gln Gln Leu Lys Tyr Ala Val Gln Ile Cys
            965                 970                 975

Lys Gly Met Asp Tyr Leu Gly Ser Arg Gln Tyr Val His Arg Asp Leu
        980                 985                 990

Ala Ala Arg Asn Val Leu Val Glu  Ser Glu His Gln Val  Lys Ile Gly
        995                 1000                 1005

Asp Phe Gly Leu Thr Lys Ala  Ile Glu Thr Asp Lys  Glu Tyr Tyr
1010                1015                1020

Thr Val Lys Asp Asp Arg Asp  Ser Pro Val Phe Trp  Tyr Ala Pro
1025                1030                1035

Glu Cys Leu Met Gln Ser Lys  Phe Tyr Ile Ala Ser  Asp Val Trp
1040                1045                1050

Ser Phe Gly Val Thr Leu His  Glu Leu Leu Thr Tyr  Cys Asp Ser
1055                1060                1065

Asp Ser Ser Pro Met Ala Leu  Phe Leu Lys Met Ile  Gly Pro Thr
1070                1075                1080

His Gly Gln Met Thr Val Thr  Arg Leu Val Asn Thr  Leu Lys Glu
1085                1090                1095

Gly Lys Arg Leu Pro Cys Pro  Pro Asn Cys Pro Asp  Glu Val Tyr
1100                1105                1110

Gln Leu Met Arg Lys Cys Trp  Glu Phe Gln Pro Ser  Asn Arg Thr
1115                1120                1125

Ser Phe Gln Asn Leu Ile Glu  Gly Phe Glu Ala Leu  Leu Lys
1130                1135                1140

<210> SEQ ID NO 5
<211> LENGTH: 4157
<212> TYPE: DNA
<213> ORGANISM: Homo sapiens
<220> FEATURE:
<221> NAME/KEY: CDS
<222> LOCATION: (352)..(2604)

<400> SEQUENCE: 5
agcggggcgg ggcgccagcg ctgccttttc tcctgccggg tagtttcgct ttcctgcgca      60
gagtctgcgg aggggctcgg ctgcaccggg gggatcgcgc ctggcagacc ccagaccgag     120
cagaggcgac ccagcgcgct cgggagaggc tgcaccgccg cgccccgcc tagcccttcc     180 ggatcctgcg cgcagaaaag tttcatttgc tgtatgccat cctcgagagc tgtctaggtt     240
aacgttcgca ctctgtgtat ataacctcga cagtcttggc acctaacgtg ctgtgcgtag     300
ctgctccttt ggttgaatcc ccaggccctt gttggggcac aaggtggcag g atg tct     357
                                                         Met Ser
                                                           1 cag tgg tac gaa ctt cag cag ctt gac tca aaa ttc ctg gag cag gtt      405
Gln Trp Tyr Glu Leu Gln Gln Leu Asp Ser Lys Phe Leu Glu Gln Val
        5                   10                  15 cac cag ctt tat gat gac agt ttt ccc atg gaa atc aga cag tac ctg      453
His Gln Leu Tyr Asp Asp Ser Phe Pro Met Glu Ile Arg Gln Tyr Leu
    20                  25                  30 gca cag tgg tta gaa aag caa gac tgg gag cac gct gcc aat gat gtt      501
Ala Gln Trp Leu Glu Lys Gln Asp Trp Glu His Ala Ala Asn Asp Val
35                  40                  45                  50 tca ttt gcc acc atc cgt ttt cat gac ctc ctg tca cag ctg gat gat      549
Ser Phe Ala Thr Ile Arg Phe His Asp Leu Leu Ser Gln Leu Asp Asp
            55                  60                  65
```

```
caa tat agt cgc ttt tct ttg gag aat aac ttc ttg cta cag cat aac    597
Gln Tyr Ser Arg Phe Ser Leu Glu Asn Asn Phe Leu Leu Gln His Asn
         70                  75                  80 ata agg aaa agc aag cgt aat ctt cag gat aat ttt cag gaa gac cca    645
Ile Arg Lys Ser Lys Arg Asn Leu Gln Asp Asn Phe Gln Glu Asp Pro
     85                  90                  95 atc cag atg tct atg atc att tac agc tgt ctg aag gaa gaa agg aaa    693
Ile Gln Met Ser Met Ile Ile Tyr Ser Cys Leu Lys Glu Glu Arg Lys
100                 105                 110 att ctg gaa aac gcc cag aga ttt aat cag gct cag tcg ggg aat att    741
Ile Leu Glu Asn Ala Gln Arg Phe Asn Gln Ala Gln Ser Gly Asn Ile
115                 120                 125                 130 cag agc aca gtg atg tta gac aaa cag aaa gag ctt gac agt aaa gtc    789
Gln Ser Thr Val Met Leu Asp Lys Gln Lys Glu Leu Asp Ser Lys Val
         135                 140                 145 aga aat gtg aag gac aag gtt atg tgt ata gag cat gaa atc aag agc    837
Arg Asn Val Lys Asp Lys Val Met Cys Ile Glu His Glu Ile Lys Ser
        150                 155                 160 ctg gaa gat tta caa gat gaa tat gac ttc aaa tgc aaa acc ttg cag    885
Leu Glu Asp Leu Gln Asp Glu Tyr Asp Phe Lys Cys Lys Thr Leu Gln
        165                 170                 175 aac aga gaa cac gag acc aat ggt gtg gca aag agt gat cag aaa caa    933
Asn Arg Glu His Glu Thr Asn Gly Val Ala Lys Ser Asp Gln Lys Gln
    180                 185                 190 gaa cag ctg tta ctc aag aag atg tat tta atg ctt gac aat aag aga    981
Glu Gln Leu Leu Leu Lys Lys Met Tyr Leu Met Leu Asp Asn Lys Arg
195                 200                 205                 210 aag gaa gta gtt cac aaa ata ata gag ttg ctg aat gtc act gaa ctt   1029
Lys Glu Val Val His Lys Ile Ile Glu Leu Leu Asn Val Thr Glu Leu
        215                 220                 225 acc cag aat gcc ctg att aat gat gaa cta gtg gag tgg aag cgg aga   1077
Thr Gln Asn Ala Leu Ile Asn Asp Glu Leu Val Glu Trp Lys Arg Arg
        230                 235                 240 cag cag agc gcc tgt att ggg ggg ccg ccc aat gct tgc ttg gat cag   1125
Gln Gln Ser Ala Cys Ile Gly Gly Pro Pro Asn Ala Cys Leu Asp Gln
        245                 250                 255 ctg cag aac tgg ttc act ata gtt gcg gag agt ctg cag caa gtt cgg   1173
Leu Gln Asn Trp Phe Thr Ile Val Ala Glu Ser Leu Gln Gln Val Arg
        260                 265                 270 cag cag ctt aaa aag ttg gag gaa ttg gaa cag aaa tac acc tac gaa   1221
Gln Gln Leu Lys Lys Leu Glu Glu Leu Glu Gln Lys Tyr Thr Tyr Glu
275                 280                 285                 290 cat gac cct atc aca aaa aac aaa caa gtg tta tgg gac cgc acc ttc   1269
His Asp Pro Ile Thr Lys Asn Lys Gln Val Leu Trp Asp Arg Thr Phe
                295                 300                 305 agt ctt ttc cag cag ctc att cag agc tcg ttt gtg gtg gaa aga cag   1317
Ser Leu Phe Gln Gln Leu Ile Gln Ser Ser Phe Val Val Glu Arg Gln
        310                 315                 320 ccc tgc atg cca acg cac cct cag agg ccg ctg gtc ttg aag aca ggg   1365
Pro Cys Met Pro Thr His Pro Gln Arg Pro Leu Val Leu Lys Thr Gly
        325                 330                 335 gtc cag ttc act gtg aag ttg aga ctg ttg gtg aaa ttg caa gag ctg   1413
Val Gln Phe Thr Val Lys Leu Arg Leu Leu Val Lys Leu Gln Glu Leu
        340                 345                 350 aat tat aat ttg aaa gtc aaa gtc tta ttt gat aaa gat gtg aat gag   1461
Asn Tyr Asn Leu Lys Val Lys Val Leu Phe Asp Lys Asp Val Asn Glu
355                 360                 365                 370 aga aat aca gta aaa gga ttt agg aag ttc aac att ttg ggc acg cac   1509
Arg Asn Thr Val Lys Gly Phe Arg Lys Phe Asn Ile Leu Gly Thr His
                375                 380                 385
```

```
aca aaa gtg atg aac atg gag gag tcc acc aat ggc agt ctg gcg gct    1557
Thr Lys Val Met Asn Met Glu Glu Ser Thr Asn Gly Ser Leu Ala Ala
        390                 395                 400 gaa ttt cgg cac ctg caa ttg aaa gaa cag aaa aat gct ggc acc aga    1605
Glu Phe Arg His Leu Gln Leu Lys Glu Gln Lys Asn Ala Gly Thr Arg
    405                 410                 415 acg aat gag ggt cct ctc atc gtt act gaa gag ctt cac tcc ctt agt    1653
Thr Asn Glu Gly Pro Leu Ile Val Thr Glu Glu Leu His Ser Leu Ser
420                 425                 430 ttt gaa acc caa ttg tgc cag cct ggt ttg gta att gac ctc gag acg    1701
Phe Glu Thr Gln Leu Cys Gln Pro Gly Leu Val Ile Asp Leu Glu Thr
435                 440                 445                 450 acc tct ctg ccc gtt gtg gtg atc tcc aac gtc agc cag ctc ccg agc    1749
Thr Ser Leu Pro Val Val Val Ile Ser Asn Val Ser Gln Leu Pro Ser
            455                 460                 465 ggt tgg gcc tcc atc ctt tgg tac aac atg ctg gtg gcg gaa ccc agg    1797
Gly Trp Ala Ser Ile Leu Trp Tyr Asn Met Leu Val Ala Glu Pro Arg
        470                 475                 480 aat ctg tcc ttc ttc ctg act cca cca tgt gca cga tgg gct cag ctt    1845
Asn Leu Ser Phe Phe Leu Thr Pro Pro Cys Ala Arg Trp Ala Gln Leu
    485                 490                 495 tca gaa gtg ctg agt tgg cag ttt tct tct gtc acc aaa aga ggt ctc    1893
Ser Glu Val Leu Ser Trp Gln Phe Ser Ser Val Thr Lys Arg Gly Leu
500                 505                 510 aat gtg gac cag ctg aac atg ttg gga gag aag ctt ctt ggt cct aac    1941
Asn Val Asp Gln Leu Asn Met Leu Gly Glu Lys Leu Leu Gly Pro Asn
515                 520                 525                 530 gcc agc ccc gat ggt ctc att ccg tgg acg agg ttt tgt aag gaa aat    1989
Ala Ser Pro Asp Gly Leu Ile Pro Trp Thr Arg Phe Cys Lys Glu Asn
            535                 540                 545 ata aat gat aaa aat ttt ccc ttc tgg ctt tgg att gaa agc atc cta    2037
Ile Asn Asp Lys Asn Phe Pro Phe Trp Leu Trp Ile Glu Ser Ile Leu
        550                 555                 560 gaa ctc att aaa aaa cac ctg ctc cct ctc tgg aat gat ggg tgc atc    2085
Glu Leu Ile Lys Lys His Leu Leu Pro Leu Trp Asn Asp Gly Cys Ile
    565                 570                 575 atg ggc ttc atc agc aag gag cga gag cgt gcc ctg ttg aag gac cag    2133
Met Gly Phe Ile Ser Lys Glu Arg Glu Arg Ala Leu Leu Lys Asp Gln
580                 585                 590 cag ccg ggg acc ttc ctg ctg cgg ttc agt gag agc tcc cgg gaa ggg    2181
Gln Pro Gly Thr Phe Leu Leu Arg Phe Ser Glu Ser Ser Arg Glu Gly
595                 600                 605                 610 gcc atc aca ttc aca tgg gtg gag cgg tcc cag aac gga ggc gaa cct    2229
Ala Ile Thr Phe Thr Trp Val Glu Arg Ser Gln Asn Gly Gly Glu Pro
            615                 620                 625 gac ttc cat gcg gtt gaa ccc tac acg aag aaa gaa ctt tct gct gtt    2277
Asp Phe His Ala Val Glu Pro Tyr Thr Lys Lys Glu Leu Ser Ala Val
        630                 635                 640 act ttc cct gac atc att cgc aat tac aaa gtc atg gct gct gag aat    2325
Thr Phe Pro Asp Ile Ile Arg Asn Tyr Lys Val Met Ala Ala Glu Asn
    645                 650                 655 att cct gag aat ccc ctg aag tat ctg tat cca aat att gac aaa gac    2373
Ile Pro Glu Asn Pro Leu Lys Tyr Leu Tyr Pro Asn Ile Asp Lys Asp
660                 665                 670 cat gcc ttt gga aag tat tac tcc agg cca aag gaa gca cca gag cca    2421
His Ala Phe Gly Lys Tyr Tyr Ser Arg Pro Lys Glu Ala Pro Glu Pro
675                 680                 685                 690 atg gaa ctt gat ggc cct aaa gga act gga tat atc aag act gag ttg    2469
Met Glu Leu Asp Gly Pro Lys Gly Thr Gly Tyr Ile Lys Thr Glu Leu
            695                 700                 705
```

```
att tct gtg tct gaa gtt cac cct tct aga ctt cag acc aca gac aac    2517
Ile Ser Val Ser Glu Val His Pro Ser Arg Leu Gln Thr Thr Asp Asn
            710                 715                 720 ctg ctc ccc atg tct cct gag gag ttt gac gag gtg tct cgg ata gtg    2565
Leu Leu Pro Met Ser Pro Glu Glu Phe Asp Glu Val Ser Arg Ile Val
        725                 730                 735 ggc tct gta gaa ttc gac agt atg atg aac aca gta tag agcatgaatt     2614
Gly Ser Val Glu Phe Asp Ser Met Met Asn Thr Val
    740                 745                 750 ttttcatct tctctggcga cagttttcct tctcatctgt gattccctcc tgctactctg    2674
ttccttcaca tcctgtgttt ctagggaaat gaaagaaagg ccagcaaatt cgctgcaacc    2734
tgttgatagc aagtgaattt ttctctaact cagaaacatc agttactctg aagggcatca    2794
tgcatcttac tgaaggtaaa attgaaaggc attctctgaa gagtgggttt cacaagtgaa    2854
aaacatccag atacacccaa agtatcagga cgagaatgag ggtcctttgg gaaaggagaa    2914
gttaagcaac atctagcaaa tgttatgcat aaagtcagtg cccaactgtt ataggttgtt    2974
ggataaatca gtggttattt agggaactgc ttgacgtagg aacggtaaat ttctgtggga    3034
gaattcttac atgttttctt tgctttaagt gtaactggca gttttccatt ggtttacctg    3094
tgaaatagtt caaagccaag tttatataca attatatcag tcctctttca aggtagccca    3154
tcatggatct ggtaggggga aaatgtgtat tttattacat ctttcacatt ggctatttaa    3214
agacaaagac aaattctgtt tcttgagaag agaatattag ctttactgtt tgttatggct    3274
taatgacact agctaatatc aatagaagga tgtacatttc caattcaca agttgtgttt    3334
gatatccaaa gctgaataca ttctgctttc atcttggtca catacaatta ttttacagt    3394
tctcccaagg gagttaggct attcacaacc actcattcaa aagttgaaat taaccataga    3454
tgtagataaa ctcagaaatt taattcatgt ttcttaaatg ggctactttg tccttttgt     3514
tattagggtg gtatttagtc tattagccac aaaattggga aaggagtaga aaaagcagta    3574
actgacaact tgaataatac accagagata atatgagaat cagatcattt caaaactcat    3634
ttcctatgta actgcattga gaactgcata tgtttcgctg atatatgtgt ttttcacatt    3694
tgcgaatggt tccattctct ctcctgtact ttttccagac acttttttga gtggatgatg    3754
tttcgtgaag tatactgtat ttttaccttt tccttccttt atcactgaca caaaaagtag    3814
attaagagat gggtttgaca aggttcttcc cttttacata ctgctgtcta tgtggctgta    3874
tcttgttttt ccactactgc taccacaact atattatcat gcaaatgctg tattcttctt    3934
tggtggagat aaagatttct tgagttttgt tttaaaatta aagctaaagt atctgtattg    3994
cattaaatat aatatgcaca cagtgctttc cgtggcactg catacaatct gaggcctcct    4054
ctctcagttt ttatatagat ggcgagaacc taagtttcag ttgattttac aattgaaatg    4114
actaaaaaac aaagaagaca acattaaaac aatattgttt cta                     4157
```

<210> SEQ ID NO 6
<211> LENGTH: 750
<212> TYPE: PRT
<213> ORGANISM: Homo sapiens

<400> SEQUENCE: 6

Met Ser Gln Trp Tyr Glu Leu Gln Gln Leu Asp Ser Lys Phe Leu Glu
  1               5                  10                  15

Gln Val His Gln Leu Tyr Asp Asp Ser Phe Pro Met Glu Ile Arg Gln
             20                  25                  30

Tyr Leu Ala Gln Trp Leu Glu Lys Gln Asp Trp Glu His Ala Ala Asn

```
                35              40              45
Asp Val Ser Phe Ala Thr Ile Arg Phe His Asp Leu Leu Ser Gln Leu
             50                  55                  60

Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
                 85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
        355                 360                 365

Asn Glu Arg Asn Thr Val Lys Gly Phe Arg Lys Phe Asn Ile Leu Gly
    370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
        435                 440                 445

Glu Thr Thr Ser Leu Pro Val Val Val Ile Ser Asn Val Ser Gln Leu
450                 455                 460
```

```
Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Cys Ala Arg Trp Ala
            485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
            515                 520                 525

Pro Asn Ala Ser Pro Asp Gly Leu Ile Pro Trp Thr Arg Phe Cys Lys
            530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
            565                 570                 575

Cys Ile Met Gly Phe Ile Ser Lys Glu Arg Glu Arg Ala Leu Leu Lys
            580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
            610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
            645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
            675                 680                 685

Glu Pro Met Glu Leu Asp Gly Pro Lys Gly Thr Gly Tyr Ile Lys Thr
            690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
            725                 730                 735

Ile Val Gly Ser Val Glu Phe Asp Ser Met Met Asn Thr Val
            740                 745                 750

<210> SEQ ID NO 7
<211> LENGTH: 593
<212> TYPE: DNA
<213> ORGANISM: Homo sapiens

<400> SEQUENCE: 7
tggcactcgg acgccgtccc ggtcccggcc gggcctggga ctctccgcgc ccgctgggg      60 cctgaagctc cgggtaccgc cgagtcctcc cctactggcg gctgggggag gaacgaggg    120 cggggctctc ggaaagtccc aggaacaggc tgatcctgcg ctggcgagaa gctcagccat   180
ttaggggaaa gcgaaatcga aagcggccgc ctgctcacta gataacgcct acttccaaaa   240
gtggcctgcc cagactattt tggtagcaag cgtggaaatc agatctgaga atctcgggag   300
cagccctggt gcccaatttt ctccatcacg cacacccttc tcgcctctcc ctgcctcctg   360
cctttccact tgcaccagtt ttcccacccc agcctcaggg cggggctgcc tcgtcacttg   420
tctcggggca gatctgccct acacacgtta gcgccgcgcg caaagcagcc ccgcagcacc   480
caggcgcctc ctggcggcgc cgcgaagggg cggggctgtc ggctgcgcgt tgtgcgctgt   540
```

```
cccaggttgg aaaccagtgc cccaggcggc gaggagagcg gtgccttgca ggg        593

<210> SEQ ID NO 8
<211> LENGTH: 1680
<212> TYPE: DNA
<213> ORGANISM: Homo sapiens

<400> SEQUENCE: 8
gtgctcaccc ggcccggtgc cacccgggtc cacagggatg cgaaggagcg ggacaccatg    60
aaggaggacg gcggcgcgga gttctcggct cgctccagga agaggaaggc aaacgtgacc   120 gttttttgc aggatccaga tgaagaaatg gccaaaatcg acaggacggc gagggaccag   180
tgtgggagcc agccttggga caataatgca gtctgtgcag accoctgctc cctgatcccc   240 acacctgaca aagaagatga tgaccgggtt tacccaaact caacgtgcaa gcctcggatt   300
attgcaccat ccagaggctc cccgctgcct gtactgagct gggcaaatag agaggaagtc   360
tggaaaatca tgttaaacaa ggaaaagaca tacttaaggg atcagcactt tcttgagcaa   420
caccctcttc tgcagccaaa aatgcgagca attcttctgg attggttaat ggaggtgtgt   480
gaagtctata aacttcacag ggagaccttt tacttggcac aagatttctt tgaccggtat   540
atggcgacac aagaaaatgt tgtaaaaact cttttacagc ttattgggat ttcatcttta   600
tttattgcag ccaaacttga ggaaatctat cctccaaagt tgcaccagtt tgcgtatgtg   660
acagatggag cttgttcagg agatgaaatt ctcaccatgg aattaatgat tatgaaggcc   720
cttaagtggc gtttaagtcc cctgactatt gtgtcctggc tgaatgtata catgcaggtt   780
gcatatctaa atgacttaca tgaagtgcta ctgccgcagt atccccagca aatctttata   840
cagattgcag agctgttgga tctctgtgtc ctggatgttg actgccttga atttccttat   900
ggtatacttg ctgcttcggc cttgtatcat ttctcgtcat ctgaattgat gcaaaaggtt   960
tcagggtatc agtggtgcga catagagaac tgtgtcaagt ggatggttcc atttgccatg  1020
gttataaggg agacggggag ctcaaaactg aagcacttca ggggcgtcgc tgatgaagat  1080
gcacacaaca tacagaccca cagagacagc ttggatttgc tggacaaagc ccgagcaaag  1140
aaagccatgt tgtctgaaca aaatagggct tctcctctcc ccagtgggct cctcaccccg  1200
ccacagagcg gtaagaagca gagcagcggg ccggaaatgg cgtgaccacc ccatccttct  1260
ccaccaaaga cagttgcgcg cctgctccac gttctcttct gtctgttgca gcggaggcgt  1320
gcgtttgctt ttacagatat ctgaatggaa gagtgtttct tccacaacag aagtatttct  1380
gtggatggca tcaaacaggg caaagtgttt tttattgaat gcttataggt tttttttaaa  1440
taagtgggtc aagtacacca gccacctcca gacaccagtg cgtgctcccg atgctgctat  1500
ggaaggtgct acttgaccta aaggactccc acaacaacaa aagcttgaag ctgtggaggg  1560
ccacggtggc gtggctctcc tcgcaggtgt tctgggctcc gttgtaccaa gtggagcagg  1620
tggttgcggg caagcgttgt gcagagccca tagccagctg ggcaggggc tgccctctcc  1680
```

DETECTION OF UTERINE LEIOMYOSARCOMA USING LMP2

CROSS-REFERENCE TO RELATED APPLICATIONS

The present application is a 35 U.S.C. §371 National Stage patent application of International patent application PCT/JP2006/324403, filed on Nov. 30, 2006, which claims priority to Japanese patent application JP 2005-347227, filed on Nov. 30, 2005.

TECHNICAL FIELD

The present invention relates to a method for detecting uterine leiomyosarcoma using mutation of LMP2, cyclin E, and the JAK1 kinase gene, the STAT1 gene, and the LMP2 promoter associated with the interferon γ (IFN-γ) signal transduction cascade as markers and a method for differentiation of uterine leiomyoma from uterine leiomyosarcoma.

BACKGROUND ART

Uterine cancer is the most common type of gynecologic cancer. The frequency of uterine leiomyosarcoma development is low, and it accounts 2% to 5% of cases of uterine body cancer. Uterine leiomyosarcoma develops more often in the muscle layer of the uterine body than in the uterine cervix. The myometrium is composed of smooth muscle. Uterine leiomyoma is a benign tumor that develops in the myometrium, and uterine leiomyosarcoma is a malignant tumor. Differentiation of uterine leiomyoma from uterine leiomyosarcoma was very difficult. In general, tissue has been sampled via surgery, and whether or not a tumor was uterine leiomyoma or uterine leiomyosarcoma has been identified via microscopic cell analysis. Uterine leiomyosarcoma is highly atypical and often allows proliferation of tumor cells that occasionally become gigantic. In some cases, such tumors do not substantially show cellular atypism, and the presence or absence of cellular atypism would not serve as a definite discriminant. Uterine leiomyoma is differentiated from uterine leiomyosarcoma based on the occurrence of coagulative necrosis and the enlargement of an image representing cell division. When a cell density is high, in principle, a tumor is identified to be uterine leiomyosarcoma if 10 or more cell divisions are observed in a 10× wide-field view. The tumor is identified to be uterine leiomyosarcoma if 5 or more atypisms are observed in the tumor cell in a 10× wide-field view. In practice, uterine leiomyoma has been differentiated from uterine leiomyosarcoma based on the degree of cellular atypism, cell density, the number of cell divisions, tumor necrosis, and the bleeding of tumor. Such differentiation was mainly made by observing tissue morphology microscopically or visually. However, expert skills are required for such differentiation, and such differentiation is not always accurate.

In the past, the present inventors reported that uterine leiomyosarcoma was observed in 6-month or older female mice each lacking an immunoprotease component; i.e., low molecular mass polypeptide 2 (LMP2), and that the incidence thereof in 12-month-olds would account for about 35% of all LMP2-lacking female mice (see Van Kaer L. et al., 1994, Immunity, 1, 533-541 and Hayashi T. et al., 2002, Cancer Res., 62, 24-27). LMP2 functions in a tissue-specific manner and plays an essential role in MHC class I-mediated tumor rejection by CTLs (see Van Kaer L. et al., 1994, Immunity, 1, 533-541).

Thus, lack of LMP2 was deduced to serve as a factor for developing uterine leiomyosarcoma by means of certain functions. The 26S proteasome comprising LMP2, however, is involved in a complex manner with activation of a transcription regulator or a cell-cycle regulator, production of a peptide antigen of an MHC class I molecule, and the like, and a direct correlation between LMP2 and development of uterine leiomyosarcoma was unknown. The way that functions of the 26S proteasome would change and the way that transcription and expression of LMP2 would change upon development of uterine leiomyosarcoma were unknown.

DISCLOSURE OF THE INVENTION

The present invention provides a method for detecting the presence of uterine leiomyosarcoma using the LMP2 transcription or expression level in uterine smooth muscle tissue as an indicator and a detection reagent used therefor.

The present inventors stained living mice with anti-LMP2 in order to inspect LMP2 expression in the muscle layer. As a result, they discovered that LMP2 expression specific to myogenic tissue, such as smooth muscle, stripped muscle, or cardiac muscle, was observed and that the origin of the tumor cells observed in uterine smooth muscle layer of LMP2-lacking mice was thus a myogenic cell (i.e., the smooth muscle cell).

Further, the present inventors inspected the conditions of LMP2 expression in biopsy tissue or surgically-removed tissue of the normal uterine smooth muscle layer, human uterine leiomyoma, and human uterine leiomyosarcoma. As a result, they discovered that LMP2 expression levels were significantly lowered only in the case of a malignant tumor, i.e., uterine leiomyosarcoma.

Subsequently, the present inventors induced forced expression of LMP2 via gene recombination in the uterine leiomyosarcoma (SKN) cells in which no LMP2 expression was observed and examined the morphology of SKN cells, cell proliferative rate thereof, and the changes of fibronectin expression in SKN cells, for the purpose of examining whether or not lowered LMP2 expression levels were directly involved with genetic transformation (canceration) in uterine smooth muscle cells. As a result, they discovered that the configuration and cell proliferative rate of SKN cells became similar to those of normal uterine smooth muscle cells and that fibronectin expression was significantly induced.

Based on such new findings, the present inventors discovered that differentiation of uterine leiomyoma from uterine leiomyosarcoma would be possible with the use of LMP2 transcription or expression as an indicator and that uterine leiomyosarcoma could be treated via LMP2 expression.

Further, the present inventors focused on the correlation between cyclin E expression and uterine leiomyosarcoma, and they discovered that transcription and expression of cyclin E would be significantly elevated in uterine smooth muscle tissue depending on the malignancy of uterine leiomyosarcoma.

The present inventors also examined the correlation of a gene associated with the interferon γ (IFN-γ) signal transmission system involved in LMP2 expression and uterine leiomyosarcoma. As a result, they discovered that mutation had occurred in the signal transmission factor, i.e., JAK1 kinase, the STAT1-encoding gene, and the LMP2 promoter, in uterine leiomyosarcoma tissue cell, and they then discovered that detection of such mutation would enable determination of whether or not a subject is afflicted with uterine leiomyosarcoma and is at high risk of affliction with uterine leiomyosarcoma.

The present inventors have completed the present invention in such a manner.

Specifically, the present invention is as follows.

[1] A method for detecting uterine leiomyosarcoma using LMP2 as a marker.

[2] A method for detecting the presence of uterine leiomyosarcoma using the LMP2 transcription or expression level in uterine smooth muscle tissue as an indicator comprising assaying LMP2 transcription or expression in uterine smooth muscle tissue, and identifying the presence of uterine leiomyosarcoma when the LMP2 transcription or expression level is lower than that in normal uterine smooth muscle tissue.

[3] A method for differentiating whether or not a tumor in uterine smooth muscle is uterine leiomyoma or uterine leiomyosarcoma using the LMP2 transcription or expression level in uterine smooth muscle tissue as an indicator comprising assaying LMP2 transcription or expression in uterine smooth muscle tissue, and determining that the tumor is uterine leiomyosarcoma when the LMP2 transcription or expression level is lower than that in normal uterine smooth muscle tissue.

[4] A method for determining malignancy of uterine leiomyosarcoma using the LMP2 transcription or expression level in uterine smooth muscle tissue as an indicator comprising assaying LMP2 transcription or expression in uterine smooth muscle tissue, and determining that the tumor is malignant uterine leiomyosarcoma when the LMP2 transcription or expression level is lower than that in normal uterine smooth muscle tissue.

[5] The method according to any of [1] to [4], wherein LMP2 transcription in the sampled uterine smooth muscle tissue or cell is assayed via in situ hybridization.

[6] The method according to any of [1] to [4], wherein mRNA of LMP2 is extracted from the sampled uterine smooth muscle tissue or cell and subjected to RT-PCR or Northern blotting to assay LMP2 transcription.

[7] The method according to any of [1] to [4], wherein the sampled uterine smooth muscle tissue or cell is subjected to immunohistochemical staining or immunocytochemical staining to assay LMP2 expression.

[8] The method according to any of [1] to [4], wherein the LMP2 protein is extracted from the sampled uterine smooth muscle tissue or cell and subjected to immunoassay to assay LMP2 expression.

[9] The method for detecting the presence of uterine leiomyosarcoma according to [1], which further involves the use of myosin as a marker and the use of the LMP2 and myosin transcription or expression levels as an indicator, wherein the presence of uterine leiomyosarcoma is identified when the LMP2 transcription or expression level is lower than that in normal uterine smooth muscle tissue and the myosin transcription or expression level is higher than that in normal uterine smooth muscle tissue.

[10] A method for detecting uterine leiomyosarcoma using LMP-2 and cyclin E as markers.

[11] A method for detecting the presence of uterine leiomyosarcoma using the degree of transcription or expression of LMP2 and cyclin E in uterine smooth muscle tissue as an indicator comprising assaying transcription or expression of LMP2 and cyclin E in uterine smooth muscle tissue, and identifying the presence of uterine leiomyosarcoma when the LMP2 transcription or expression level is lower than that in normal uterine smooth muscle tissue and the cyclin E transcription or expression level is higher than that in normal uterine smooth muscle tissue.

[12] A method for differentiating whether or not a tumor in uterine smooth muscle is uterine leiomyoma or uterine leiomyosarcoma using the degree of transcription or expression of LMP2 and cyclin E in uterine smooth muscle tissue as an indicator comprising assaying transcription or expression of LMP2 and cyclin E in uterine smooth muscle tissue, and determining that the tumor is uterine leiomyosarcoma when the LMP2 transcription or expression level is lower than that in normal uterine smooth muscle tissue and the cyclin E transcription or expression level is higher than that in normal uterine smooth muscle tissue.

[13] A method for determining malignancy of uterine leiomyosarcoma using the degree of transcription or expression of LMP2 and cyclin E in uterine smooth muscle tissue as an indicator comprising assaying transcription or expression of LMP2 and cyclin E in uterine smooth muscle tissue, and determining that the tumor is malignant uterine leiomyosarcoma when the LMP2 transcription or expression level is lower than that in normal uterine smooth muscle tissue and the cyclin E transcription or expression level is higher than that in normal uterine smooth muscle tissue.

[14] The method according to any of [10] to [13], wherein the sampled uterine smooth muscle tissue or cell is subjected to in situ hybridization to assay transcription of LMP2 and cyclin E.

[15] The method according to any of [10] to [13], wherein mRNAs of LMP2 and cyclin E are extracted from the sampled uterine smooth muscle tissue or cell and subjected to RT-PCR or Northern blotting to assay transcription of LMP2 and cyclin E.

[16] The method according to any of [10] to [13], wherein the sampled uterine smooth muscle tissue or cell is subjected to immunohistochemical staining or immunocytochemical staining to assay expression of LMP2 and cyclin E.

[17] The method according to any of [10] to [13], wherein LMP2 and cyclin E proteins are extracted from the sampled uterine smooth muscle tissue or cell and subjected to immunoassay to assay expression of LMP2 and cyclin E.

[18] A detection reagent for detecting uterine leiomyosarcoma using LMP2 as a marker, which comprises at least an LMP2 gene fragment as a probe or primer.

[19] A detection reagent for detecting uterine leiomyosarcoma using LMP2 and cyclin E as markers, which comprises at least an LMP2 gene fragment and a cyclin E gene fragment as probes or primers.

[20] The detection reagent for detecting uterine leiomyosarcoma according to [18] or [19], which is used for in situ hybridization.

[21] The detection reagent for detecting uterine leiomyosarcoma using LMP2 and myosin as markers according to [18] or [20], which further comprises a myosin gene fragment as a probe or primer.

[22] The detection reagent for detecting uterine leiomyosarcoma using LMP2, cyclin E, and myosin as markers according to [19] or [20], which further comprises a myosin gene fragment as a probe or primer.

[23] A detection reagent for detecting uterine leiomyosarcoma using LMP2 as a marker, which comprises at least an anti-LMP2 antibody.

[24] A detection reagent for detecting uterine leiomyosarcoma using LMP2 and cyclin E as a markers, which comprises at least an anti-LMP2 antibody and an anti-cyclin E antibody.

[25] The detection reagent for detecting uterine leiomyosarcoma according to [23] or [24], which is used for immunohistochemical or immunocytochemical staining.

[26] The detection reagent for detecting uterine leiomyosarcoma using LMP2 and myosin as markers according to [23] or [25], which further comprises an anti-myosin antibody.

[27] The detection reagent for detecting uterine leiomyosarcoma using LMP2, cyclin E, and myosin as markers according to [24] or [25], which further comprises an anti-myosin antibody.

[28] An oligonucleotide comprising a partial sequence selected from the group consisting of a partial sequence of the JAK1 kinase gene comprising at least one of the mutation sites (A1) to (A6) below of the JAK1 kinase gene, and a partial sequence of the LMP2 promoter comprising at least one of the mutation sites (B1) to (B5) below of the LMP2 promoter or he oligonucleotide which is labeled, the oligonucleotide or labeled oligonucleotide comprising a 10-bp to 30-bp partial sequence or a sequence complementary thereto:
(A1) A2612A;
(A2) G2626A;
(A3) G2642T;
(A4) A2967C;
(A5) A2960C;
(A6) A2985T;
(B1) A210G;
(B2) C214T;
(B3) A216G;
(B4) A217G; and
(B5) G219A.

[29] The oligonucleotide or he oligonucleotide which is labeled according to [28], which is used as a probe.

[30] A substrate comprising the oligonucleotide or he oligonucleotide which is labeled according to [28] immobilized thereon.

[31] At least a pair of primer sets used for amplification of a DNA fragment comprising a mutation site selected from the group consisting of at least one of the mutation sites (A1) to (A6) below of the JAK1 kinase gene and at least one of the mutation sites (B1) to (B5) below of the LMP2 promoter, the pair of primer sets being used for amplification of a DNA fragment comprising 10- to 30-bp partial sequences located at sites closer to the 3' end and the 5' end of the mutation site:
(A1) A2612A;
(A2) G2626A;
(A3) G2642T ;
(A4) A2967C;
(A5) A2960C;
(A6) A2985T;
(B1) A210G;
(B2) C214T;
(B3) A216G;
(B4) A217G; and
(B5) G219A.

[32] A kit for detecting uterine leiomyosarcoma comprising the primer sets according to [31], the oligonucleotide or he oligonucleotide which is labeled according to [28] or [29], and the substrate according to [30].

[33] A method for detecting uterine leiomyosarcoma comprising: sampling uterine smooth muscle tissue or cell from an animal; detecting a mutation site selected from the group consisting of at least one of the mutation sites (A1) to (A6) below of the JAK1 kinase gene and at least one of the mutation sites (B1) to (B5) below of the LMP2 promoter from the sampled tissue or cell; and, when such mutation is present, determining that the animal is afflicted with or highly susceptible to uterine leiomyosarcoma based on the detection results:
(A1) A2612A;
(A2) G2626A;
(A3) G2642T;
(A4) A2967C;
(A5) A2960C;
(A6) A2985T;
(B1) A210G;
(B2) C214T;
(B3) A216G;
(B4) A217G; and
(B5) G219A.

[34] The method according to [33], wherein the mutation in the JAK1 kinase gene or the LMP2 primer is detected using the primer sets according to [31], the probe according to [28] or [29], or the substrate according to [30].

This description includes part or all of the contents as disclosed in the description and/or drawings of Japanese Patent Application No. 2005-347227, which is a priority document of the present application.

BRIEF DESCRIPTION OF THE DRAWINGS

FIG. 12 shows a summary of changes in morphology, cell proliferative rate, and fibronectin expression in each cell.

FIG. 14 shows LMP2 expression in uterine leiomyosarcoma, uterine leiomyoma, and leiomyosarcoma that had developed in other organs.

FIG. 16 shows mutations in a JAK1 kinase gene, a STAT1 gene, and a LMP2 promoter derived from uterine leiomyosarcoma tissue.

FIG. 17 shows mutations in a JAK1 kinase gene, a STAT1 gene, and a LMP2 promoter derived from uterine leiomyosarcoma tissue.

FIG. 18 shows the conditions of LMP2 expression in each tissue. In FIG. 18, "N" represents the number of tissue samples that were subjected to LMP2 expression assay.

FIG. 19 shows the number of colonies formed by SKN cell proliferation upon introduction of the pCEM9 vector (containing no LMP2 gene) or the pCEM9-LMP2 vector (containing LMP2 gene) and neomycin-selected vectors into cultured human uterine leiomyosarcoma cells (SKN cells). pCEM9 and pLMP2 DNA (1 μg each) were transfected into $2\times10^5$ DT or SKN cells, and the cells were selected in a growth medium containing 0.5 or 0.4 mg/ml G418.

FIG. 21 shows a summary of changes in morphology, cell proliferative rate, and fibronectin expression in each cell.

FIG. 23C is a photograph showing that the expression level of the LMP2 gene in colony #121 in cultured human uterine leiomyosarcoma cells (SKN cells) into which the pCEM9-LMP2 vector (containing the LMP2 gene) has been introduced is more significant than that in other SKN cells.

FIG. 24 shows that the expression level of cyclin E, which induces cell proliferation, is significantly lowered in SKN cells (colony #121) in which LMP2 is constitutively expressed as a result of microarray-based gene expression analysis.

BEST MODES FOR CARRYING OUT THE INVENTION

Figure 1A:
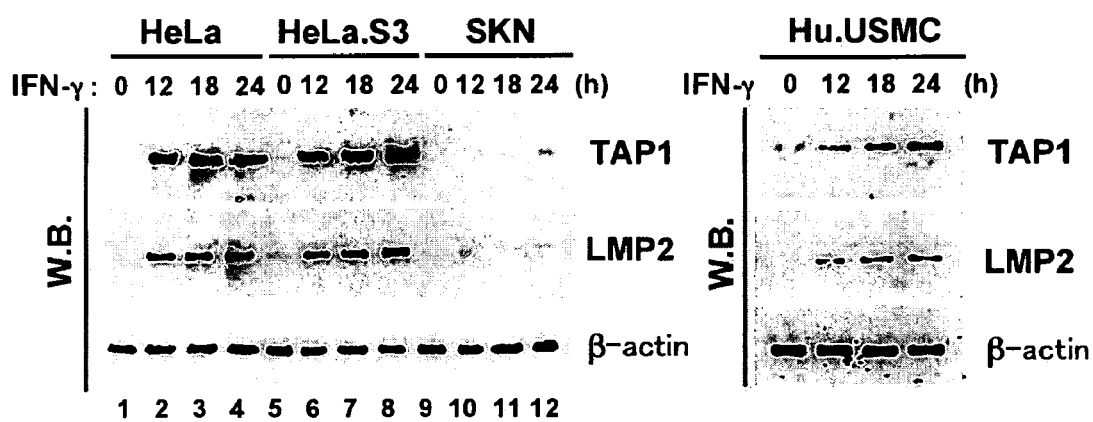
FIG. 1a is a photograph showing a lack of IFN-γ-induced TAP1 and LMP2 expression in SKN cells. A cytoplasm extract was prepared from the HeLa, HeLa.S3, SKN, and normal human uterine smooth muscle cells (Hu.USMC) processed with 250 units/ml of IFN-γ for the period of time as shown in the photograph, and 50 μg of the cytoplasm extract was separated via 10% SDS-PAGE. The TAP1, LMP2, and β-actin expression levels were assayed via immunoblot assay using an adequate antibody.

The present invention is intended to detect uterine leiomyosarcoma using LMP2 as a marker. The term "detect (or detection)" refers to, for example, determination of the presence of uterine leiomyosarcoma, determination of whether or not a patient is afflicted with uterine leiomyosarcoma, differentiation of whether or not a tumor in uterine smooth muscle is uterine leiomyoma or uterine leiomyosarcoma, and determination of malignancy of uterine leiomyosarcoma.

LMP2 is a proteasome subunit, and the method of the present invention is intended to detect whether or not LMP2 is transcribed or expressed in uterine smooth muscle layer. Inspection of LMP2 transcription or expression in the tissue of the human uterine smooth muscle layer reveals that LMP2 expression is positive in normal uterine smooth muscle layer and uterine leiomyoma (i.e., mild to potent expression levels). In contrast, LMP2 expression is negative in a major part of uterine leiomyosarcoma and weak expression is observed in some parts thereof. Accordingly, whether or not a patient is afflicted with uterine leiomyosarcoma or whether a tumor in uterine smooth muscle is uterine leiomyoma or uterine leiomyosarcoma can be evaluated using LMP2 transcription or expression as an indicator. In the case of a benign tumor (uterine leiomyoma), the level of LMP2 transcription or expression is strong. In the case of a malignant tumor (uterine leiomyosarcoma), however, the level of LMP2 transcription or expression is significantly weakened. This indicates that the level of LMP2 transcription or expression can serve as an indicator of malignancy of tumors observed in uterine smooth muscle cells.

Further, the present invention includes a method for detecting uterine leiomyosarcoma using cyclin E as a marker. Cyclin is a protein that plays an important role in the cell cycle that regulates activity of cyclin-dependent kinase. Cyclin E is a G1 cyclin that acts at the G1 stage in a mammalian cell. The expression level of cyclin E is more significantly elevated in uterine leiomyosarcoma tissue than in normal tissue, but it is not elevated in uterine leiomyoma tissue. In the present invention, whether or not cyclin E is transcribed or expressed in uterine smooth muscle layer is detected as in the case of LMP2. With the use of cyclin E transcription or expression as an indicator, whether or not a patient is afflicted with uterine leiomyosarcoma or whether a tumor in uterine smooth muscle is uterine leiomyoma or uterine leiomyosarcoma can be evaluated. In the case of a benign tumor (uterine leiomyoma), the level of cyclin E transcription or expression is not different from that in normal uterine smooth muscle tissue; however, the level of cyclin E transcription or expression is elevated in the case of a malignant tumor (i.e., uterine leiomyosarcoma). In general, cyclin E expression is not observed at the G2 stage or the M stage in normal cells during the proliferation period. In human uterine leiomyosarcoma tissue, however, significant cyclin E expression is observed in the nucleus during the mitotic period. This indicates that cyclin E transcription or expression can serve as an indicator of malignancy of tumors observed in uterine smooth muscle cells.

Alternatively, LMP2 and cyclin E may be detected simultaneously. When the level of LMP2 transcription or expression is lowered and the level of cyclin E transcription or expression is elevated, a patient may be determined as being afflicted with uterine leiomyosarcoma. When both LMP-2 and cyclin E are used as indicators, uterine leiomyosarcoma can be detected more accurately than when LMP2 or cyclin E is used alone.

In the present invention, determination of whether or not a patient is afflicted with uterine leiomyosarcoma, differentiation of whether a tumor in uterine smooth muscle is uterine leiomyoma or uterine leiomyosarcoma, and evaluation of malignancy of tumors observed in uterine smooth muscle cells are referred to as detection of uterine leiomyosarcoma.

According to the method of the present invention, uterine leiomyosarcoma can be detected by detecting either or both transcription or expression of LMP2 and/or cyclin E in uterine smooth muscle layer. LMP2 or cyclin E transcription can be detected by measuring mRNA encoding LMP2 or cyclin E. LMP2 or cyclin E expression can be detected by measuring an LMP2 or cyclin E protein.

When LMP2 and/or cyclin E transcription is to be detected, a tissue or cell in uterine smooth muscle layer is collected as a biological sample, and mRNA encoding LMP2 and/or cyclin E contained in such sample may be assayed. In order to assay mRNA, some tissue is obtained from uterine smooth muscle tissue via biopsy or with the use of cotton swabs or the like. The tissue may be obtained, for example, at the time of a usual outpatient visit, by inserting biopsy forceps into the uterine lumen and obtaining an about 1- to 2-mm-square uterine tissue slice. mRNA may be assayed by extracting mRNA from the sampled tissue or cell or by preparing a tissue slice sample. Alternatively, the sampled cells may be immobilized on a glass slide, subjected to in situ hybridization, and then stained. Also, extracted mRNA may be assayed via conventional RNA assay techniques, such as Northern blotting or RT-PCR. mRNA can be extracted by a conventional technique, in accordance with, for example, "Lectures on Biochemical Experiments, 2, Nucleic Acids I, Separation and Purification," Tokyo Kagaku Dojin, Co., Ltd., Jul. 10, 1991 or Molecular Biology Experimental Protocol I, Maruzen Co., Ltd., Jun. 30, 1997. in situ hybridization can be carried out in accordance with, for example, Molecular Biology Experimental Protocol III, Maruzen Co., Ltd., Aug. 30, 1997. In such a case, a probe or primer comprising a partial sequence complementary to a partial sequence of mRNA encoding LMP2 and/or cyclin E is used, in order to specifically assay mRNA encoding LMP2 and/or cyclin E. The nucleotide sequence of LMP2 is known (e.g., GenBank Accession No.: U01025, SEQ ID NO: 1; SEQ ID NO: 2 represents an amino acid sequence of the LMP2 protein), and a probe or primer can be designed in accordance with known nucleotide sequence information. The nucleotide sequence of cyclin E is also known (e.g., GenBank Accession No.: M73812, SEQ ID NO: 8). Such primer or probe is a fragment of the above LMP2 and/or cyclin E gene comprising 5 to 50, preferably 10 to 30, and more preferably 15 to 25 nucleotides.

When LMP2 and/or cyclin E expression is to be detected, a tissue or cell in uterine smooth muscle layer is obtained as a biological sample, and the LMP2 and/or cyclin E protein contained in the sample may be assayed. The tissue or cell in uterine smooth muscle layer may be obtained in the above-described manner. The LMP2 and/or cyclin E protein may be assayed by extracting a protein from the tissue or cell and assaying the LMP2 and/or cyclin E protein in the extract. Protein assay may be conducted via an immunohistochemical or immunocytochemical means. The extracted protein may be assayed via conventional immunoassay techniques, such as ELISA or radioimmunoassay. In such a case, an antibody reacting with LMP2 and/or cyclin E is necessary. An anti-LMP2 antibody and/or an anti-cyclin E antibody may be prepared via a conventional techniques as a monoclonal or polyclonal antibody. Commercially available anti-LMP2 antibody and/or anti-cyclin E antibody can also be used. An antibody may be labeled with an enzyme, fluorescent substance, or radioisotope via a conventional technique, according to need. Immunohistochemical or immunocytochemical assay may be carried out by preparing a sample of the obtained uterine smooth muscle tissue slice or immobilizing the obtained cell on a glass slide. When immunohistochemical assay is performed, for example, the tissue is immobilized with formalin, embedded in paraffin, and sliced to a thickness of about 1 to 5 μm using a slicer, such as a microtome, to prepare a slice sample. At the time of assay, paraffin may be removed via xylene or ethanol treatment, and the sample may be soaked in physiological saline or buffer for hydrophilization. Staining may be carried out with the use of an anti-LMP2 antibody and/or anti-cyclin E antibody labeled with an enzyme, fluorescent substance, radioisotope, or the like. Alternatively, an anti-LMP2 antibody may be conjugated to LMP2 and/or cyclin E in the slice sample, and a secondary antibody that is conjugated to the anti-LMP2 antibody and/or anti-cyclin E antibody, which is labeled with an enzyme, fluorescent substance, or the like, may be used. Examples of enzymes used for labeling include horseradish peroxidase and alkaline phosphatase. Examples of fluorescent substances include fluorescein and rhodamine. Staining may also be carried out using a known biotin-avidin complex. Immunocytochemical assay may be carried out by immobilizing the obtained cell on a glass slide with the aid of formalin and visualizing LMP2 and/or cyclin E in the cell in the same manner as in the case of immunohistochemical assay. In immunohistochemical or immunocytochemical assay, the results of staining may be evaluated microscopically or visually. An adequate optical apparatus may also be used. Immunohistochemical staining may be carried out in accordance with, for example, Molecular Biology Experimental Protocol III, Maruzen Co., Ltd., Aug. 30, 1997.

When the LMP2 transcription or expression level is found to be lost or lowered upon detection of LMP2 transcription or expression in uterine smooth muscle tissue or cell as described above, a patient can be determined as being afflicted with uterine leiomyosarcoma. When the cyclin E transcription or expression level is found to be elevated upon detection of cyclin E transcription or expression in uterine smooth muscle tissue or cell, a patient can be determined as being afflicted with uterine leiomyosarcoma. Also, transcription or expression levels of both LMP2 and cyclin E may be detected simultaneously. When the LMP2 transcription or expression level is lost or lowered and the cyclin E transcription or expression level is elevated, a patient can be determined as being afflicted with uterine leiomyosarcoma. When assay of LMP2 mRNA, the LMP2 protein, cyclin E mRNA, or the cyclin E protein in the tissue or cell extract is intended, for example, LMP2 mRNA, the LMP2 protein, cyclin E mRNA, or the cyclin E protein per tissue unit weight or per unit cell count of a healthy individual who is not afflicted with uterine leiomyosarcoma is assayed in advance. When the LMP2 mRNA or LMP2 protein level is significantly lower than the level of a healthy individual, a patient can be determined as being afflicted with uterine leiomyosarcoma. When the cyclin E mRNA or cyclin E protein level is significantly higher than the level of a healthy individual, a patient can be determined as being afflicted with uterine leiomyosarcoma.

When the tissue or cell is subjected to LMP2 transcription or expression assay via in situ hybridization, immunohistochemical assay, or immunocytochemical assay, the tissue or cell is not stained, and no LMP2 transcription or expression is observed, the tissue or cell at such region is a uterine leiomyosarcoma tissue or cell, and a patient whose tissue or cell was sampled can be determined as being afflicted with uterine leiomyosarcoma. When the tissue or cell is subjected to cyclin E transcription or expression assay via in situ hybridization, immunohistochemical assay, or immunocytochemical assay, the tissue or cell is strongly stained, and strong cyclin E transcription or expression is observed, the tissue or cell at such region is a uterine leiomyosarcoma tissue or cell, and a patient whose tissue or cell was sampled can be determined as being afflicted with uterine leiomyosarcoma. In such a case, normal tissue, which is not uterine leiomyosarcoma tissue, and a stained tissue slice or cell sample of uterine leiomyosarcoma may be prepared in advance, and the tissue or cell obtained from the patient may be compared with such sample.

Detection of LMP2 transcription or expression can be employed to differentiate whether a tumor of a patient afflicted with a uterine smooth muscle tumor is malignant or benign, i.e., whether a patient is afflicted with uterine leiomyosarcoma or uterine leiomyoma. In such a case, tissue in which the LMP2 transcription or expression level is lost or significantly lowered compared with normal tissue can be determined as corresponding to malignant uterine leiomyosarcoma. Also, detection of cyclin E transcription or expression can be employed to differentiate whether a tumor of a patient afflicted with a uterine smooth muscle tumor is malignant or benign, i.e., whether a patient is afflicted with uterine leiomyosarcoma or uterine leiomyoma. In such a case, tissue in which the cyclin E transcription or expression level is significantly elevated compared with normal tissue can be determined as corresponding to malignant uterine leiomyosarcoma. Detection of both LMP2 and cyclin E enables more accurate determinement of malignancy and more accurate differentiation. If tissue-based in situ hybridization or immunohistochemical assay is performed, a normal region of the tissue can be distinguished from a region afflicted with uterine leiomyosarcoma. For example, the number of cells in which the LMP2 and/or cyclin E transcription or expression level is lost or lowered per tissue unit volume or unit cell count may be determined to determine malignancy of the uterine smooth muscle tumor.

Further, a conventional method for diagnosing uterine leiomyosarcoma may be carried out in combination with the method for diagnosing uterine leiomyosarcoma using LMP2 and/or cyclin E transcription or expression as an indicator of the present invention to perform more accurate detection. Examples of conventional methods include a method involving observation of cellular morphology, density, and other conditions and a method for diagnosing uterine leiomyosarcoma using myosin transcription or expression as an indicator. Such methods have been primarily carried out by immobilizing tissues or cells. That is, a tissue slice sample or a cell sample on a glass slide may be prepared, the cellular morphology or density of the sample may be assayed, myosin transcription or expression may be assayed, and LMP2 and/or cyclin E transcription or expression may further be assayed.

The present invention includes a method for treating uterine leiomyosarcoma by administering the LMP2 gene to a patient afflicted with uterine leiomyosarcoma and an agent used for gene therapy comprising the LMP2 gene. At the time of gene therapy, a target gene can be introduced into a patient afflicted with uterine leiomyosarcoma in accordance with a known method. A gene can be introduced into a patient by a method involving the use of a virus vector and a method involving the use of a nonvirus vector, and a variety of such methods are known (Basic Technology of Gene Therapy, Separate Volume of Experimental Medicine published by Yodosha, Japan, 1996; Gene Introduction and Expression Analysis Method, Separate Volume of Experimental Medicine, published by Yodosha, Japan, 1997; Gene Therapy Development Research Handbook, edited by The Japan Society of Gene Therapy, published by NTS, Japan, 1999). An example of a representative method is a method involving the use of a virus vector, such as an adenovirus, adeno-associated virus, or retrovirus vector, for gene introduction.

A target gene is introduced into a DNA virus or RNA virus such as a neutralized retrovirus (i.e., a virus that cannot replicate), herpes virus, vaccinia virus, pox virus, polio virus, sindbis virus, sendai virus, SV40, immune deficiency disease virus (HIV) and so forth, in order to infect the cell with a recombinant virus to thereby introduce the gene into the cell. This enables introduction of the gene into the cell. Also, a gene expression vector such as a plasmid vector can be used to introduce the LMP2 gene into the cell or tissue. For example, the LMP2 gene can be introduced into the cell by lipofection, the phosphate-calcium coprecipitation method, the DEAE-dextran method, or direct injection of DNA using a micro-glass tube. Also, a recombinant expression vector can be incorporated into the cell via, for example, a method of gene introduction with internal type liposome, a method of gene introduction with electrostatic type liposome, the HVJ-liposome method, the improved HVJ-liposome method (HVJ-AVE liposome method), a method involving the use of an envelop vector (HVJ-E), the receptor-mediated gene introduction method, a method of introducing DNA molecules together with carriers (metal particles) by a particle gun, a method of directly introducing naked-DNA, or a method of introduction with a variety of polymers. Expression vectors as used herein may be any expression vectors as long as they permit the expression in vivo of the gene of interest. Examples include expression vectors such as pCAGGS (Gene 108: 193-200, 1991), pBK-CMV, pcDNA3, pZeoSV (Invitrogen, Stratagene), and pVAX1.

A vector comprising the LMP2 gene may comprise a marker gene or the like for labeling and/or select a cell into which a promoter or enhancer, poly-A-signal, or gene for transcribing a gene has been introduced. A known promoter can be used.

A gene therapy agent comprising the LMP2 gene comprises a vector comprising the LMP2 gene and pharmacologically acceptable carriers, a diluent, or an excipient. A carrier, a diluent, and an excipient that are generally used in the field of drug preparation can be used. For example, lactate or magnesium stearate is used as a carrier or excipient for a tablet. An isotonic solution comprising physiological saline, glucose, other adjuvant compositions, or the like is used as an aqueous injection solution, and it may be used in combination with an adequate solubilizer, such as an alcohol, a polyalcohol such as propylene glycol, or a nonionic surfactant. As an oily liquid, sesame oil, soybean oil, or the like may be used, and benzyl benzoate or benzyl alcohol may be used in combination as a solubilizer. The gene therapy agent of the present invention is preferably administered topically to the uterine leiomyosarcoma region. For example, such agent may be injected into the uterine leiomyosarcoma region.

The dose varies depending on symptoms, age, body weight, and other conditions. For example, the LMP2 gene that may be inserted into an expression vector or the like that expresses LMP2 in the body of a patient afflicted with uterine leiomyosarcoma, and this may be directly injected into the uterine leiomyosarcoma region in amounts of 0.001 mg to 100 mg per dose at intervals of several days, several weeks, or several months.

The present invention further includes a method for determining whether or not a patient is afflicted with uterine leiomyosarcoma based on mutations of a given factor associated with the interferon γ (IFN-γ) signal transduction cascade or whether or not a patient is at risk of being afflicted with uterine leiomyosarcoma.

Figure 15:
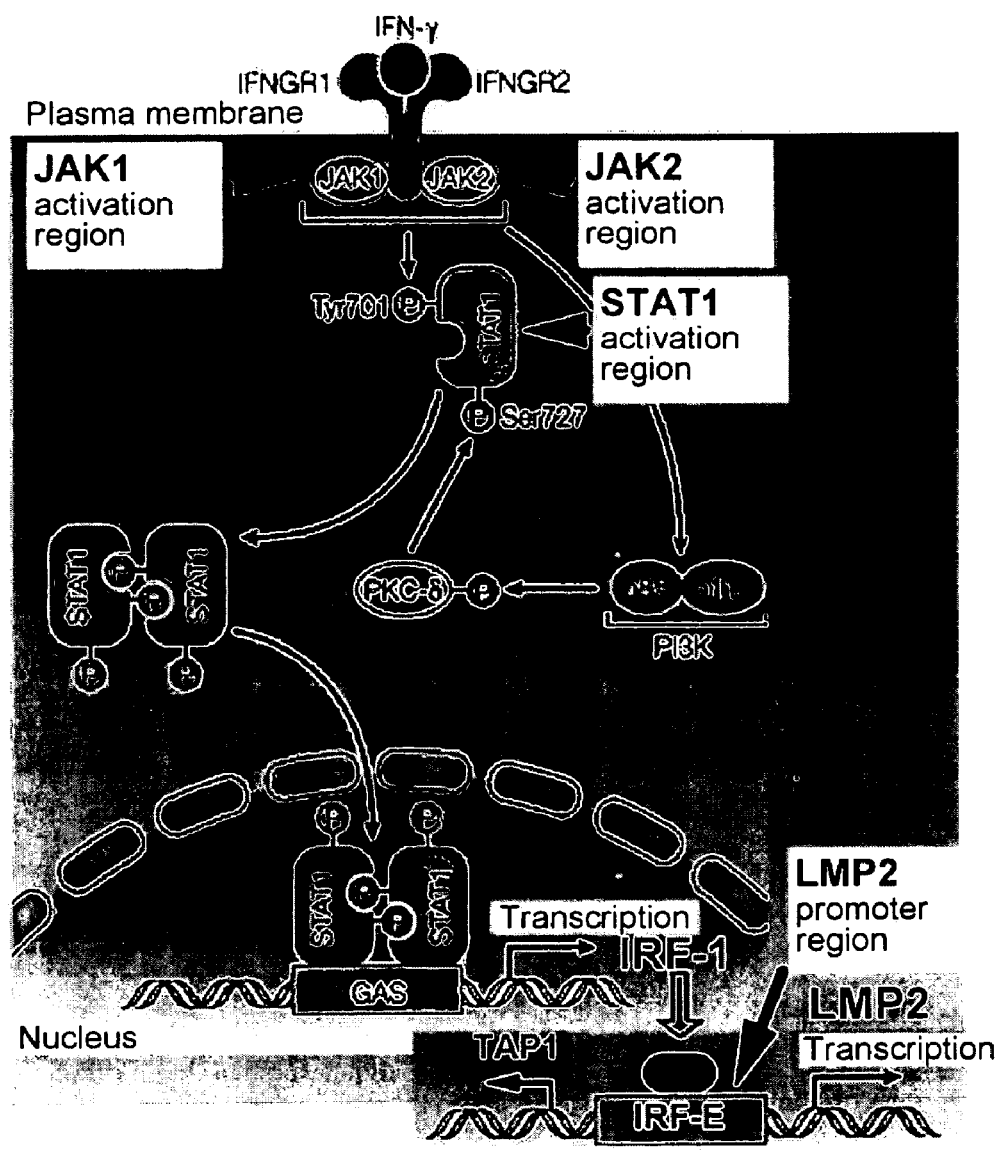
FIG. 15 shows the correlation between the INF-γ signal transmission pathway and LMP2 expression.

While the LMP2 gene is activated by IFN-γ in a normal cell, IFN-γ-induced LMP2 activation is not substantially observed in a uterine leiomyosarcoma cell. IFN-γ-induced LMP2 activation occurs in the following manner. That is, IRF-1 is induced by JAK1 kinase, JAK2 kinase, or STAT1 to express and bind to the promoter of the LMP2 gene. Such mechanism is shown in FIG. 15. Among the factors that are associated with IFN-γ signal transduction, mutation of the JAK1 kinase and the STAT1 gene and mutation of the promoter region of LMP2 would block signal transduction, and LMP2 expression would be inhibited.

Mutation is as described below. In the following description, the gene mutation represented by "A210G," for example, indicates substitution of A as residue 21 of the gene nucleotide sequence with G. Mutation in the amino acid sequence of a protein encoded by the gene represented by "G871E" indicates substitution of glycine 871 (G) with glutamic acid (E) in the amino acid sequence.

| Mutation in JAK1 kinase | | |
|---|---|---|
| Gene mutation | Corresponding amino acid mutation | Domain comprising mutation |
| A2612A | G781E | ATP binding |
| G2626A | G876R | ATP binding |
| G2642T | C881F | ATP binding |
| A2967C | G986P | Active site |
| A2960C | Y987S | Active site |
| A2985T | R995S | Active site |

The nucleotide sequence of the JAK1 kinase gene is shown in SEQ ID NO: 3, and the amino acid sequence of the JAK1 kinase is shown in SEQ ID NO: 4.

| Mutation in STAT1 | | |
|---|---|---|
| Gene mutation | Corresponding amino acid mutation | Domain comprising mutation |
| A2104C | I702L | Non-kinase-active region |
| T2128G | S710A | Non-kinase-active region |
| T2078G | L693R | Non-kinase-active region |
| A2148C | R716S | Non-kinase-active region |

The nucleotide sequence of the STAT1 gene is shown in SEQ ID NO: 5, and the amino acid sequence of the STAT1 is shown in SEQ ID NO: 6.

| LMP2 promoter | | |
|---|---|---|
| Gene mutation | Corresponding amino acid mutation | Domain comprising mutation |
| A210G | | IRF-E site |
| C214T | | IRF-E site |
| A216G | | IRF-E site |
| A217G | | IRF-E site |
| G219A | | IRF-E site |

The gene sequence of the LMP2 promoter is shown in SEQ ID NO: 7.

Full-length DNA of the JAK1 kinase gene, the STAT1 gene, or the LMP2 promoter or a fragment thereof can be easily obtained based on the nucleotide sequence information.

The present invention includes: a method for detecting whether or not a patient is afflicted with uterine leiomyosarcoma by detecting a nucleotide mutation of the JAK1 kinase gene, the STAT1 gene, or the LMP2 promoter or a method for determining whether or not a patient is at high risk of being afflicted with uterine leiomyosarcoma; and a method for detecting whether or not a patient is afflicted with uterine leiomyosarcoma by detecting an amino acid mutation of the JAK1 kinase or STAT1 gene or a method for determining whether or not a patient is at high risk of being afflicted with uterine myosarcoma.

A nucleotide mutation in the gene may be detected using a gene fragment containing the above mutation site as a probe or DNA that is immobilized on a DNA chip or DNA microarrays. In such a case, the sequence of the fragment may be a full-length nucleotide. In general, such fragment preferably comprises 15 bp to 100 bp, more preferably 15 bp to 50 bp, and particularly preferably 18 bp to 30 bp. The number of mutation sites to be contained in the fragment may be one or sevaral; i.e., two, three, four, five, or six.

DNA comprising a sequence complementary to such fragment is within the scope of the present invention. DNA comprising a complementary sequence can be obtained in accordance with the disclosure of the present description.

The probe of the present invention may be labeled with a fluorescent substance, enzyme, radioisotope, chemiluminescent substance, or the like, to facilitate detection. A known labeling substance may be used, and labeling may be carried out by a known technique. Examples of fluorescent substance include Cy3, Cy5, rhodamine, and fluorescein.

Further, a primer used for PCR, such as PCR-RFLP, for detecting the above gene mutation is also within the scope of the present invention. Specifically, the present invention includes a pair of primer sets that can be used for amplification of a DNA fragment comprising partial sequences each consisting of 10 to 30 nucleotides and being located at sites that are each closer to the 3' end and the 5' end from the mutation site of the above JAK1 kinase gene, the STAT1 gene, and the LMP2 promoter.

Mutation can be detected using DNA of the present invention via, for example, PCR, Southern hybridization, Northern hybridization, quantitative PCR, in situ hybridization, fluorescence in situ hybridization (FISH), PCR-RFLP, or PCR-SSCP.

For example, a probe complementary to a nucleotide sequence comprising a nucleotide mutation site of the JAK1 kinase gene, STAT1 gene, or LMP2 promoter and a probe complementary to a nucleotide sequence comprising a region corresponding to the nucleotide mutation site of a wild-type gene are first prepared. The length of a probe to be used is not limited. It may comprise the full length of a nucleic acid fragment to be amplified via the nucleic acid amplification method described below. In general, such length is preferably 15 bp to 100 bp, more preferably 15 bp to 50 bp, and particularly preferably 18 bp to 30 bp. A probe that is labeled with a radioisotope, fluorescent substance, enzyme, or the like may be used. Subsequently, tissue sampled from uterine smooth muscle tissue or a gene fragment comprising a nucleotide mutation site of the cell specimen sample is amplified via nucleic acid amplification, and the resulting amplified fragment is allowed to react with a probe. By inspecting whether or not DNA in the specimen sample hybridizes to a wild-type or mutant probe, whether or not mutation has occurred in the DNA of the gene can be detected. The probe of the present invention detects a single nucleotide mismatch. Thus, hybridization needs to be carried out under stringent conditions. At the time of hybridization, temperature and salt concentration may be regulated, so that hybridization conditions under which a single nucleotide mismatch can be selectively detected can be selected. Specifically, hybridization can be carried out, for example, at a sodium concentration of 150 mM to 900 mM, and preferably 600 to 900 mM, and at 60° C. to 68° C., and preferably 65° C., although such conditions depend on the length of probe DNA to be used.

As primers used for nucleic acid amplification, sequences that sandwich the above gene mutation region and that are complementary to the ends of the region to be amplified can be used. The length of the region to be amplified is not limited, and it can be several tens to several hundreds nucleotides. The length of an amplified nucleotide sequence may be determined so as to comprise only one DNA mutation of the JAK1 kinase gene, STAT1 gene, and LMP2 promoter in the region to be amplified. Alternatively, such length may be determined so as to comprise a plurality of mutations; i.e., two, three, four, five, or six mutations. A region comprising a mutation site can be designated as a primer. The primer length is not limited, and it is preferably 15 bp to 50 bp, and more preferably 20 bp to 30 bp.

Further, DNA complementary to the DNA sequence comprising mutation of the JAK1 kinase gene, STAT1 gene, or LMP2 promoter site of the present invention or a fragment thereof may be used to prepare a DNA that is used for determining whether or not a patient is afflicted with uterine leiomyosarcoma or whether or not a patient is at risk of being afflicted with uterine leiomyosarcoma. In such a case, a DNA fragment complementary to a region comprising mutation of the JAK1 kinase gene, STAT1 gene, or LMP2 promoter site of the present invention may be immobilized on a nitrocellulose or nylon membrane or a glass slide. The nucleotide length of the DNA fragment to be immobilized is preferably 15 bp to 100 bp, more preferably 15 bp to 50 bp, and particularly preferably 15 bp to 25 bp, in general. Subsequently, the DNA chip is brought into contact with DNA or RNA derived from a subject, which is labeled with a radioisotope, enzyme, fluorescent dye, or the like. Whether or not the DNA chip undergoes hybridization may be inspected to determine whether or not the specimen contains a nucleic acid having mutation.

Mutation may be detected by extracting a nucleic acid from the tissue slice or cell sampled from uterine smooth muscle tissue.

The present invention is hereafter described in greater detail with reference to the following examples, although the technical scope of the present invention is not limited thereto.

EXAMPLE 1

LMP2 Transcription and Expression in Human Uterine Leiomyosarcoma

In this example, the materials and methods described below were used.

Cell Strain and Medium

Human uterine leiomyosarcoma cell lines, i.e., SKN cells (RCB0513), were purchased from Cell Bank, RIKEN Bio Resource Center, and the cells were retained in F-12 Nutrient Mixture (Ham) medium (Invitrogen) supplemented with 0.6% L-glutamine (Invitrogen) and 15% fetal bovine serum (Sigma-Aldrich, Inc.). HeLa cells and HeLa.S3 cells were retained in Dulbecco's MEM supplemented with 0.6% L-glutamine and 10% fetal bovine serum. Human uterine smooth muscle cells were purchased from Cambrex Bio-Science Wailersville and retained in accordance with the manufacturer's protocol.

Reverse Transcription Polymerase Chain Reaction (RT-PCR) Analysis

TAP1, LMP2, β2-m, and β-actin transcripts were inspected via RT-PCR. The cells were either treated or not treated with 250 unit/ml of human IFN-γ (Pepro Tech) for 48 hours, and RNA was recovered. Total RNA was prepared from $5 \times 10^6$ cells using the TRIzol reagent (Invitrogen) in accordance with the manufacturer's protocol. RNA was reverse-transcribed using the Superscript II enzyme (Invitrogen), and single-stranded cDNA was used to amplify the TAP1, LMP2, β2 m, and β-actin transcripts. PCR was carried out using an adequate primer with 35 cycles of 30 seconds at 94° C., 30 seconds at 60° C., 1.5 minutes at 72° C., and an additional 5 minutes to extend the transcripts (Cabrera CM. et al., 2003, Tissue Antigens, 61,211-219; Miyagi T. et al., 2003, J. Gastroenterol. Hepatol., 18, 32-40).

Immunohistochemical Assay (Immunohistochemistry=IHC)

IHC was carried out using an avidin-biotin complex in accordance with the method described in Hsu S M. et al., 1981, J. Histochem. Cytochem. 29, 577-580. More specifically, 6 representative 5-μm tissue slices were prepared from paraffin-embedded sample of uterine tissue excised from patients afflicted with uterine leiomyosarcoma. Paraffin was removed from the tissue slices, the tissue slices were rehydrated in alcohol, and the tissue slices were then incubated for 20 minutes using normal murine serum. Subsequently, the tissue slices were incubated using the anti-LMP2 antibody (Affinity Res. Products, 100-fold diluted) for 1 hour at room temperature. Thereafter, the slices were incubated with the biotinylated secondary antibody (Dako). The reaction was completed using 3,3'-diaminobenzidine, and the slide was counterstained with hematoxylin. The normal uterine smooth muscle tissue in the sample was used as a positive control. A negative control sample consisting of the tissue slices was incubated with normal rabbit IgG instead of the primary antibody.

Immunoprecipitation and Immunoblotting

The cytoplasm extract and the nuclear extract were prepared from $5 \times 10^6$ cells that had been treated or had not been treated with 250 units/ml of human IFN-γ (Brucet M. et al., 2004, Genes Immun., 5, 26-35). The cells were recovered by centrifugation at 1,200 rpm for 10 minutes, washed with 5 ml of ice-cooled PBS, and centrifuged at 12,000 rpm and 4° C. for 5 minutes. The cells were pelletized, washed once in 0.4 ml of buffer A (10 mM Hepes, pH 7.8; 10 mM KCl; 2 mM $MgCl_2$; 1 mM DTT; 0.1 mM EDTA; and the Complete Protease Inhibitor Cocktail (Kirkegaard & Perr Lab)), and incubated at 4° C. for 2 hours. Subsequently, 25 μl of 10% Nonidet P-40 solution was added, the cells were vigorously mixed at 4° C. for 1 hour, and centrifugation was then carried out at 12,000 rpm for 5 minutes. Thereafter, the supernatant was recovered as a cytoplasm extract and stored at −80° C. The pelletized nucleus was resuspended in 40 μl of buffer C (50 mM Hepes, pH 7.8; 50 mM KCl; 300 mM NaCl; 0.1 mM EDTA; 1 mM DTT; and 10% (v/v) glycerol), mixed at 4° C. for 2 hours, and centrifuged at 4° C. and 12,000 rpm for 5 minutes. The supernatant containing a nuclear protein was recovered and stored at −80° C.

In order to detect STAT1, phosphorylated STAT1, JAK1, JAK2, TAP1, and LMP2 expression, a lytic solution or cytoplasm extract was separated on 10% SDS-polyacrylamide gel (SDS-PAGE), and immunoblotting was carried out in accordance with a conventional technique with the use of anti-STAT1 antibody, anti-phosphorylated STAT1 antibody (Santa-Cruz Biotechnol.), anti-JAK1, anti-JAK2 antibody (Chemicon Int'l), antibody TAP1 antibody (Stressgen), or anti-LMP2 antibody (Affiniti Res. Products). In order to detect IRF1 or IRF2 expression, a nuclear extract was separated on 10% SDS-PAGE, and immunoblotting was carried out in accordance with a conventional technique using the anti-IRF1 antibody (Transduction Lab.) and the anti-IRF2 antibody (Santa-Cruz Biotechnol.). Expression of the target protein was visualized and tested by performing alkaline phosphatase color development in accordance with the manufacturer's protocol using a secondary antibody conjugated to alkaline phosphatase.

The whole-cell extract obtained from $5 \times 10^6$ cells that had been treated or not treated with 250 units/ml of IFN-γ for the period of time as shown in the figure was lysed in a buffer containing 50 mM Tris-HCl, 0.1 mM EDTA, 200 mM NaCl, 10% glycerol, 0.5% NP-40, 1 mM DTT, and the Complete Protease Inhibitor Cocktail (Kirkegaard & Perr Lab.). The lytic solution was clarified in advance with normal rabbit blood serum (Santa-Cruz Biotechnol.) and 20 ml of protein G sepharose (Amersham Biosciences) and then subjected to immunoprecipitation using 2 μg of anti-JAK1 or anti-JAK2 antibody. The sample was separated on 10% SDS-PAGE and transferred onto the Immobilon-P membrane. The phosphorylated protein was first allowed to react with the anti-tyrosine phosphorylated antibody as a primary antibody and then subjected to alkaline phosphatase color development using a secondary antibody conjugated to alkaline phosphatase in accordance with the manufacturer's protocol to visualize and test the protein. In order to detect expression of the IFN-γ R1 strand, the whole-cell lysate was separated in the manner described above. Blotting was performed using the anti-IFN-γR1 strand antibody (PBL Biomedical Laboratories). SKN cells were transfected with the use of 2 μg of pRK5 control or 2 μg of JAK1 expression vector (provided by Dr. J. Ihle of St. Jude Children Research Hospital, Memphis, Tenn.). IFN-γ was added 24 hours after transfection, and the cells were incubated for an additional 24 hours prior to recovery thereof. Such transfection was carried out simultaneously with pCMVβ-Gal transfection, in order to standardize the transfection efficiency.

Transfection and Reporter Assay

Figure 2:
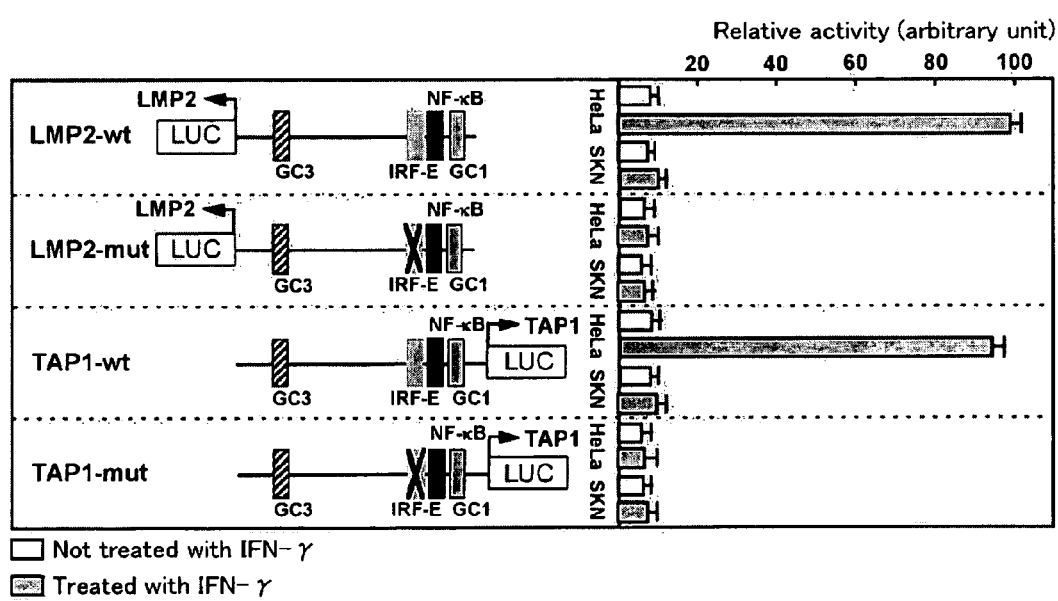
FIG. 2 shows differential activity of wt and IRF-E mt promoters shared by IFN-γ-induced TAP1 and LMP2 in the HeLa and SKN cells. This figure shows wt promoters shared by TAP1 and LMP2 (TAP1 593-1/pGL3 and LMP2 1-593/pLG3) and luciferase reporter gene constructs each comprising IRF-E mutant promoters. The reporter genes were introduced into the HeLa and SKN cells, IFN-γ was added 24 hours later, and the cells were incubated for 24 hours prior to recovery thereof. For the purpose of standardization of efficiency of reporter gene introduction, the reporter genes were introduced simultaneously with pSMV-βGAL. The results were standardized with the expression of the luciferase gene assayed separately for the HeLa cells and the SKN cells, and the results are shown as relative TAP1 and LMP2 activities. The average of the results attained from the three independent experiments is shown, and the error bar indicates SE.

FIG. 2 shows the structures of TAP1 and LMP2wt (TAP1 593-1/pGL3 and LMP2 1-593/pLG3) and the structure of the IRF-E mutant promoter construct thereof. These plasmid DNAs (2 μg in total, provided by Dr. K. L. Wright of University of South Florida) were transferred into the HeLa or SKN cells using the FuGENE 6 Transfection Reagent (Roche) in accordance with the manufacturer's recommendation. All the transferred DNAs contained 200 ng of pCMVβ-Gal (Tropix) as an internal transfection efficiency control. IFN-γ (final concentration: 250 units/ml) was added 24 hours after transfection, and the cells were incubated for an additional 24 hours. At the last stage, the cells were washed, lysed in 500 μl of lytic buffer, and analyzed using the Dual-Luciferase Reporter Assay System (Promega) in accordance with the manufacturer's instructions. The luciferase activity of cells into which pGL3 had been transfected instead of LMP2 or TAP 1/pGL3 was subtracted as a background.

The following results were obtained using the above materials and the above method.

Noninduction of INF-γ-Induced TAP1 and LMP2 Expression in Human Uterine Leiomyosarcoma Cells LMP2-lacking mice developed uterine leiomyosarcoma (Hayashi T. et al., 2002, Cancer Res., 62, 24-27). Subsequently, demonstration as to whether or not human uterine leiomyosarcoma shows weak expression of TAP1 and LMP2 would be required. The effects of IFN-γ on TAP1 and LMP2 expression were inspected by immunoblotting using 4 types of cell lines. Treatment with HeLa, HeLa.S3, and Hu.USMC (the control) subsequent to treatment with IFN-γ strongly induced TAP1 and LMP2 expression; however, the level of TAP1 and LMP2 expression induced by treatment with IFN-γ was insignificant in SKN cells, i.e., the human leiomyosarcoma cell lines (FIG. 1a). β-actin expression in SKN cells was similar to that in both HeLa and HeLa.S3 cells and in Hu.USMC (i.e., the control). Thus, the process of preparing an extract did not affect the noninduction of TAP1 and LMP2 expression, following the treatment with IFN-γ. The amount of IFN-γ was sufficient to maximally induce the shared bidirectional promoter for both HeLa and HeLa.S3 cells and for both TAP1 and LMP2 genes in Hu.USMC (FIG. 1a). Even if the amount of INF-γ was increased to 500 units/ml, TAP1 and LMP2 expression was not significantly induced in SKN cells. Accordingly, SKN cells were found to have lost the capacity for increasing TAP1 and LMP2 expression via treatment with IFN-γ.

Figure 1B:
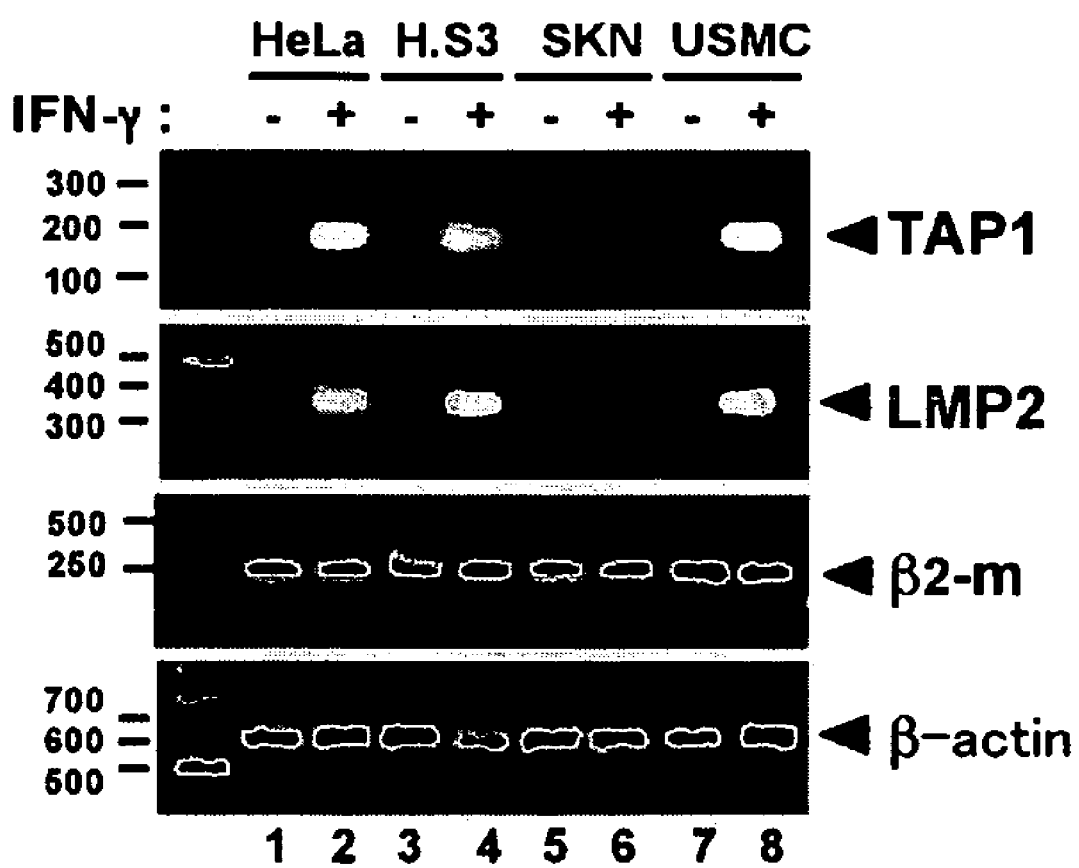
FIG. 1b is a photograph showing a lack of IFN-γ-induced TAP1 and LMP2 expression in SKN cells and showing the results of mRNA expression assay of TAP1, LMP2, and β-actin in HeLa, HeLa.S3, SKN, and Hu.USMC cells via RT-PCR. After the cells were cultured in the presence or absence of IFN-γ (250 units/ml) for 48 hours, RT-PCR was carried out using primers. The DNA product amplified via RT-PCR was separated on agarose gel. A DNA size marker is shown on the left side of the photograph.
Figure 1C:
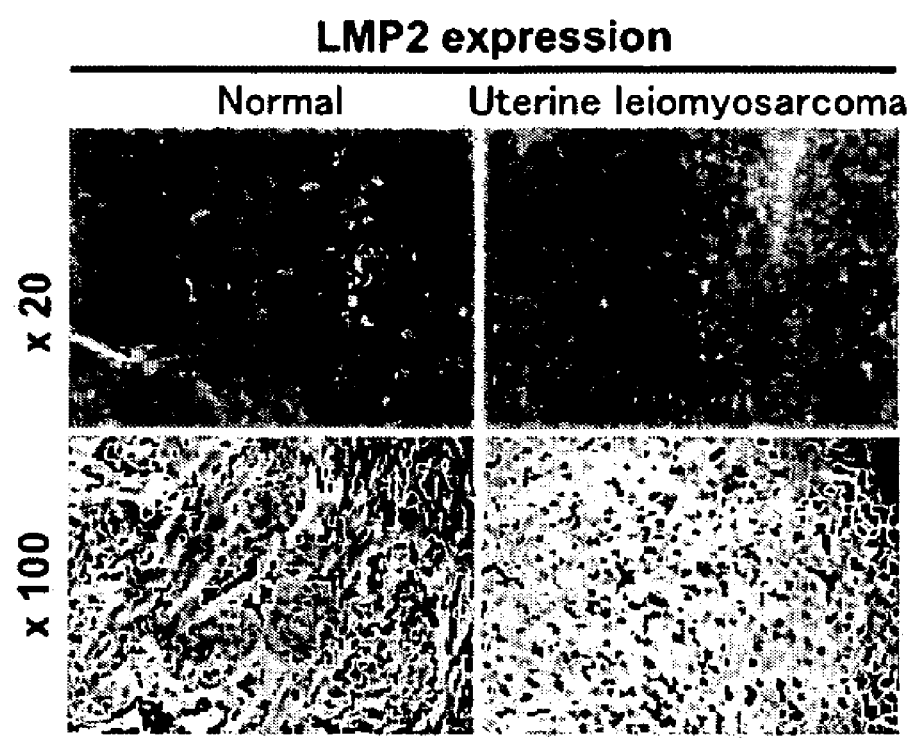
FIG. 1c is a photograph showing a lack of LMP2 expression in uterine leiomyosarcoma, and showing the results of immunohistochemical assay of LMP2 in normal uterine smooth muscle and uterine leiomyoma. A 5-μm slice of the tissue sample was stained with the anti-LMP2 antibody and the peroxidase-conjugated anti-rabbit IgG antibody.

In order to demonstrate noninduction of TAP1 and LMP2 expression following treatment with IFN-γ, RT-PCR analysis was carried out using 4 types of cell lines. mRNA expression of TAP1 or LMP2 induced by treatment with IFN-γ was clearly detected in HeLa and HeLa.S3 cells and in Hu.USMC; however, mRNA expression of TAP1 and LMP2 induced by treatment with IFN-γ was insignificant in SKN cells (FIG. 1b). The mRNA expression levels of the control β-actin were similarly high in all the tested cells. This indicates that a step of RNA preparation did not affect noninduction of TAP1 and LMP2 expression, following treatment with IFN-γ (FIG. 1b). The IHC experiment demonstrated that LMP2 expression levels were significant in 6 cases of normal uterine smooth muscle cells but LMP2 was not expressed in a uterine leiomyosarcoma cell (FIG. 1c). The results of IHC demonstrate noninduction of TAP1 and LMP2 in SKN cells.

Loss of Shared Bidirectional Promoter Activity for TAP1 and LMP2 Genes Induced by IFN-γ

IRF-1 directly binds to a cis-element that is referred to as "IRF-E" in the shared bidirectional promoter for the TAP1 and LMP2 genes (Wright K. L. et al., 1995, J. Exp. Med., 181, 1459-1471; White L. C. et al., 1996, Immunity, 5, 365-376; Dovhey S. E. et al., 2000, Cancer Res., 60, 5789-5796; Brucet M. et al., 2004, Genes Immun., 5, 26-35). As shown in FIG. 2, IRF-E is located upstream of the NFκB-like binding site and the GC1 box. The necessity of IRF-E for enhancing TAP1 and LMP2 expression induced by treatment with IFN-γ was demonstrated (Wright K. L. et al., 1995, J. Exp. Med., 181, 1459-1471; White L. C. et al., 1996, Immunity, 5, 365-376; Dovhey SE. et al., 2000, Cancer Res., 60, 5789-5796; Brucet M. et al., 2004, Genes Immun., 5, 26-35). In order to inspect whether or not IFN-γ would assuredly activate the bidirectional promoter shared by TAP1 and LMP2 in SKN cells, DNA of the promoter-luciferase construct comprising wt or mut as IRF-E was transfected in order to induce TAP1 or LMP2 expression in SKN cells and HeLa cells. In HeLa cells, the level of LMP2 promoter activity induced by IFN-γ treatment was 11 times higher than that before transfection, and the level of TAP1 promoter activity induced thereby was 10 times higher than that before transfection (FIG. 2). As a result of treatment with IFN-γ, however, activation of the bidirectional promoter shared by TAP1 and LMP2 was not observed in SKN cells. IRF-E mutation resulted in a loss of capacity of IFN-γ for inducing expression of the TAP1/LMP2 gene that was observed in the HeLa cells (FIG. 2). These results are consistent with the endogenous mRNA level, which demonstrate that activity of the TAP1 and LMP2 genes is elevated in the HeLa cells but is not elevated in SKN cells. Mutation at the IRF-E site somewhat reduced the expression level that serves as a standard expression level in the HeLa cells and SKN cells. This indicates that such site plays a certain role in LMP-2 expression. These results demonstrate that treatment with IFN-γ can strongly induce the promoter activity shared by TAP1 and LMP2 in HeLa cells but does not induce it in SKN cells (FIG. 2).

EXAMPLE 2

Conditions of LMP2 Expression in the Biopsy Tissue or Surgically-Removed Tissue of the Normal Human Uterine Smooth Muscle Layer, Human Uterine Leiomyoma, and Human Uterine Leiomyosarcoma via Immunohistochemical Assay Microscopic Observation of the Human Normal Uterine Smooth Muscle Layer, Human Uterine Leiomyoma, and Human Uterine Leiomyosarcoma Human uterine smooth muscle tissue was collected by biopsy or surgery to subject the tissue to microscopic observation.

Figure 3:
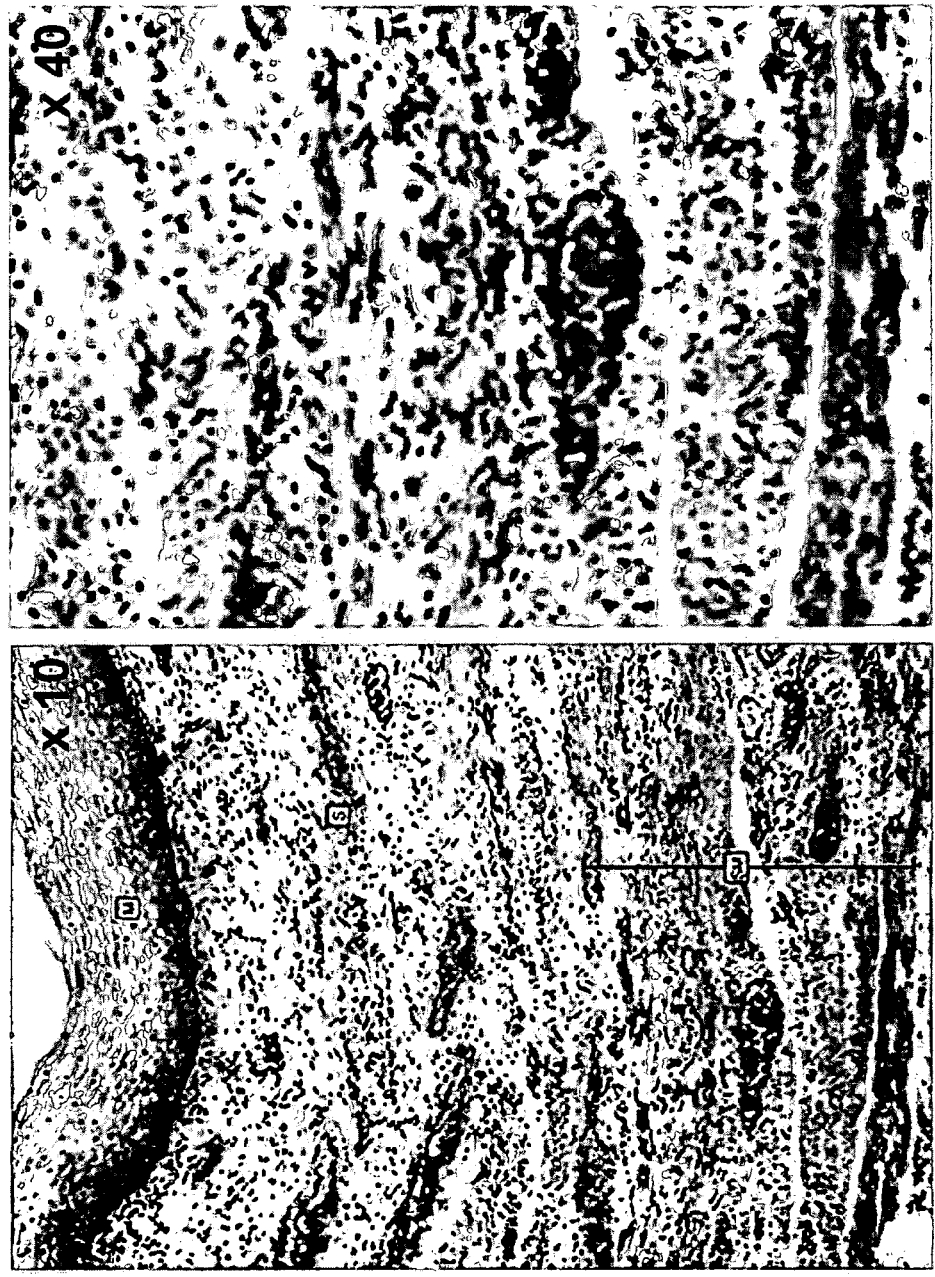
FIG. 3 is a microscopic photograph of normal human uterine smooth muscle tissue.
Figure 4:
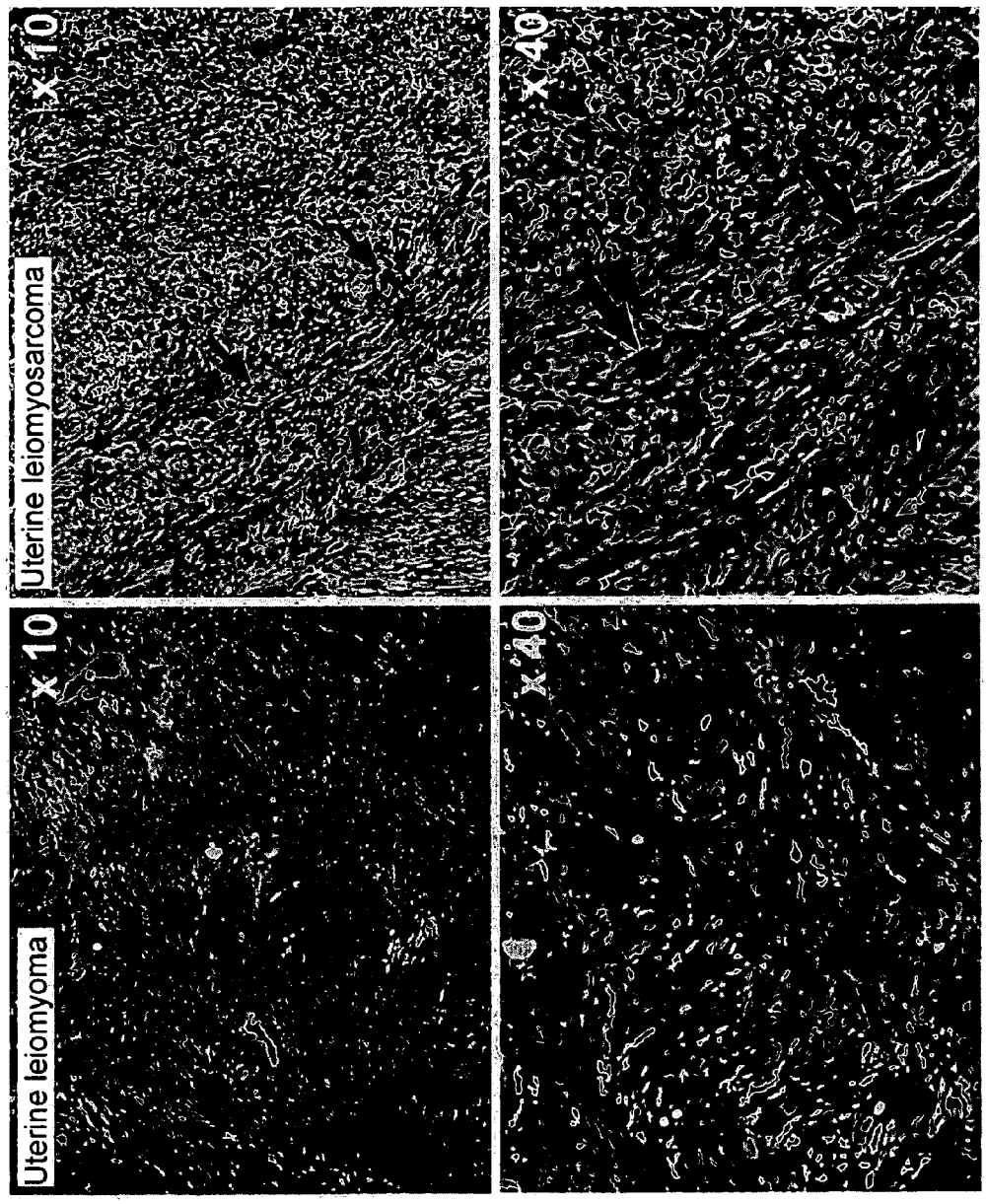
FIG. 4 is a microscopic photograph of human uterine leiomyoma and human uterine leiomyosarcoma.
Figure 5:
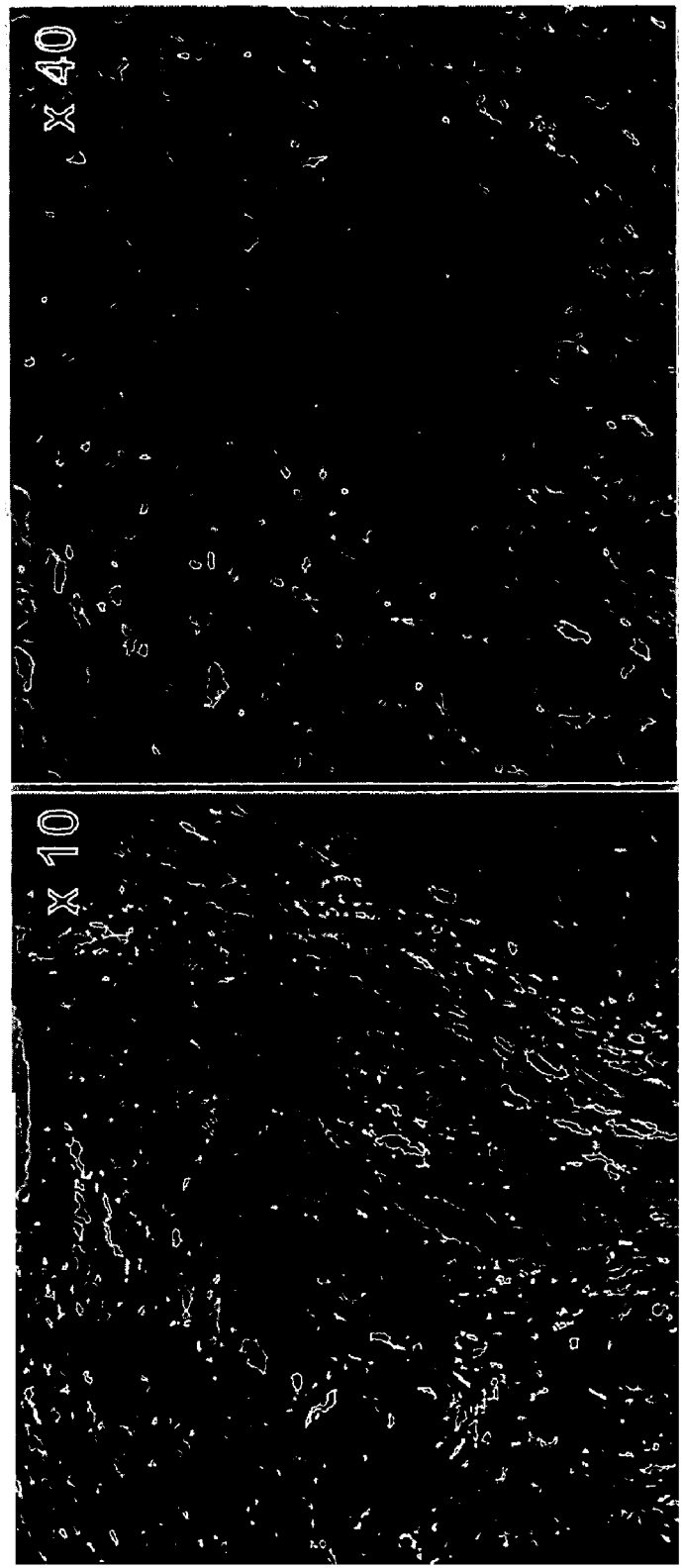
FIG. 5 is a microscopic photograph of human endometrial stromal sarcoma.

FIG. 3 is a microscopic photograph showing the normal human uterine smooth muscle tissue, FIG. 4 is a microscopic photograph showing the human uterine leiomyoma and human uterine leiomyosarcoma, and FIG. 5 is a microscopic photograph showing the human endometrial stromal sarcoma.

Ten cases of normal uterine smooth muscle, 6 cases of uterine leiomyoma, 6 cases of endometrial sarcoma, 3 cases of uterine leiomyosarcoma (low-malignancy), and 4 cases of uterine leiomyosarcoma (high-malignancy) evaluated via the above-described microscopic observation were subjected to immunohistochemical assay to inspect LMP2 expression of each tissue.

Immunohistochemical assay was carried out in the above-described manner.

Figure 6:
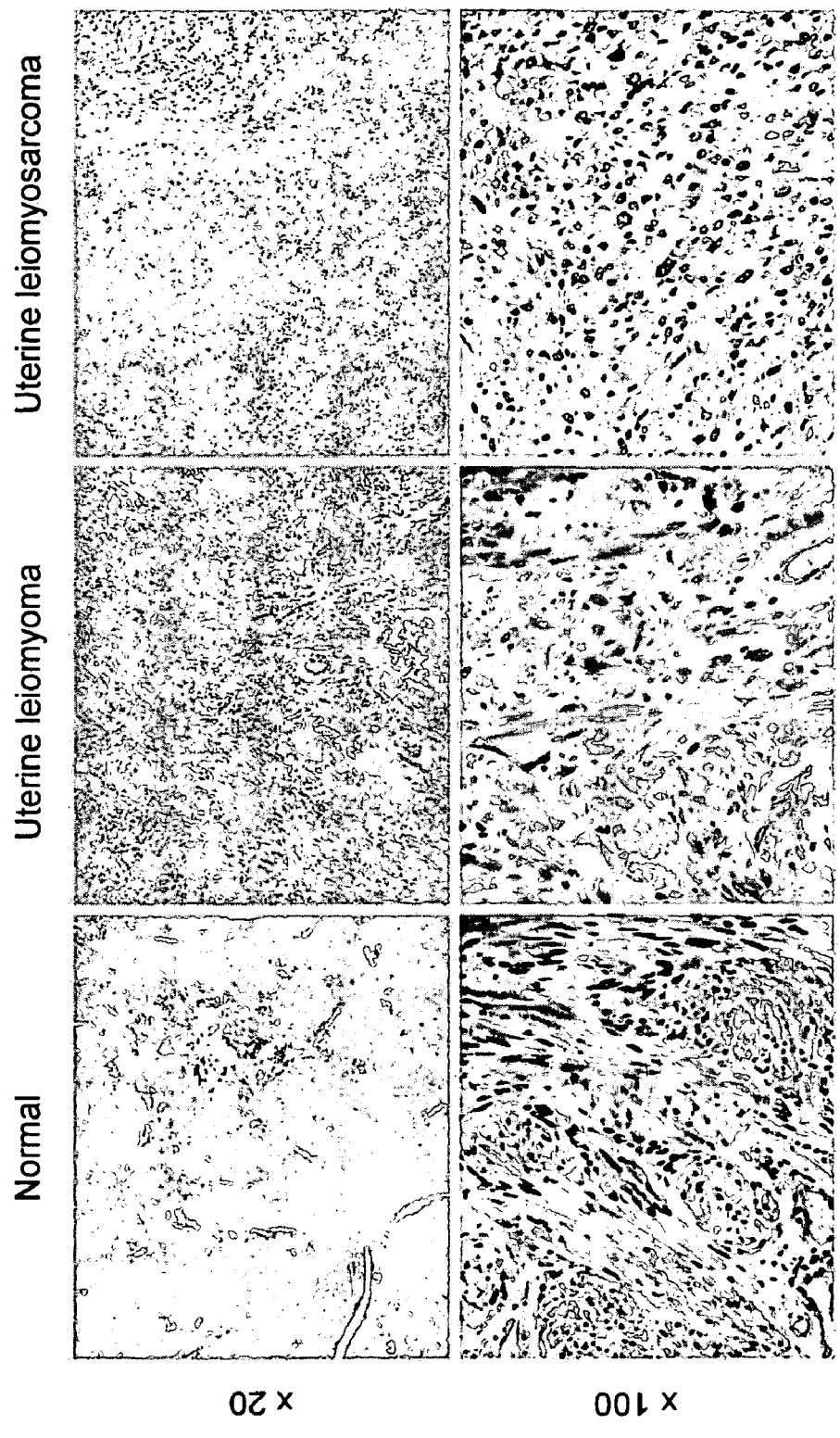
FIG. 6 is a photograph showing the results of immunohistochemical staining of normal uterine smooth muscle, uterine leiomyoma, and uterine leiomyosarcoma.

FIG. 6 is a photograph showing the results of immunohistochemical staining of the normal uterine smooth muscle, uterine leiomyoma, and uterine leiomyosarcoma. As shown in the figure, the normal uterine smooth muscle and uterine leiomyoma were stained, which verified expression of LMP2. Since uterine leiomyosarcoma was not stained, LMP2 expression was not verified.

Figure 7:
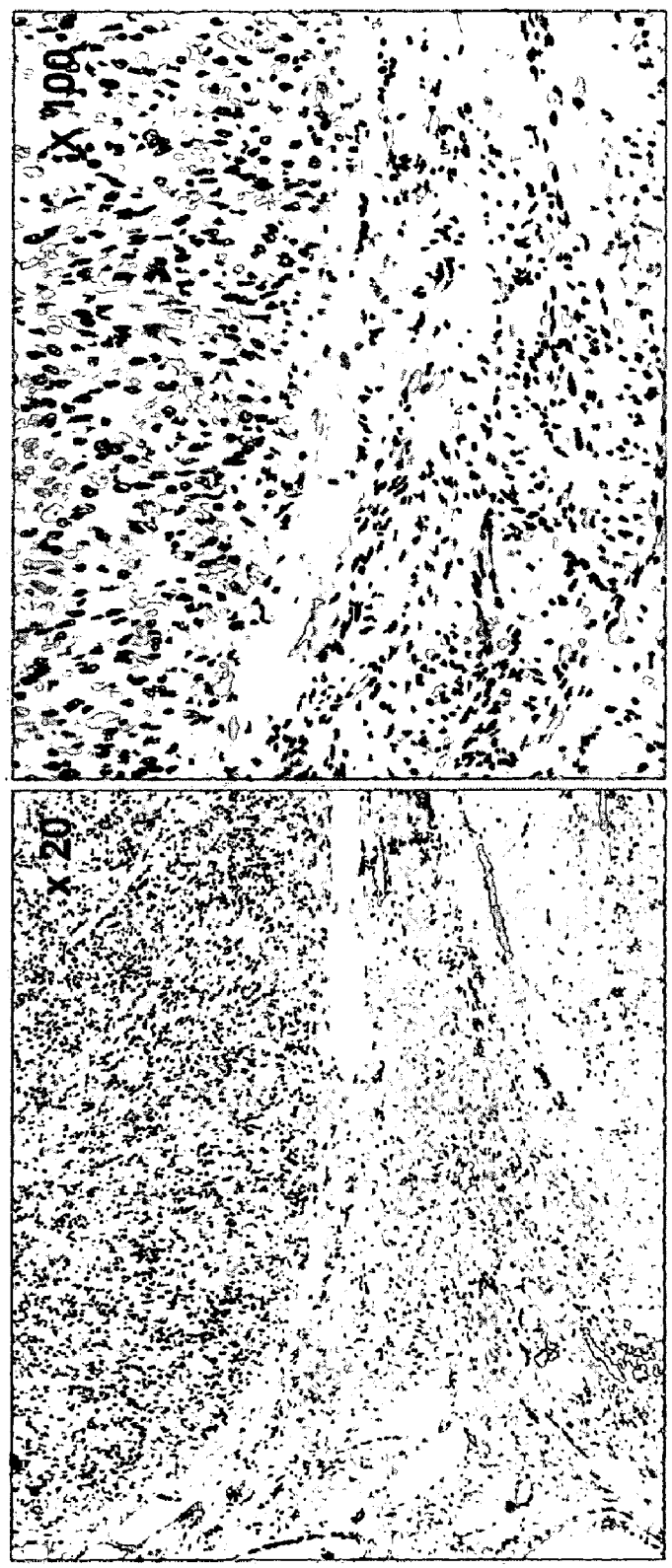
FIG. 7 is a photograph showing the results of immunohistochemical staining of a uterine leiomyosarcoma site and a normal uterine smooth muscle site in the same tissue. Lowering in LMP2 expression is observed at the uterine leiomyosarcoma site.

FIG. 7 is a photograph showing the results of immunohistochemical staining of uterine leiomyosarcoma. As shown in the figure, there were a region that was stained and a region that was not stained within the same tissue.

The conditions of LMP2 expression in the tissue are as shown below. The symbol; "+" indicates a positive result, the symbol "−" indicates a negative result, and the symbol "−/+" indicates results in the gray area.

|  | LMP2 expression |
| --- | --- |
| Normal uterine smooth muscle tissue | ++++ |
| Uterine leiomyoma tissue | ++++ |
| Endometrial sarcoma tissue | −/+ |
| Uterine leiomyosarcoma (low-malignancy) tissue | −/+ |
| Uterine leiomyosarcoma (high-malignancy) tissue | − |

As shown in the table, a significant lowering in LMP2 expression was observed only in the malignant tumor (uterine leiomyosarcoma). A lowering in the LMP2 expression level in uterine leiomyosarcoma tissue depends on malignancy. Thus, it was demonstrated that a lowering in the LMP2 expression level could be the indicator of malignancy of uterine leiomyosarcoma.

EXAMPLE 3

Forced Expression of LMP2 in SKN Cells

1. Changes in Cellular Morphology Upon Forced Expression of LMP2 in SKN Cells

Whether or not a lowering in LMP2 expression was directly correlated with transformation (canceration) in uterine smooth muscle cells was examined. LMP2 was forced to express via genetic recombination in the uterine leiomyosarcoma (SKN) cells in which no LMP2 expression was observed, and the configuration of SKN cells was observed.

Method

The LMP2 expression plasmid vector (2 μg) was introduced into $5 \times 10^5$ SKN cells using FuGene6 (Roche, Indianapolis, Ind.) in accordance with the manufacturer's protocol.

Figure 8:
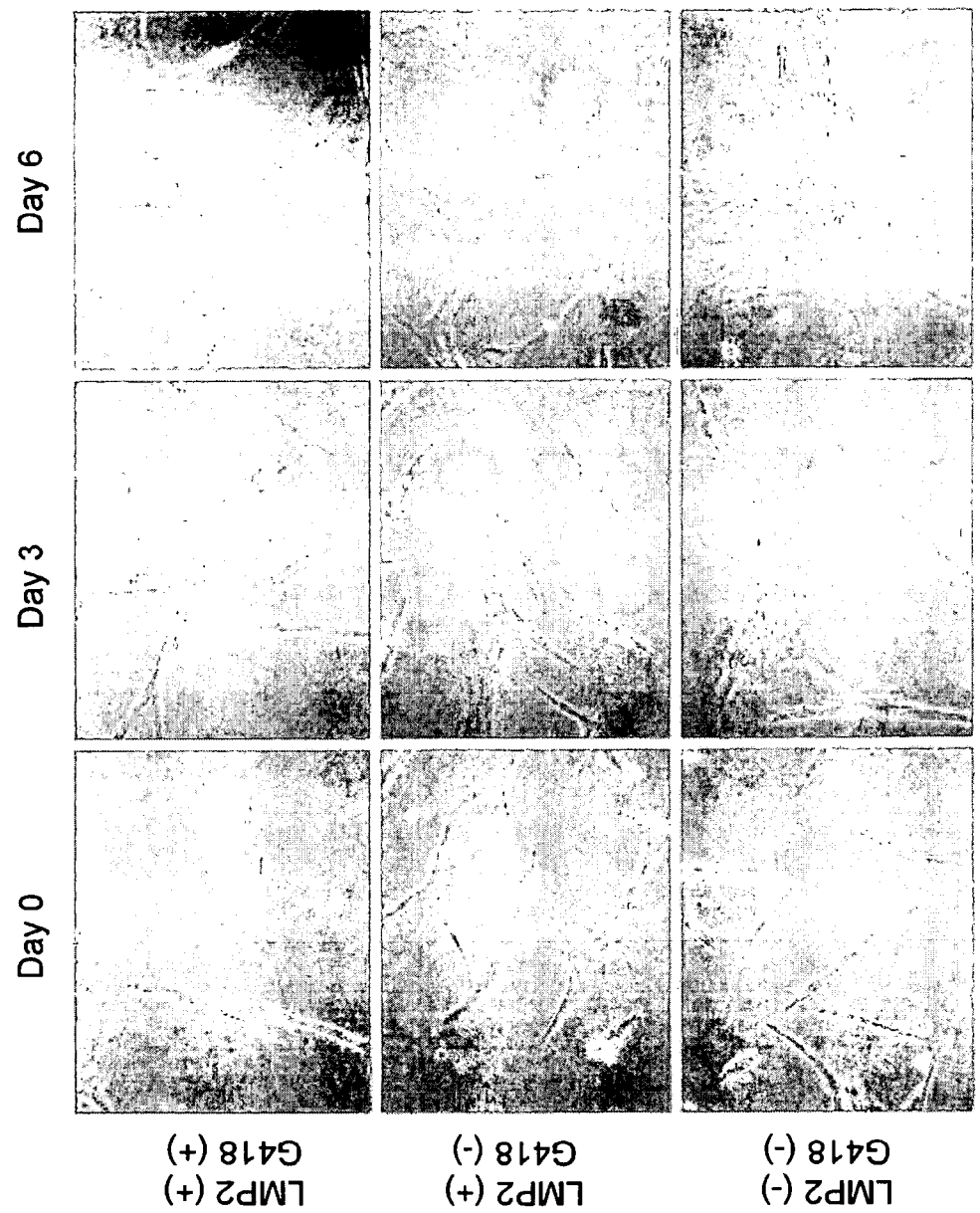
FIG. 8 is a photograph showing changes in the configuration of uterine leiomyosarcoma (SKN) cells upon forced expression of LMP2 via gene recombination in SKN cells in which no LMP2 expression is observed (Part 1).
Figure 9:
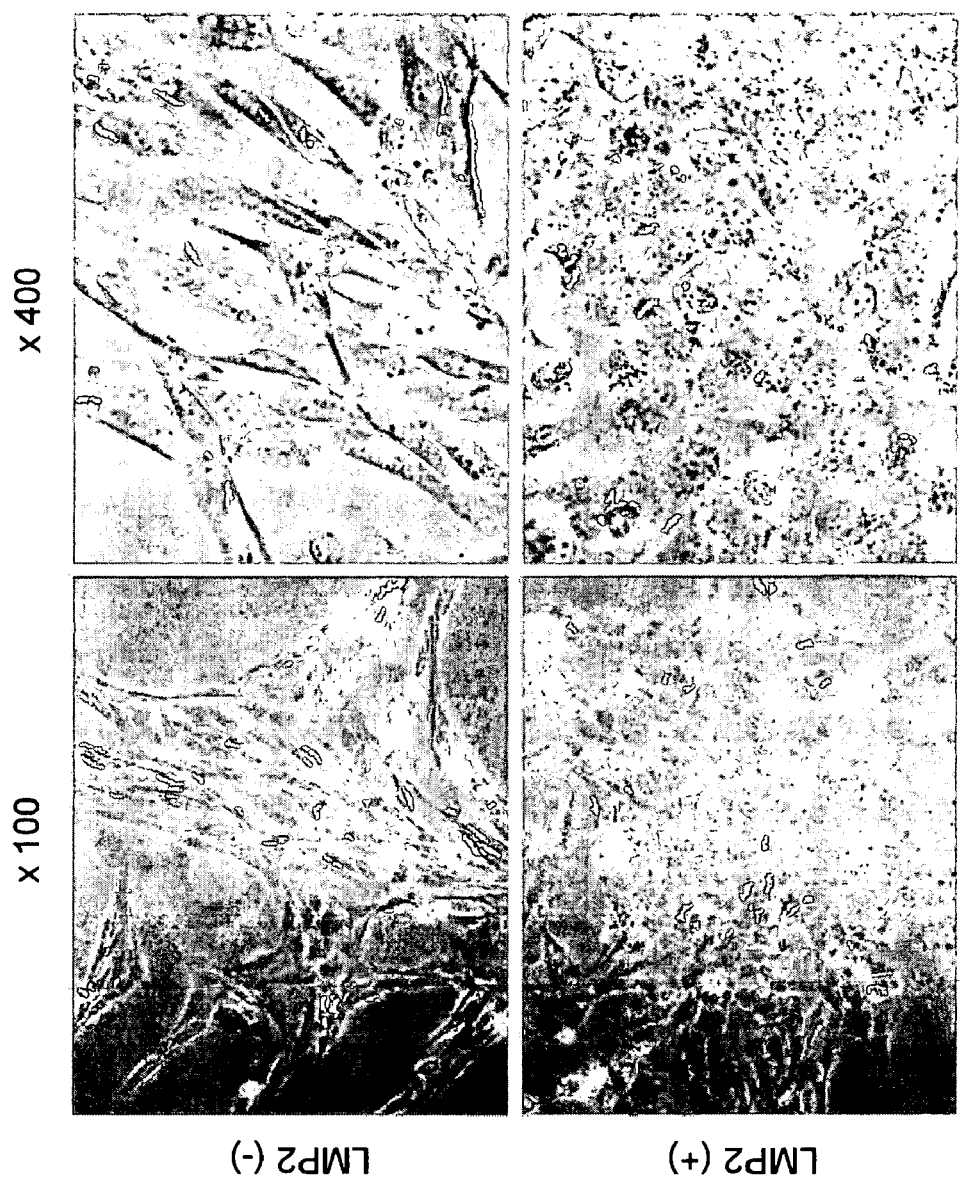
FIG. 9 is a photograph showing changes in the configuration of uterine leiomyosarcoma (SKN) cells upon forced expression of LMP2 via gene recombination in SKN cells in which no LMP2 expression is observed (Part 2).

G418 (neomycin) was added to the culture solution 3 days after the introduction of the plasmid vector into the cell (final concentration: 200 μg/ml), and SKN cells into which the LMP2 expression plasmid vector had been introduced were exclusively selected. The cell proliferative capacity and the cell morphogenic capacity of SKN cells in which LMP2 genes had been forced to express were examined. The results are shown in FIGS. 8, 9, and 21. As shown in FIGS. 8, 9, and 21, the SKN cell proliferative rate was 15.2 hours in terms of a doubling time. However, the proliferative capacity of SKN cells in which LMP2 had been forced to express was 17.5 hours in terms of a doubling time. LMP2 expression delayed the SKN cell proliferative rate by 2 hours in terms of a doubling time. Also, narrow rhomboid morphology of SKN cells were found to be converted into flat revertant-like morphology (i.e., rhomboid) by forced expression of LMP2.

2. Change in Fibronectin Expression Upon Forced Expression of LMP2 in SKN Cells

In highly malignant cancer cells having a metastatic capacity, in general, expression levels of intercellular adhesion factors (i.e., fibronectin) are significantly lowered. LMP2 was forced to express via genetic recombination in the uterine leiomyosarcoma (SKN) cells in which no LMP2 expression was observed, and changes in fibronectin expression were examined.

LMP2 was forced to express in the same manner as in Example 3. Fibronectin expression was examined via immunostaining using the anti-fibronectin antibody (Rockland). As control samples, normal human uterine smooth muscle cells (HuUSMC) were used.

Figure 10:
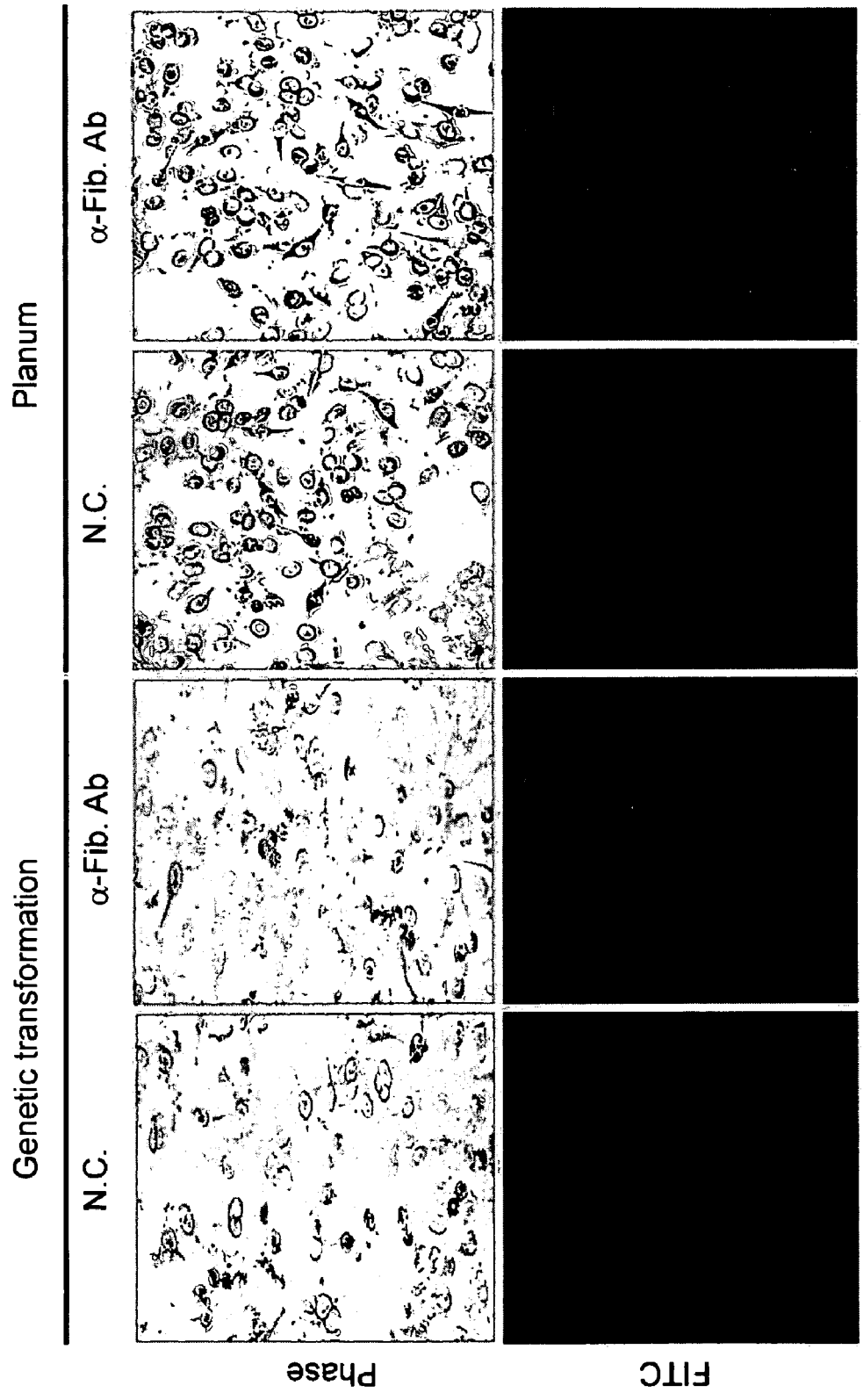
FIG. 10 is a photograph showing changes in fibronectin expression in uterine leiomyosarcoma (SKN) cells upon forced expression of LMP2 via gene recombination in SKN cells in which no LMP2 expression is observed.
Figure 11:
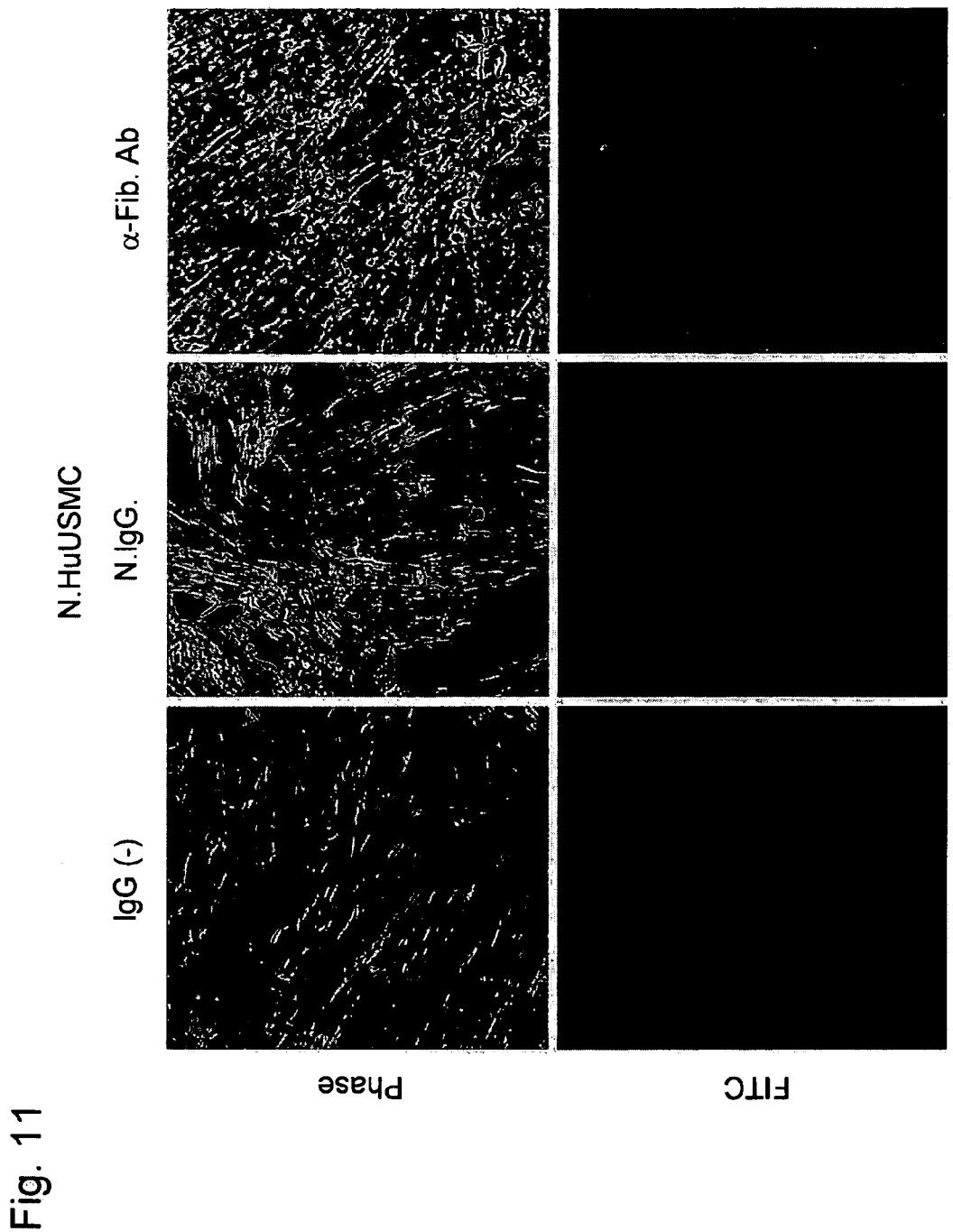
FIG. 11 is a photograph showing changes in fibronectin expression in normal human uterine smooth muscle cells (HuUSMC).

FIG. 10 shows the results regarding SKN cells, and FIG. 11 shows the results regarding human HuUSMC. FIG. 12 shows a summary of changes in morphology, cell proliferative rate, and fibronectin expression in each cell.

When LMP2 was forced to express in SKN cells, the morphology and the proliferative rate of SKN cells became similar to those of normal uterine smooth muscle cells, as shown in the figures. When LMP2 was forced to express in SKN cells, induction of fibronectin expression was found to be significant. This indicates that fibronectin expression induced by forced expression of LMP2 may attenuate the metastatic potential of SKN cells.

EXAMPLE 4

LMP2 Expression in Tissue

LMP2 expression is usually observed not only in uterine smooth muscle tissue but also in the skeletal muscle tissue and the cardiac muscle tissue. However, a lack of LMP2 causes leiomyosarcoma only in uterine smooth muscle tissue. Accordingly, LMP2 expression in the skeletal muscle, the cardiac muscle, and the smooth muscle was inspected. Also, LMP2 expression in the skeletal muscle, the cardiac muscle, and the smooth muscle of mice each lacking the Rag1 gene necessary for the immunomechanism was inspected.

Immunohistochemical assay was carried out using paraffin-embedded samples of 1-day-old newborn mice in accordance with the method described above.

Figure 13:
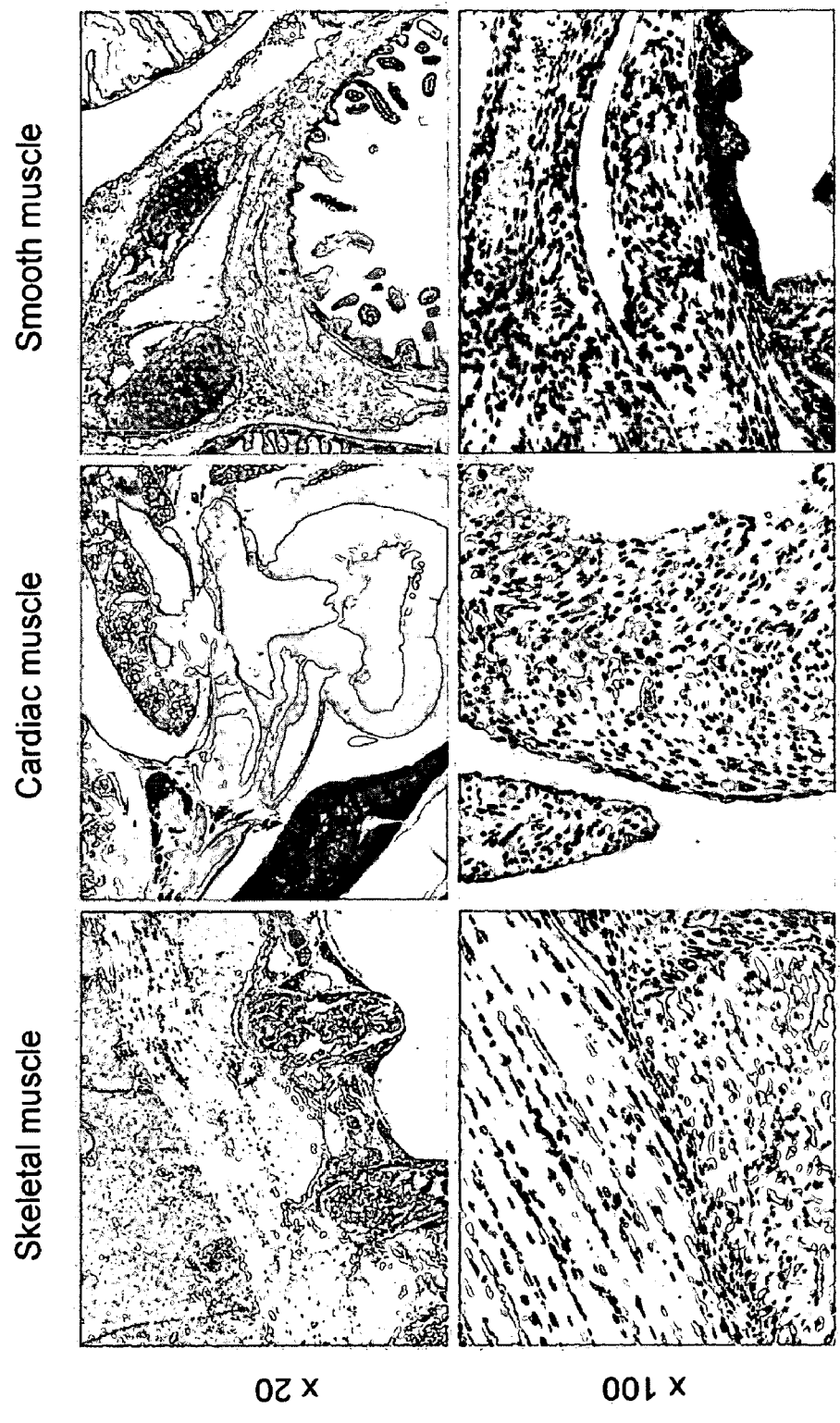
FIG. 13 is a photograph showing LMP2 expression in murine skeletal muscle tissue, cardiac tissue, and smooth muscle tissue.

FIG. 13 is a photograph showing the results of immunohistochemical staining.

EXAMPLE 5

LMP2 Expression in Leiomyosarcoma Tissue of Uterus and Other Organs

In the human uterine leiomyosarcoma tissue, significant loss of LMP2 expression was observed. Leiomyosarcoma develops in various organs other than in the uterus. Thus, whether or not loss of LMP2 expression would be observed specifically for uterine leiomyosarcoma was examined.

Method

Four cases of uterine leiomyosarcoma (high-malignancy), 4 cases of uterine leiomyosarcoma (low-malignancy), 1 case of leiomyosarcoma in the uterine epithelium, 1 case of endometrial stromal sarcoma, 1 case of uterine leiomyoma, 1 case of normal uterine smooth muscle, 1 case of primary retroperitoneal leiomyosarcoma, 1 case of primary omental leiomyosarcoma, 1 case of primary leiomyosarcoma of the small intestine, and 1 case of primary mesenteric leiomyosarcoma were selected from the pathological file. LMP2 expression in the affected tissue samples was examined via immunohistological staining using the anti-human LMP2 antibody.

Significant LMP2 expression observed in normal uterine smooth muscle tissue or the uterine leiomyoma tissue (a benign tumor) was found to be significantly attenuated in uterine leiomyosarcoma tissue (a malignant tumor), as shown in FIG. 14. Although LMP2 expression was not observed in a case of endometrial stromal sarcoma, significant LMP2 expression was observed in a case of endometrial stromal sarcoma. In leiomyosarcoma that developed in the abdominal and digestive tissue, significant LMP2 expression is occasionally observed; however, such expression is occasionally significantly attenuated. Gene copy number profiling by genomic analysis that had been conducted up to the present indicates that the uterine leiomyosarcoma developing mechanism may be very different from the leiomyosarcoma developing mechanism in other organs. The results of Example 5 indicate that loss of LMP2 expression may be observed specifically in uterine leiomyosarcoma.

EXAMPLE 6

Correlation of Mutation of IFN-γ Signal Transduction Factor and Uterine Leiomyosarcoma The condition such that "significant attenuation of LMP2 expression observed specifically in uterine leiomyosarcoma" was examined again and such specificity was confirmed. More specifically, 21 cases of normal human uterine smooth muscle tissue, 24 cases of uterine leiomyoma, 6 cases of endometrial stromal sarcoma, and 29 cases of uterine leiomyosarcoma were subjected to immunohistological staining using the anti-human LMP2 antibody to examine LMP2 expression. As shown in FIG. 18, significant attenuation in LMP2 expression that is observed specifically in uterine leiomyosarcoma was confirmed.

LMP2 expression is significantly induced by IFN-γ stimulation as shown in FIG. 15. Significant attenuation of LMP2 expression observed specifically in uterine leiomyosarcoma may result from inactivation caused by mutation or lack of promoter regions of IFN-γ signal transduction factors, i.e., JAK1, JAK2, STAT1, PKC-, PI3K, and LMP2. Thus, mutations in the promoter regions of the IFN-γ signal transduction factors, JAK1, JAK2, STAT1, and LMP2, were examined.

Method

The leiomyosarcoma tissue and the normal smooth muscle tissue were selectively excised via laser microdissection and recovered from 13 cases of surgically removed tissues of human uterine bodies. A total of 14 specimen samples; i.e., 13 normal uterine smooth muscle tissue samples and a cultured cell sample of the normal human uterine smooth muscle, were used. Also, a total of 14 specimen samples; i.e., 13 uterine leiomyosarcoma tissue samples and a cultured cell sample of human uterine leiomyosarcoma, were used. Thus, mutations in promoter regions of JAK1, JAK2, STAT1, and LMP2 were examined. The samples were added to an HMW solution (10 mM Tris-HCl (pH 8.0), 150 mM NaCl, 10 mM EDTA-NaOH (pH 8.0), 0.1% SDS)-proteinase K (100 μg/ml), the resultant was heated at 55° C. for 24 hours, and impurities were eliminated with the aid of phenol/chloroform to purify genomic DNA. In order to determine the nucleotide sequences of the gene region (A) encoding the ATP-binding region in the JAK1 molecule and the gene region (B) encoding the tyrosine phosphorylation enzyme activation region, PCR-primers reacting with the relevant regions of the gene region (A) and the gene region (B) were used to amplify DNA fragments comprising relevant regions with the use of genomic DNAs obtained from the specimen samples by PCR. The PCR-amplified DNA fragments were extracted and purified via agarose gel electrophoresis, and the nucleotide sequences were determined using a sequencer (ABI Prism3100 Genetic Analyzer). In the same manner as in the case in which the nucleotide sequence of JAK1 was determined, the nucleotide sequence of a gene region (C) encoding the ATP-binding region in the JAK2 molecule and of a gene region (D) encoding a tyrosine phosphorylation enzyme activation region, the nucleotide sequence of a gene region (E) encoding the transcription factor activation region in the STAT1 molecule (i.e., a region between tyrosine 701 and serine 727), and the nucleotide sequence of a gene region (F) encoding the promoter region of LMP2 were determined. In order to detect mutations observed specifically in uterine leiomyosarcoma, the nucleotide sequences (region A to region E) were compared and examined between the uterine leiomyosarcoma tissue and the normal uterine smooth muscle tissue in the same uterine body.

The results of analysis of mutations in the phosphorylation enzyme or transcription factor activation region and the LMP2 promoter regions caused by the IFN-γ signal transduction factors, i.e., JAK1, JAK2, and STAT1, are shown in FIG. 16 (a summary of mutations regarding each sample) and in FIG. 17 (a summary of mutations regarding each factor).

EXAMPLE 7

Influence of Constitutive Expression of LMP2 on Cellular Morphology and Cell Proliferation in Human Uterine Leiomyosarcoma Cell Significant lowering in LMP2 expression is observed in human uterine leiomyosarcoma tissue. Thus, whether or not lowered LMP2 expression would be associated with development of uterine leiomyosarcoma was examined.
Method SKN cells were cultured on a 6-well plate, and 2 ml of Ham's F-12-15% Fcs culture solution was exchanged when the cells reached 70% confluence. On the following day, 2 μg of pCEM9 vector (containing no LMP2 gene) or pCEM-LMP2 vector (containing the LMP2 gene) was transfected into SKN cells per well using the FuGENE6 (Roche) in accordance with the manufacturer's protocol. The vector-transfected SKN cells were cultured in a $CO_2$ incubator at 37° C. for 48 hours, SKN cells were peeled via trypsin treatment, and the peeled cells were cultured in a 100-mm culture petri dish placed in a $CO_2$ incubator at 37° C. for 48 hours. Thereafter, culture was conducted in the Ham's F-12-15% Fcs culture solution comprising 100 μg/ml of G418 (neomycin). After the cells were cultured in a $CO_2$ incubator at 37° C. for 2 weeks, SKN cells into which pCEM9 vector or pCEM-LMP2 vector had been transfected selectively survived with the aid of G418, proliferated, and formed colonies. After selective culture had been conducted in a G418 (neomycin)-containing culture solution for 3 weeks, the number of colonies formed by SKN cells into which the vectors had been transfected in the 100-mm culture petri dish was determined. Cellular morphology of SKN cells was also observed.

Figure 20:
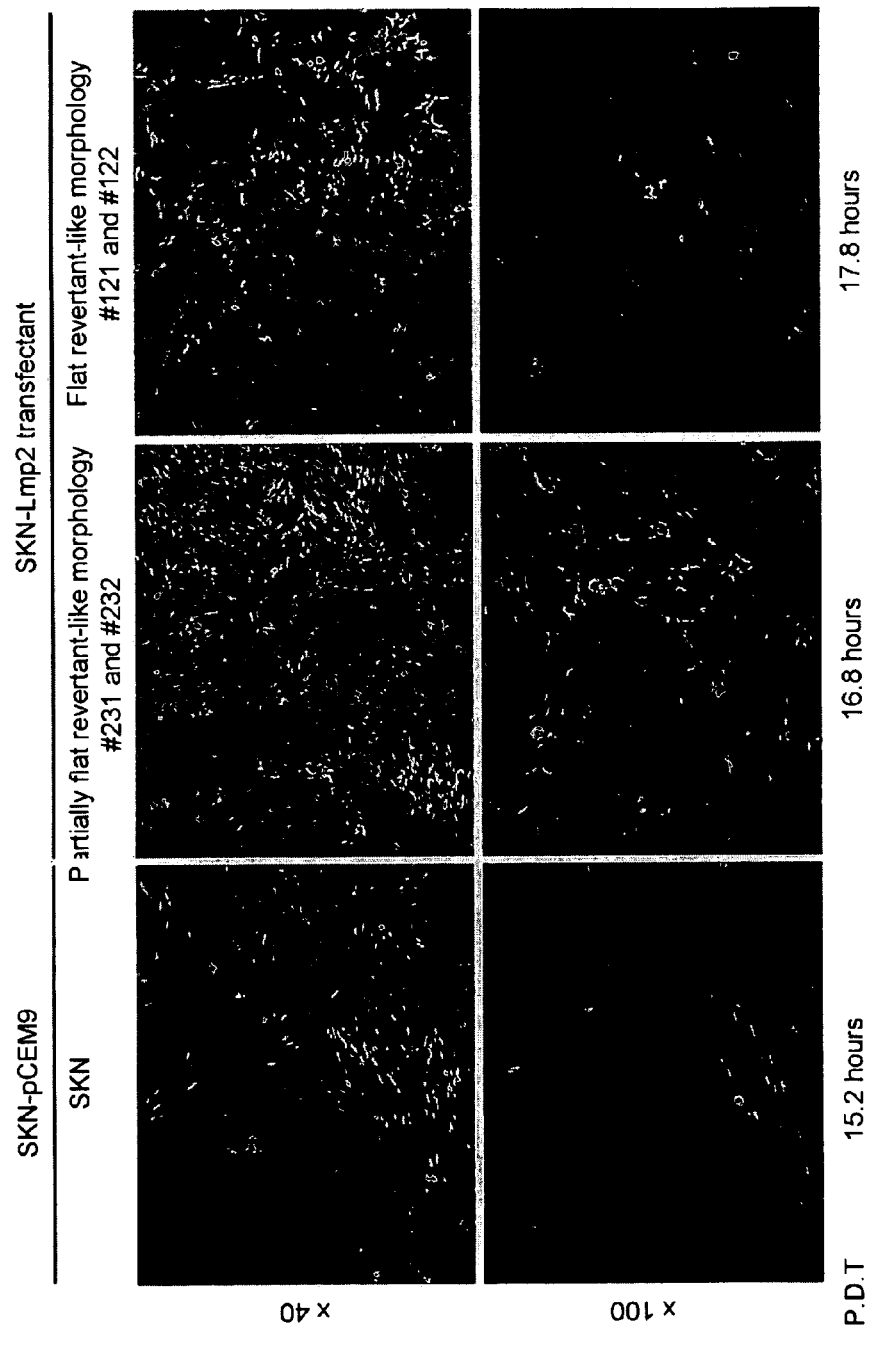
FIG. 20 is a photograph showing changes in morphology of uterine leiomyosarcoma (SKN) cells upon forced expression of LMP2 via gene recombination in SKN cells in which no LMP2 expression is observed.

As shown in FIG. 9 and FIG. 20, the morphology of SKN cells into which the pCEM-LMP2 vector had been transfected were found to be converted into flat revertant-like morphology. Generally, (A) colonies consisting of cells that maintain original morphology of SKN cells, (B) colonies comprising some cells having morphologies that have converted into those of flat revertants, and (C) colonies consisting of cells having morphologies that have converted into those of flat revertants were found. The numbers of colonies each belonging to categories (A), (B), and (C) are shown in FIG. 19. The proliferative rates of cells of categories (A), (B), and (C) were examined via trypan blue staining. As a result, the population doubling time (P.D.T.) of category (A) was found to be 15. 2 hours, P.D.T. of category (B) was found to be 16.8 hours, and P.D.T. of category (C) was found to be 17.8 hours. In the cultured human uterine leiomyosarcoma SKN cells, constitutive expression of LMP2 was found to convert the morphology into flat revertant-like morphology, and cell proliferative rate was found to be delayed (FIGS. 9, 20, and 21).

In general, the intercellular connections of cells become loose in highly malignant cancer cells having metastatic potentials, and proliferation can be realized with a single cell. In particular, expression of fibronectins that form the intercellular matrix structure is known to become significantly lower in highly malignant cancer cells having metastatic potentials. Since SKN cells are highly malignant leiomyosarcoma cells having metastatic potentials, fibronectin expression is considered to be significantly low. Thus, SKN cells of categories (A), (B), and (C) were cultured in the Labtech Chamber Slide (IWAKI), 80% confluence was confirmed under a microscope, and the expression conditions of fibronectins were examined using the anti-human-fibronectin antibody (Rockland) in accordance with a conventional technique. As shown in FIG. 10 and FIG. 11, it was found that fibronectin expression was significant and that fibronectins formed the matrix structure in the cultured normal human uterine smooth muscle cells (N.HuUSMC). In cultured human uterine leiomyosarcoma (SKN) cells, however, fibronectin expression was weak, and formation of the matrix structure was not observed. Fibronectin expression was induced by constitutive expression of LMP2 in the flat revertant-like SKN cells, although formation of the matrix structure by fibronectins was not observed (FIG. 10). FIG. 21 summarizes the results regarding the influences of constitutive expression of LMP2 on cellular morphology, cell proliferation, and fibronectin expression in SKN cells.

Figure 22:
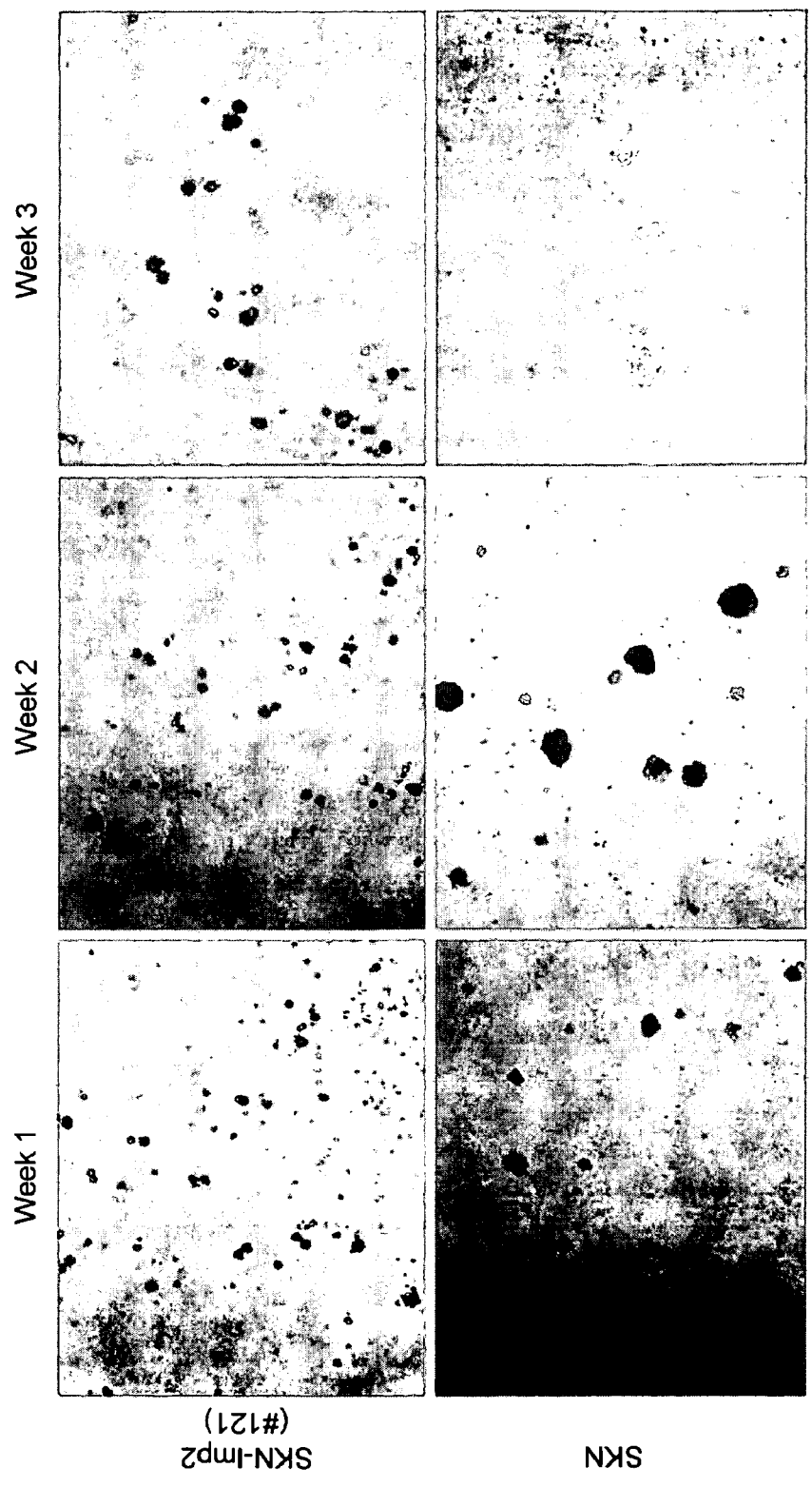
FIG. 22 is a photograph showing that SKN cells in which LMP2 is constitutively expressed significantly decrease colony formation, which is an indicator of capacity for tumorigenesis.
Figure 23A:
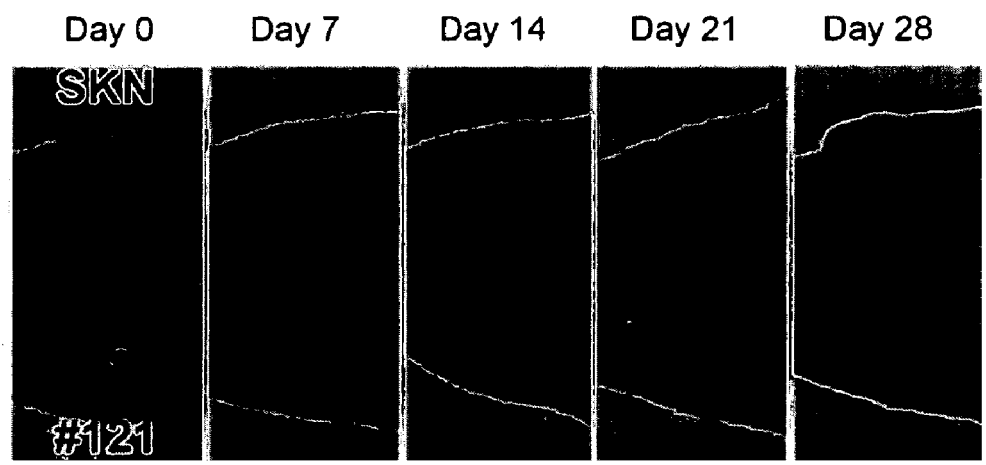
FIG. 23A is a photograph showing that SKN cells in which LMP2 is constitutively expressed significantly decrease capacity for tumorigenesis via a transplant experiment involving nude mice.
Figure 23B:
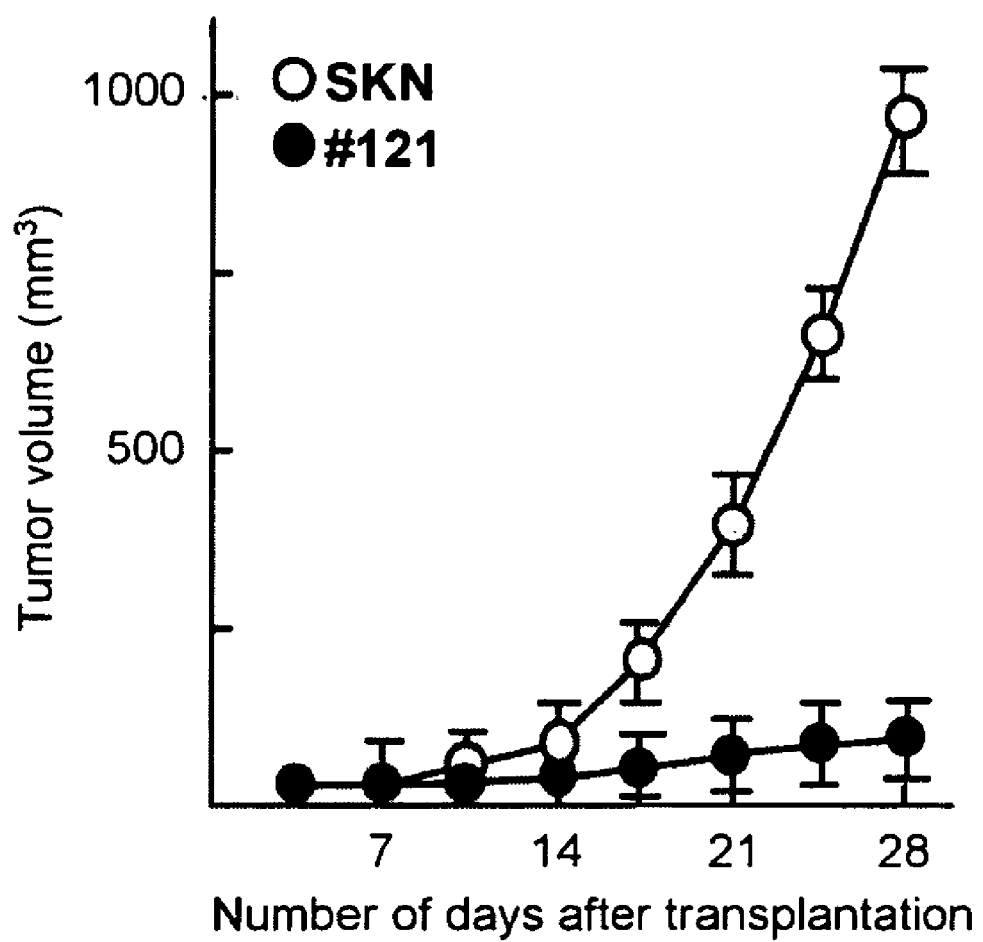
FIG. 23B is a photograph showing that SKN cells in which LMP2 is constitutively expressed significantly decrease capacity for tumorigenesis via a transplant experiment involving nude mice.

As shown in FIG. 21, the tumorigenic potentials that SKN cells originally have are deduced to become significantly lower upon LMP2 expression. Thus, the colony-forming potentials that can serve as an indicators of the tumorigenic potentials in the flat revertant-like SKN cells (SKN-lmp2 cells) and SKN cells (SKN-pCEM9 cells) were examined using a 24-well Low Attachment Flat Chamber (Costor). SKN-lmp2 cells (#121) ($1 \times 10^4$ cells) or SKN-pCEM9 cells ($1 \times 10^4$ cells) were cultured per well of the 24-well Low Attachment Flat Chamber (Costor), and colony formation was observed under a microscope. As shown in FIG. 22, the SKN-pCEM9 cells were found to form large colonies and proliferate 3 weeks after the initiation of culture. In contrast, the SKN-lmp2 cells formed colonies; however, such colonies were apparently smaller than those formed by the SKN-pCEM9 cells. This indicates that the proliferation potential is low. As a result of an experiment using the Low Attachment Flat Chamber, SKN-lmp2 cells (colony #121) were found to have small colony-forming potentials. Thus, tumorigenic potentials were found to be significantly lowered. Thus, immunodeficient nude mice (Nippon Clea Co.) were used to examine the tumorigenic potentials in the SKN-pCEM9 cells and in the SKN-lmp2 cells (colony #121). Five female nude mice (6-week-old, Nippon Clea Co.) were purchased, SKN-pCEM9 cells ($1\times10^6$ cells) were intracutaneously injected into the right sides of the backs of mice, SKN-lmp2 cells (#121) ($1\times10^5$ cells) were intracutaneously injected into the left sides of the backs of mice, and tumorigenesis was observed with the elapse of time. The SKN-pCEM9 cells ($1\times10^6$ cells) were found to proliferate intracutaneously in the nude mice 4 weeks after intracutaneous injection, and significant tumorigenesis was observed (tumor volume: 980 mm$^3$). In contrast, the SKN-lmp2 cells (colony #121) ($1\times10^5$ cells) did not proliferate intracutaneously in the nude mice, and significant tumorigenesis was not observed (tumor volume: 90 mm$^3$) (FIGS. 23A and 23B). It was confirmed that constitutive expression of LMP2 would significantly decrease tumorigenic potentials in the cultured human uterine smooth muscle (SKN) cells (FIGS. 23A to 23C).

EXAMPLE 8

Significant Cyclin E Expression in Uterine Leiomyosarcoma

Constitutive LMP2 expression in the cultured human uterine smooth muscle (SKN) cells produced the three 3 biological features: (1) SKN cellular morphology converted into that of flat revertants; (2) a significantly lowered proliferative rate of SKN cells; and (3) significantly lowered tumorigenic potentials of SKN cells. Thus, gene expression profiling was performed on SKN-pCEM9 cells and SKN-lmp2 cells to inspect the types of factors, expression patterns of which would be significantly influenced by constitutive LMP2 expression in SKN cells.
Method
SKN-pCEM9 cells and SKN-lmp2 cells were cultured on four 100-mm petri dishes each in the CO$_2$ incubator at 37° C. until they reached 80% confluence ($2\times10^6$ cells proliferated per petri dish). The cells were peeled and recovered with the aid of trypsin and the cells were washed with 1× PBS. The cells were lysed in 2 ml of TRIsol (Invitrogen) per petri dish while mildly shaking for 10 minutes so as to completely dissolve cells in TRIsol. Chloroform (200 µl) was added to 1 ml of the TRIsol solution, and the resultant was mildly shaken for 10 minutes. After shaking for 10 minutes, centrifugation was carried out at 7,000 rpm at room temperature for 20 minutes, an aqueous phase was separated from an organic phase, and an aqueous phase was collected while refraining from collecting an intermediate layer. Total RNA contained in the aqueous phase was purified in accordance with a known technique. As a result, 152.3 µg of total RNA was obtained from the SKN-pCEM9 cells, and 128.8 µg of total RNA was obtained from the SKN-lmp2 cells. Thereafter, 100 µg each of both total RNA samples were prepared and subjected to gene expression profiling.
FIG. 24 shows part of the results of microarray gene expression profiling. Cyclin E, significant expression of which was observed in the SKN-pCEM9 cells, was not substantially expressed in the SKN-lmp2 cells. This indicates that expression of cyclin E that would significantly induce cell proliferation via constitutive expression of LMP2 was significantly lowered in SKN cells.

Figure 25:
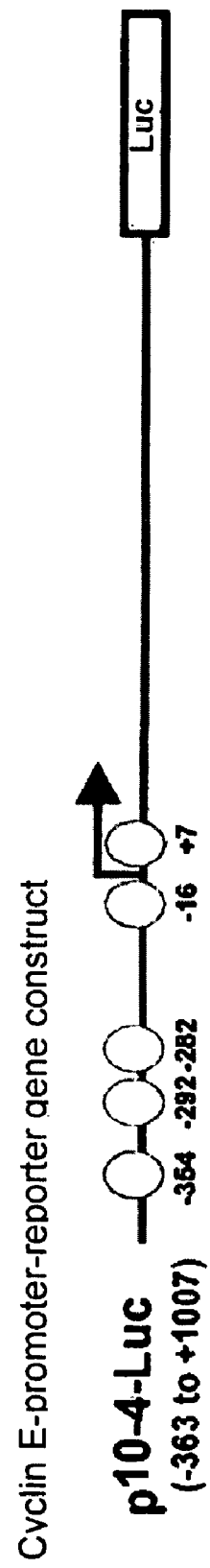
FIG. 25 shows the structure of a luciferase reporter gene comprising a cyclin E promoter.
Figure 26:
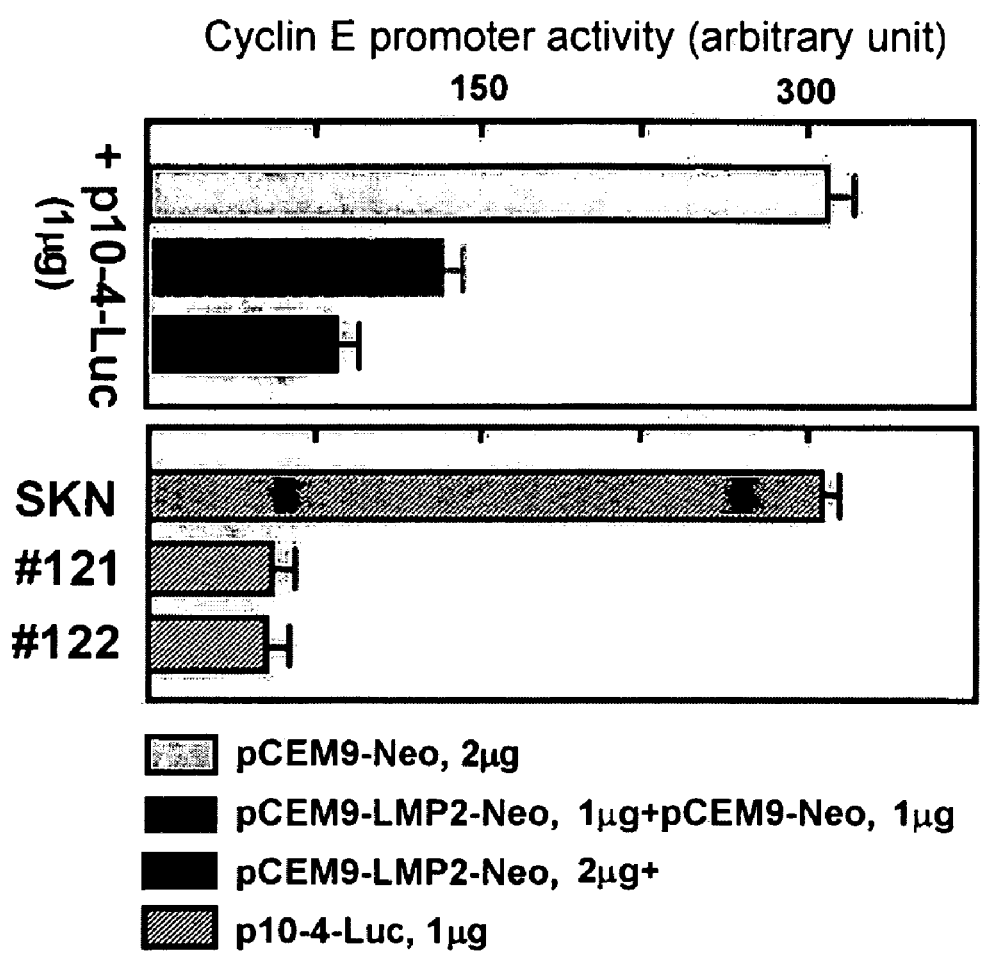
FIG. 26 shows cyclin E promoter activity in SKN cells in which SKN cells and LMP2 are constitutively expressed (colony #121 and #122). The expression level of cyclin E observed to be significant in the cultured uterine leiomyosarcoma SKN cells was significantly lowered via constitutive expression of LMP2.
Figure 27:
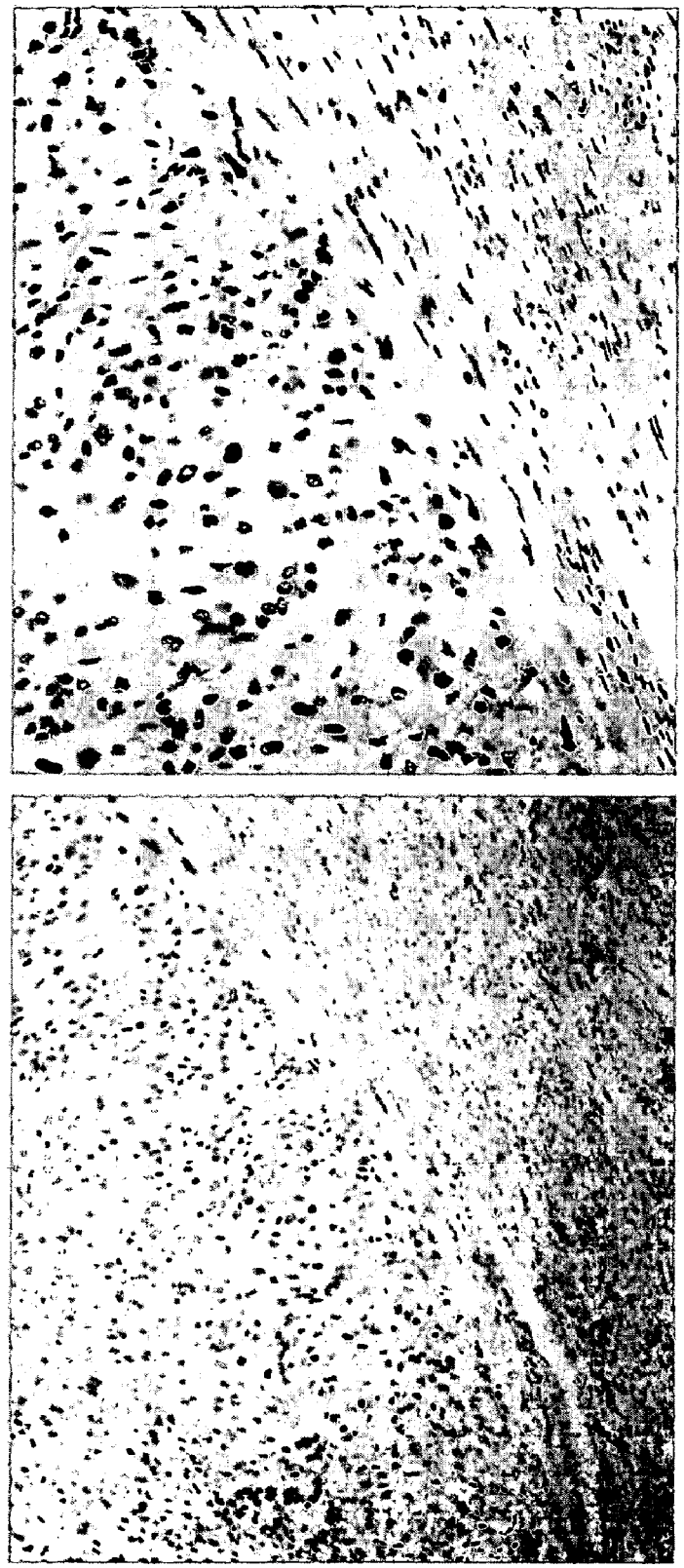
FIG. 27 is a photograph showing the results of tissue staining that demonstrate significant cyclin E expression in human uterine leiomyosarcoma tissue. Cyclin E expression is not observed in normal uterine smooth muscle layer; however, significant cyclin E expression is observed in malignant tumor tissue (human uterine leiomyosarcoma tissue).

Transfection and Reporter Assay
FIG. 25 shows a structure of a reporter plasmid (p10-4-Luc) (provided by Dr. E A. Thompson of the Department of Cancer Biology, Mayo Clinic Comprehensive Cancer Center) in which expression of the luciferase gene is induced upon activation of cyclin E promoter region. In accordance with the figure, the p10-4-Luc reporter plasmid and the LMP2 expression plasmid pCEM9-Lmp2 (2 µg in total) were transfected into SKN cells and SKN-lmp2 cells (clones #121 and #122) using the FuGENE 6 Transfection Reagent (Roche) in accordance with the manufacturer's recommendation. All the transfected DNA samples contained 200 ng of pCMVβ-Gal (Tropix) as the internal transfection efficiency control. After transfection, the cells were cultured in the CO$_2$ incubator at 37° C. for 48 hours. At the last stage, the cells were washed, lysed with 500 µl of lytic buffer, and then analyzed using the Dual-Luciferase Reporter Assay System (Promega) in accordance with the manufacturer's instructions.
The results shown below were obtained using the above materials and the above methods.
Promoter activity of cyclin E was significantly decreased via constitutive expression of LMP2 in the cultured human uterine leiomyosarcoma (SKN) cells.
FIG. 24 shows part of the results of microarray gene expression profiling. Cyclin E that was found to be significantly expressed in the SKN-pCEM9 cells are not substantially expressed in the SKN-lmp2 cells. Specifically, expression of cyclin E that would induce cell proliferation via constitutive expression of LMP2 was significantly lowered in SKN cells. Subsequently, it should be confirmed that constitutive expression of LMP2 would significantly suppress promoter activity of cyclin E in SKN cells. The effects of constitutive LMP2 expression on promoter activity of cyclin E were examined via reporter assay using 3 types of SKN cell lines (SKN-pCEM9, SKN-lmp2#121, and SKN-lmp2#122). In the absence of LMP2 expression, significantly activated cyclin E promoter activity was observed in SKN cells (FIG. 26). In the presence of LMP2 expression, significant activation of the cyclin E promoter was not observed (FIG. 26). In the SKN-pCEM9 cells, cyclin E promoter was significantly activated; however, such significant activation of cyclin E promoter was not observed in the SKN-lmp2 (FIG. 26). In the cultured human uterine leiomyosarcoma SKN cells, promoter activity of cyclin E was found to be significantly decreased via constitutive LMP2 expression.
FIG. 26 shows cyclin E promoter activity in SKN cells and in SKN cells in which LMP2 are constitutively expressed (clones #121 and #122). Significant cyclin E expression observed in the cultured uterine leiomyosarcoma SKN cells was significantly lowered via constitutive LMP2 expression. That is, LMP2 expression is not induced in SKN cells, and thus, expression of cyclin E, which is a cell proliferation inducer, may not be suppressed. Cells that lack cyclin E genes usually proliferate; however, it is apparent that such cells are resistant to transformation caused by external stimulus and the like. Accordingly, a lack of cyclin E expression regulation due to a lack of significant LMP2 expression induction is considered to be associated with development of human uterine leiomyosarcoma. The conditions of cyclin E expression in human uterine leiomyosarcoma tissue were examined via immunohistological staining using the anti-human cyclin E antibody. As shown in FIG. 27, cyclin E expression that is not observed in normal human uterine smooth muscle tissue is clearly observed in human uterine leiomyosarcoma tissue within the same tissue slice. The results of examination of 14 cases of human uterine leiomyosarcoma demonstrate that cyclin E expression is not observed in normal uterine smooth muscle layer and that significant expression of cyclin E is observed in the malignant tumor, i.e., the human uterine leiomyosarcoma tissue.

Figure 28:
FIG. 28 is a photograph showing the results of tissue staining that demonstrate cyclin E expression in the nucleus during the mitotic period in human uterine leiomyosarcoma tissue. In general, cyclin E, induces cell proliferation, is overexpressed in the cytoplasm at the G1 stage, which is the initiation period of cell proliferation, migrates immediately into the nucleus, and initiates the synthesis of chromosomes at the S stage. Thereafter, degradation of cyclin E starts immediately during the later half of the S stage. Accordingly, cyclin E expression is not observed at the G2 and M stages of normal cells; however, significant cyclin E expression is observed in the nucleus during the mitotic period in human uterine leiomyosarcoma tissue.

FIG. 28 is a photograph showing the results of tissue staining that demonstrate cyclin E expression in the nucleus during the mitotic period in human uterine leiomyosarcoma tissue. In general, cyclin E, induces cell proliferation, is overexpressed in the cytoplasm at the G1 stage, which is the initiation period of cell proliferation, migrates immediately into the nucleus, and initiates the synthesis of chromosomes at the S stage. Thereafter, degradation of cyclin E starts immediately at the last half of the S stage. Accordingly, cyclin E expression is not observed at the G2 and M stages of normal cells; however, significant cyclin E expression is observed in the nucleus during the mitotic period in human uterine leiomyosarcoma tissue. More specifically, cyclin E expression is useful as a marker for identifying human uterine leiomyosarcoma.

Industrial Applicability

Inspection of transcription or expression of LMP2 and/or cyclin E in uterine smooth muscle enables detection of whether or not uterine leiomyosarcoma has developed in uterine smooth muscle tissue. When the LMP2 transcription or expression level is significantly low and/or the cyclin E transcription or expression level is high, development of leiomyosarcoma can be diagnosed. In the past, uterine leiomyosarcoma had been detected using cellular morphology, density, proliferative rate, and other conditions as an indicators. According to the method of the present invention, uterine leiomyosarcoma can be detected easily and assuredly. Further, the method of the present invention enables identification of whether a tumor in uterine smooth muscle is uterine leiomyoma or uterine leiomyosarcoma and determination of malignancy of uterine leiomyosarcoma.

Further, uterine leiomyosarcoma can be detected assuredly by carrying out the method of the present invention involving the use of LMP2 and/or cyclin E as a marker in combination with a conventional method involving the use of cellular morphology, density, and other conditions as an indicators and/or a method involving the use of myosin as a marker.

Further, mutation of IFN-γ signal transduction factors; i.e., the JAK1 kinase gene, the STAT1 gene, and the LMP2 promoter, is closely correlated with development of uterine leiomyosarcoma. Thus, detection of mutation of such gene or promoter enables diagnosis of whether or not a patient is afflicted with uterine leiomyosarcoma and a patient is at risk of being afflicted with uterine leiomyosarcoma.

All publications, patents, and patent applications cited herein are incorporated herein by reference in their entirety.

The invention claimed is:

1. A method for differentiating human uterine leiomyosarcoma from human uterine leiomyoma using the degree of transcription or expression of LMP2 and cyclin E in uterine smooth muscle tissue as an indicator, wherein the method comprises:

preparing a human uterine smooth muscle tissue from a patient who is suffering from a human uterine smooth muscle tumor as a sample;

assaying transcription or expression of LMP2 and cyclin E in the human uterine smooth muscle tissue; and determining that the tumor is human uterine leiomyosarcoma when the LMP2 transcription or expression level is negative or lower than that in normal uterine smooth muscle tissue and the cyclin E transcription or expression level is positive or higher than that n normal uterine smooth muscle tissue to differentiate human uterine leiomyosarcoma from human uterine leiomyoma.

2. The method according to claim 1 wherein a sampled human uterine smooth muscle tissue or cell is subjected to immunohistochemical staining or immunocytochemical staining to assay expression of LMP2 and cyclin E.

3. The method according to claim 1 wherein LMP2 and cyclin E proteins are extracted from a sampled human uterine smooth muscle tissue or cell and subjected to immunoassay to examine expression of LMP2 and cyclin E.

* * * * *